(12) United States Patent
Hirano et al.

(10) Patent No.: US 7,205,132 B2
(45) Date of Patent: Apr. 17, 2007

(54) L-GLUTAMIC ACID-PRODUCING MICROORGANISM AND A METHOD FOR PRODUCING L-GLUTAMIC ACID

(75) Inventors: Seiko Hirano, Kawasaki (JP); Mikiko Yamaguchi, Kawasaki (JP); Jun Nakamura, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/222,138

(22) Filed: Sep. 9, 2005

(65) Prior Publication Data

US 2006/0057686 A1    Mar. 16, 2006

Related U.S. Application Data

(60) Provisional application No. 60/651,229, filed on Feb. 10, 2005.

(30) Foreign Application Priority Data

Sep. 10, 2004  (JP)  .............................. 2004-264458

(51) Int. Cl.
| | |
|---|---|
| C12P 13/14 | (2006.01) |
| C12Q 1/04 | (2006.01) |
| C07H 21/02 | (2006.01) |
| C07H 21/04 | (2006.01) |

(52) U.S. Cl. ..................... 435/110; 435/29; 435/252.3; 435/69.1; 435/252.32; 436/23.1; 436/23.7

(58) Field of Classification Search ..................... None
See application file for complete search history.

(56) References Cited

U.S. PATENT DOCUMENTS

| | | | |
|---|---|---|---|
| 5,492,818 | A | 2/1996 | Nakazawa et al. |
| 5,977,331 | A | 11/1999 | Asakura et al. |
| 2002/0160461 | A1 | 10/2002 | Nakai et al. |
| 2003/0077764 | A1 | 4/2003 | Tsujimoto et al. |
| 2004/0121428 | A1 | 6/2004 | Sugimoto et al. |
| 2004/0152175 | A1 | 8/2004 | Nakamura et al. |
| 2004/0214296 | A1 | 10/2004 | Asahara et al. |
| 2004/0229311 | A1 | 11/2004 | Hirano et al. |
| 2005/0014236 | A1 | 1/2005 | Matsuzaki et al. |
| 2005/0196846 | A1 | 9/2005 | Hara et al. |

FOREIGN PATENT DOCUMENTS

| | | | |
|---|---|---|---|
| EP | 0 771 879 | | 5/1997 |
| JP | 01-296994 | | 11/1989 |
| JP | WO 95/34672 | * | 7/1997 |

OTHER PUBLICATIONS

Acseesion No. AAB83185, Apr. 2001, Japan Hirano.*
Kimura, E., "Metabolic Engineering of Glutamate Production," Advances in Biochemical Engineering, Biotechnol. 2003;79:37-57.
International Search Report and the Written Opinion of the International Searching Authority for PCT App. No. PCT/JP2005/017098 (Feb. 22, 2006).
KEGG (Kyoto Encyclopedia of Genes and Genomes), Entry No. NCgl1084, 1-3.
Usuda, Y., et al., "Molecular cloning of the *Corynebacterium glutamicum* ('*Brevibacterium lactofermentum*' AJ12036) odhA gene encoding a novel type of 2-oxoglutarate dehydrogenase," Microbiology 1996;142:3347-3354.

* cited by examiner

*Primary Examiner*—Rebecca E. Prouty
*Assistant Examiner*—Md Younus Meah
(74) *Attorney, Agent, or Firm*—Cermak & Kenealy, LLP; Shelly Guest Cermak

(57) ABSTRACT

A coryneform bacterium which has an L-glutamic acid-producing ability and grows at least at the same growth rate as a non-mutated strain or a wild-type strain and has intracellular α-ketoglutarate dehydrogenase activity which is less than half that of the non-mutated or wild-type strain, and is obtained by introducing a mutation into a coding region or an expression control region of the chromosomal odhA gene encoding the E1o subunit of the α-ketoglutarate dehydrogenase complex.

8 Claims, 6 Drawing Sheets

SEQUENCE LISTING

<160> NUMBER OF SEQ ID NOS: 51

<210> SEQ ID NO 1
<211> LENGTH: 40
<212> TYPE: DNA
<213> ORGANISM: Artificial sequence
<220> FEATURE:
<223> OTHER INFORMATION: primer -continued

```
<400> SEQUENCE: 1
gccgggatcc tccggtgaat tcctgcgtac catgtctcgc                              40

<210> SEQ ID NO 2
<211> LENGTH: 40
<212> TYPE: DNA
<213> ORGANISM: Artificial sequence
<220> FEATURE:
<223> OTHER INFORMATION: primer

<400> SEQUENCE: 2
gccgggatcc ctgtgtgatt cacactgcat aaggccctct                              40

<210> SEQ ID NO 3
<211> LENGTH: 24
<212> TYPE: DNA
<213> ORGANISM: Artificial sequence
<220> FEATURE:
<223> OTHER INFORMATION: primer

<400> SEQUENCE: 3
gcttccggct cgtatgttgt gtgg                                               24

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
gatcgtgacc gcacagattc                                                    20

<210> SEQ ID NO 5
<211> LENGTH: 40
<212> TYPE: DNA
<213> ORGANISM: Artificial sequence
<220> FEATURE:
<223> OTHER INFORMATION: primer

<400> SEQUENCE: 5
gccgggatcc ccatcgccgc catccctgat ggtttcaatc                              40

<210> SEQ ID NO 6
<211> LENGTH: 40
<212> TYPE: DNA
<213> ORGANISM: Artificial sequence
<220> FEATURE:
<223> OTHER INFORMATION: primer

<400> SEQUENCE: 6
gccgggatcc ggccctggcc tgcggcggtg tcgatggcgg                              40

<210> SEQ ID NO 7
<211> LENGTH: 33
<212> TYPE: DNA
<213> ORGANISM: Artificial sequence
<220> FEATURE:
<223> OTHER INFORMATION: primer

<400> SEQUENCE: 7
gctaagcgcg tcgacgtcgg aggcaccatc cac                                     33

<210> SEQ ID NO 8
<211> LENGTH: 42
```

```
<212> TYPE: DNA
<213> ORGANISM: Artificial sequence
<220> FEATURE:
<223> OTHER INFORMATION: primer

<400> SEQUENCE: 8
ctcctaccat cgacggcagg ccccaacccct gatcgtgcct ga                              42

<210> SEQ ID NO 9
<211> LENGTH: 4394
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 9
gtcgacaagc aaaatcgaag cggcagcacg ccgcgtcgga gccttaaacg ccatcgccgc            60
catccctgat ggtttcaatc atcaagtcgg tgaacgcggg cgcaacctgt catccggaca          120
gcgccaactg atcgcgctgg cgcgcgccga actcatcgag ccttccatca tgcttctcga          180
cgaagccacc tccaccctcg accccgccac cgaagccgtt atcctcaacg cctccgatcg          240
agtcactaag ggacgcacca gcatcatcgt cgcgcaccgc ttggcaaccg ctaaaagggc          300
cgaccgtatt cttgttgttg aacaaggacg tatcattgag gacggatctc acgacgcgtt          360
gttgtctgct aacggcacct acgcccgcat gtggcattta atggcctgac acgttatttt          420
taggagaact gtcaacaaat ta atg cta caa ctg ggg ctt agg cat aat cag            472
                          Met Leu Gln Leu Gly Leu Arg His Asn Gln
                          1               5                  10 cca acg acc aac gtt aca gtg gat aaa ata aag ctc aat aaa ccc tca            520
Pro Thr Thr Asn Val Thr Val Asp Lys Ile Lys Leu Asn Lys Pro Ser
            15                  20                  25 aga agc aag gaa aag agg cga gta cct gcc gtg agc agc gct agt act            568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag            616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg            664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca            712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc            760
Ala Pro Lys Glu Ser Ala Lys Pro Ala Pro Lys Ala Ala Pro Ala Ala
                95                  100                 105 aag gca gca ccg cgc gta gaa acc aag ccg gcc gcc aag acc gcc cct            808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca            856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg            904
Gly Gln Thr Pro Ile Arg Gly Ile Phe Lys Ser Ile Ala Lys Asn Met
    140                 145                 150 gat atc tcc ctg gaa atc cca acc gca acc tcg gtt cgc gat atg cca            952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag           1000
Ala Arg Leu Met Phe Glu Asn Arg Ala Met Val Asn Asp Gln Leu Lys
```

-continued

```
Ala Arg Leu Met Phe Glu Asn Arg Ala Met Val Asn Asp Gln Leu Lys
            175                 180                 185 cgc acc cgc ggt ggc aag atc tcc ttc acc cac atc att ggc tac gcc      1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac      1096
Met Val Lys Ala Val Met Ala His Pro Asp Met Asn Asn Ser Tyr Asp
            205                 210                 215 gtc atc gac ggc aag cca acc ctg atc gtg cct gag cac atc aac ctg      1144
Val Ile Asp Gly Lys Pro Thr Leu Ile Val Pro Glu His Ile Asn Leu
220                 225                 230 ggc ctt gcc atc gac ctt cct cag aag gac ggc tcc cgc gca ctt gtc      1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc      1240
Val Ala Ala Ile Lys Glu Thr Glu Lys Met Asn Phe Ser Glu Phe Leu
            255                 260                 265 gca gca tac gaa gac atc gtg aca cgc tcc cgc aag ggc aag ctc acc      1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
            285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
            300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
            335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat      1576
Phe Leu Arg Thr Met Ser Arg Leu Leu Thr Asp Asp Ser Phe Trp Asp
            365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
            380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
            415                 420                 425 cca ctt tca tgg gtt cag cct ggc atg cca gtt cca gac cac cgc gac      1768
Pro Leu Ser Trp Val Gln Pro Gly Met Pro Val Pro Asp His Arg Asp
            430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
            445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
            460                 465                 470 gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490
```

-continued

| | |
|---|---|
| tac acc cac atc ctg gac cgc gac gag cgc acc tgg ctg cag gac cgc<br>Tyr Thr His Ile Leu Asp Arg Asp Glu Arg Thr Trp Leu Gln Asp Arg<br>                     495                     500                505 | 1960 |
| ctc gaa gcc gga atg cca aag cca acc cag gca gag cag aag tac atc<br>Leu Glu Ala Gly Met Pro Lys Pro Thr Gln Ala Glu Gln Lys Tyr Ile<br>          510                     515                   520 | 2008 |
| ctg cag aag ctg aac gcc gca gag gct ttc gag aac ttc ctg cag acc<br>Leu Gln Lys Leu Asn Ala Ala Glu Ala Phe Glu Asn Phe Leu Gln Thr<br>525                     530                     535 | 2056 |
| aag tac gtc ggc cag aag cgc ttc tcc ctc gaa ggt gca gaa gct ctc<br>Lys Tyr Val Gly Gln Lys Arg Phe Ser Leu Glu Gly Ala Glu Ala Leu<br>    540                     545                   550 | 2104 |
| atc cca ctg atg gac tcc gcc atc gac acc gcc gca ggc cag ggc ctc<br>Ile Pro Leu Met Asp Ser Ala Ile Asp Thr Ala Ala Gly Gln Gly Leu<br>555                     560                   565                 570 | 2152 |
| gac gaa gtt gtc atc ggt atg cca cac cgt ggt cgc ctc aac gtg ctg<br>Asp Glu Val Val Ile Gly Met Pro His Arg Gly Arg Leu Asn Val Leu<br>                     575                   580                585 | 2200 |
| ttc aac atc gtg ggc aag cca ctg gca tcc atc ttc aac gag ttt gaa<br>Phe Asn Ile Val Gly Lys Pro Leu Ala Ser Ile Phe Asn Glu Phe Glu<br>    590                     595                   600 | 2248 |
| ggc caa atg gag cag ggc cag atc ggt ggc tcc ggt gac gtg aag tac<br>Gly Gln Met Glu Gln Gly Gln Ile Gly Gly Ser Gly Asp Val Lys Tyr<br>605                     610                     615 | 2296 |
| cac ctc ggt tcc gaa ggc cag cac ctg cag atg ttc ggc gac ggc gag<br>His Leu Gly Ser Glu Gly Gln His Leu Gln Met Phe Gly Asp Gly Glu<br>          620                     625                   630 | 2344 |
| atc aag gtc tcc ctg act gct aac ccg tcc cac ctg gaa gct gtt aac<br>Ile Lys Val Ser Leu Thr Ala Asn Pro Ser His Leu Glu Ala Val Asn<br>635                     640                   645                 650 | 2392 |
| cca gtg atg gaa ggt atc gtc cgc gca aag cag gac tac ctg gac aag<br>Pro Val Met Glu Gly Ile Val Arg Ala Lys Gln Asp Tyr Leu Asp Lys<br>                   655                   660                665 | 2440 |
| ggc gta gac ggc aag act gtt gtg cca ctg ctc ctc cac ggt gac gct<br>Gly Val Asp Gly Lys Thr Val Val Pro Leu Leu Leu His Gly Asp Ala<br>              670                     675                   680 | 2488 |
| gca ttc gca ggc ctg ggc atc gtg cca gaa acc atc aac ctg gct aag<br>Ala Phe Ala Gly Leu Gly Ile Val Pro Glu Thr Ile Asn Leu Ala Lys<br>685                     690                   695 | 2536 |
| ctg cgt ggc tac gac gtc gga ggc acc atc cac atc gtg gtg aac aac<br>Leu Arg Gly Tyr Asp Val Gly Gly Thr Ile His Ile Val Val Asn Asn<br>    700                     705                   710 | 2584 |
| cag atc ggc ttc acc acc acc cca gac tcc agc cgc tcc atg cac tac<br>Gln Ile Gly Phe Thr Thr Thr Pro Asp Ser Ser Arg Ser Met His Tyr<br>715                     720                   725                 730 | 2632 |
| gca acc gac tac gcc aag gca ttc ggc tgc cca gtc ttc cac gtc aat<br>Ala Thr Asp Tyr Ala Lys Ala Phe Gly Cys Pro Val Phe His Val Asn<br>         735                     740                   745 | 2680 |
| ggt gat gac cca gag gca gtt gtc tgg gtt ggc cag ctg gca acc gag<br>Gly Asp Asp Pro Glu Ala Val Val Trp Val Gly Gln Leu Ala Thr Glu<br>              750                     755                   760 | 2728 |
| tac cgt cgt cgc ttc ggc aag gac gtc ttc atc gac ctc gtt tgc tac<br>Tyr Arg Arg Arg Phe Gly Lys Asp Val Phe Ile Asp Leu Val Cys Tyr<br>765                     770                   775 | 2776 |
| cgc ctc cgc ggc cac aac gaa gct gat gat cct tcc atg acc cag cca<br>Arg Leu Arg Gly His Asn Glu Ala Asp Asp Pro Ser Met Thr Gln Pro<br>    780                     785                   790 | 2824 |
| aag atg tat gag ctc atc acc ggc cgc gag acc gtt cgt gct cag tac<br>Lys Met Tyr Glu Leu Ile Thr Gly Arg Glu Thr Val Arg Ala Gln Tyr<br>795                     800                   805                 810 | 2872 |

```
acc gaa gac ctg ctc gga cgt gga gac ctc tcc aac gaa gat gca gaa    2920
Thr Glu Asp Leu Leu Gly Arg Gly Asp Leu Ser Asn Glu Asp Ala Glu
                815                 820                 825 gca gtc gtc cgc gac ttc cac gac cag atg gaa tct gtg ttc aac gaa    2968
Ala Val Val Arg Asp Phe His Asp Gln Met Glu Ser Val Phe Asn Glu
                830                 835                 840 gtc aag gaa ggc ggc aag aag cag gct gag gca cag acc ggc atc acc    3016
Val Lys Glu Gly Gly Lys Lys Gln Ala Glu Ala Gln Thr Gly Ile Thr
                845                 850                 855 ggc tcc cag aag ctt cca cac ggc ctt gag acc aac atc tcc cgt gaa    3064
Gly Ser Gln Lys Leu Pro His Gly Leu Glu Thr Asn Ile Ser Arg Glu
860                 865                 870 gag ctc ctg gaa ctg gga cag gct ttc gcc aac acc cca gaa ggc ttc    3112
Glu Leu Leu Glu Leu Gly Gln Ala Phe Ala Asn Thr Pro Glu Gly Phe
875                 880                 885                 890 aac tac cac cca cgt gtg gct cca gtt gct aag aag cgc gtc tcc tct    3160
Asn Tyr His Pro Arg Val Ala Pro Val Ala Lys Lys Arg Val Ser Ser
                895                 900                 905 gtc acc gaa ggt ggc atc gac tgg gca tgg ggc gag ctc ctc gcc ttc    3208
Val Thr Glu Gly Gly Ile Asp Trp Ala Trp Gly Glu Leu Leu Ala Phe
                910                 915                 920 ggt tcc ctg gct aac tcc ggc cgc ttg gtt cgc ctt gca ggt gaa gat    3256
Gly Ser Leu Ala Asn Ser Gly Arg Leu Val Arg Leu Ala Gly Glu Asp
                925                 930                 935 tcc cgc cgc ggt acc ttc acc cag cgc cac gca gtt gcc atc gac cca    3304
Ser Arg Arg Gly Thr Phe Thr Gln Arg His Ala Val Ala Ile Asp Pro
940                 945                 950 gcg acc gct gaa gag ttc aac cca ctc cac gag ctt gca cag tcc aag    3352
Ala Thr Ala Glu Glu Phe Asn Pro Leu His Glu Leu Ala Gln Ser Lys
955                 960                 965                 970 ggc aac aac ggt aag ttc ctg gtc tac aac tcc gca ctg acc gag tac    3400
Gly Asn Asn Gly Lys Phe Leu Val Tyr Asn Ser Ala Leu Thr Glu Tyr
                975                 980                 985 gca ggc atg ggc ttc gag tac ggc tac tcc gta gga aac gaa gac tcc    3448
Ala Gly Met Gly Phe Glu Tyr Gly Tyr Ser Val Gly Asn Glu Asp Ser
                990                 995                 1000 gtc gtt gca tgg gaa gca cag ttc ggc gac ttc gcc aac ggc gct       3493
Val Val Ala Trp Glu Ala Gln Phe Gly Asp Phe Ala Asn Gly Ala
                1005                1010                1015 cag acc atc atc gat gag tac gtc tcc tca ggc gaa gct aag tgg       3538
Gln Thr Ile Ile Asp Glu Tyr Val Ser Ser Gly Glu Ala Lys Trp
        1020                1025                1030 ggc cag acc tcc aag ctg atc ctt ctg ctg cct cac ggc tac gaa       3583
Gly Gln Thr Ser Lys Leu Ile Leu Leu Leu Pro His Gly Tyr Glu
        1035                1040                1045 ggc cag ggc cca gac cac tct tcc gca cgt atc gag cgc ttc ctg       3628
Gly Gln Gly Pro Asp His Ser Ser Ala Arg Ile Glu Arg Phe Leu
        1050                1055                1060 cag ctg tgc gct gag ggt tcc atg act gtt gct cag cca tcc acc       3673
Gln Leu Cys Ala Glu Gly Ser Met Thr Val Ala Gln Pro Ser Thr
        1065                1070                1075 cca gca aac cac ttc cac ctg ctg cgt cgt cac gct ctg tcc gac       3718
Pro Ala Asn His Phe His Leu Leu Arg Arg His Ala Leu Ser Asp
        1080                1085                1090 ctg aag cgt cca ctg gtt atc ttc acc ccg aag tcc atg ctg cgt       3763
Leu Lys Arg Pro Leu Val Ile Phe Thr Pro Lys Ser Met Leu Arg
        1095                1100                1105 aac aag gct gct gcc tcc gca cca gaa gac ttc act gag gtc acc       3808
Asn Lys Ala Ala Ala Ser Ala Pro Glu Asp Phe Thr Glu Val Thr
```

```
          1110                1115                1120
aag ttc caa  tcc gtg atc  gac gat cca  aac gtt gca  gat gca gcc             3853
Lys Phe Gln  Ser Val Ile  Asp Asp Pro  Asn Val Ala  Asp Ala Ala
             1125                1130                1135 aag gtg aag  aag gtc atg  ctg gtc tcc  ggc aag ctg  tac tac gaa             3898
Lys Val Lys  Lys Val Met  Leu Val Ser  Gly Lys Leu  Tyr Tyr Glu
             1140                1145                1150 ttg gca aag  cgc aag gag  aag gac gga  cgc gac gac  atc gcg atc             3943
Leu Ala Lys  Arg Lys Glu  Lys Asp Gly  Arg Asp Asp  Ile Ala Ile
             1155                1160                1165 gtt cgt atc  gaa atg ctc  cac cca att  ccg ttc aac  cgc atc tcc             3988
Val Arg Ile  Glu Met Leu  His Pro Ile  Pro Phe Asn  Arg Ile Ser
             1170                1175                1180 gag gct ctt  gcc ggc tac  cct aac gct  gag gaa gtc  ctc ttc gtt             4033
Glu Ala Leu  Ala Gly Tyr  Pro Asn Ala  Glu Glu Val  Leu Phe Val
             1185                1190                1195 cag gat gag  cca gca aac  cag ggc cca  tgg ccg ttc  tac cag gag             4078
Gln Asp Glu  Pro Ala Asn  Gln Gly Pro  Trp Pro Phe  Tyr Gln Glu
             1200                1205                1210 cac ctc cca  gag ctg atc  ccg aac atg  cca aag atg  cgc cgc gtt             4123
His Leu Pro  Glu Leu Ile  Pro Asn Met  Pro Lys Met  Arg Arg Val
             1215                1220                1225 tcc cgc cgc  gct cag tcc  tcc acc gca  act ggt gtt  gct aag gtg             4168
Ser Arg Arg  Ala Gln Ser  Ser Thr Ala  Thr Gly Val  Ala Lys Val
             1230                1235                1240 cac cag ctg  gag gag aag  cag ctt atc  gac gag gct  ttc gag gct             4213
His Gln Leu  Glu Glu Lys  Gln Leu Ile  Asp Glu Ala  Phe Glu Ala
             1245                1250                1255 taagtcttta tagtcctgca ctagcctaga gggccttatg cagtgtgaat cacacagcat          4273
aaggcccttt tgctgccgt ggttgcctaa ggtggaaggc atgaaacgaa tctgtgcggt           4333
cacgatctct tcagtacttt tgctaagtgg ctgctcctcc acttccacca cgcagctcga          4393
g                                                                          4394

<210> SEQ ID NO 10
<211> LENGTH: 1257
<212> TYPE: PRT
<213> ORGANISM: Corynebacterium glutamicum

<400> SEQUENCE: 10

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
```

-continued

```
                130                 135                 140
Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
                180                 185                 190

Ile Ser Phe Thr His Ile Ile Gly Tyr Ala Met Val Lys Ala Val Met
                195                 200                 205

Ala His Pro Asp Met Asn Asn Ser Tyr Asp Val Ile Asp Gly Lys Pro
210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
                260                 265                 270

Val Thr Arg Ser Arg Lys Gly Lys Leu Thr Met Asp Asp Tyr Gln Gly
                275                 280                 285

Val Thr Val Ser Leu Thr Asn Pro Gly Gly Ile Gly Thr Arg His Ser
                290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
                340                 345                 350

Arg Val Ile Gln Gly Ala Val Ser Gly Glu Phe Leu Arg Thr Met Ser
                355                 360                 365

Arg Leu Leu Thr Asp Asp Ser Phe Trp Asp Glu Ile Phe Asp Ala Met
                370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
                420                 425                 430

Pro Gly Met Pro Val Pro Asp His Arg Asp Leu Asp Ile Glu Thr His
                435                 440                 445

Ser Leu Thr Ile Trp Asp Leu Asp Arg Thr Phe Ser Val Gly Gly Phe
450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
                500                 505                 510

Lys Pro Thr Gln Ala Glu Gln Lys Tyr Ile Leu Gln Lys Leu Asn Ala
                515                 520                 525

Ala Glu Ala Phe Glu Asn Phe Leu Gln Thr Lys Tyr Val Gly Gln Lys
                530                 535                 540

Arg Phe Ser Leu Glu Gly Ala Glu Ala Leu Ile Pro Leu Met Asp Ser
545                 550                 555                 560
```

-continued

```
Ala Ile Asp Thr Ala Ala Gly Gln Gly Leu Asp Glu Val Val Ile Gly
                565                 570                 575
Met Pro His Arg Gly Arg Leu Asn Val Leu Phe Asn Ile Val Gly Lys
            580                 585                 590
Pro Leu Ala Ser Ile Phe Asn Glu Phe Glu Gly Gln Met Glu Gln Gly
        595                 600                 605
Gln Ile Gly Gly Ser Gly Asp Val Lys Tyr His Leu Gly Ser Glu Gly
    610                 615                 620
Gln His Leu Gln Met Phe Gly Asp Gly Glu Ile Lys Val Ser Leu Thr
625                 630                 635                 640
Ala Asn Pro Ser His Leu Glu Ala Val Asn Pro Val Met Glu Gly Ile
                645                 650                 655
Val Arg Ala Lys Gln Asp Tyr Leu Asp Lys Gly Val Asp Gly Lys Thr
            660                 665                 670
Val Val Pro Leu Leu His Gly Asp Ala Ala Phe Ala Gly Leu Gly
        675                 680                 685
Ile Val Pro Glu Thr Ile Asn Leu Ala Lys Leu Arg Gly Tyr Asp Val
    690                 695                 700
Gly Gly Thr Ile His Ile Val Val Asn Asn Gln Ile Gly Phe Thr Thr
705                 710                 715                 720
Thr Pro Asp Ser Ser Arg Ser Met His Tyr Ala Thr Asp Tyr Ala Lys
                725                 730                 735
Ala Phe Gly Cys Pro Val Phe His Val Asn Gly Asp Asp Pro Glu Ala
            740                 745                 750
Val Val Trp Val Gly Gln Leu Ala Thr Glu Tyr Arg Arg Arg Phe Gly
        755                 760                 765
Lys Asp Val Phe Ile Asp Leu Val Cys Tyr Arg Leu Arg Gly His Asn
    770                 775                 780
Glu Ala Asp Asp Pro Ser Met Thr Gln Pro Lys Met Tyr Glu Leu Ile
785                 790                 795                 800
Thr Gly Arg Glu Thr Val Arg Ala Gln Tyr Thr Glu Asp Leu Leu Gly
                805                 810                 815
Arg Gly Asp Leu Ser Asn Glu Asp Ala Glu Ala Val Val Arg Asp Phe
            820                 825                 830
His Asp Gln Met Glu Ser Val Phe Asn Glu Val Lys Glu Gly Gly Lys
        835                 840                 845
Lys Gln Ala Glu Ala Gln Thr Gly Ile Thr Gly Ser Gln Lys Leu Pro
    850                 855                 860
His Gly Leu Glu Thr Asn Ile Ser Arg Glu Glu Leu Leu Glu Leu Gly
865                 870                 875                 880
Gln Ala Phe Ala Asn Thr Pro Glu Gly Phe Asn Tyr His Pro Arg Val
                885                 890                 895
Ala Pro Val Ala Lys Lys Arg Val Ser Ser Val Thr Glu Gly Gly Ile
            900                 905                 910
Asp Trp Ala Trp Gly Glu Leu Leu Ala Phe Gly Ser Leu Ala Asn Ser
        915                 920                 925
Gly Arg Leu Val Arg Leu Ala Gly Glu Asp Ser Arg Arg Gly Thr Phe
    930                 935                 940
Thr Gln Arg His Ala Val Ala Ile Asp Pro Ala Thr Ala Glu Glu Phe
945                 950                 955                 960
Asn Pro Leu His Glu Leu Ala Gln Ser Lys Gly Asn Asn Gly Lys Phe
                965                 970                 975
```

-continued

```
Leu Val Tyr Asn Ser Ala Leu Thr Glu Tyr Ala Gly Met Gly Phe Glu
                980                 985                 990

Tyr Gly Tyr Ser Val Gly Asn Glu  Asp Ser Val Val Ala  Trp Glu Ala
            995                 1000                1005

Gln Phe Gly Asp Phe Ala Asn  Gly Ala Gln Thr Ile  Ile Asp Glu
        1010                1015                1020

Tyr Val Ser Ser Gly Glu Ala  Lys Trp Gly Gln Thr  Ser Lys Leu
        1025                1030                1035

Ile Leu Leu Leu Pro His Gly  Tyr Glu Gly Gln Gly  Pro Asp His
        1040                1045                1050

Ser Ser Ala Arg Ile Glu Arg  Phe Leu Gln Leu Cys  Ala Glu Gly
        1055                1060                1065

Ser Met Thr Val Ala Gln Pro  Ser Thr Pro Ala Asn  His Phe His
        1070                1075                1080

Leu Leu Arg Arg His Ala Leu  Ser Asp Leu Lys Arg  Pro Leu Val
        1085                1090                1095

Ile Phe Thr Pro Lys Ser Met  Leu Arg Asn Lys Ala  Ala Ala Ser
        1100                1105                1110

Ala Pro Glu Asp Phe Thr Glu  Val Thr Lys Phe Gln  Ser Val Ile
        1115                1120                1125

Asp Asp Pro Asn Val Ala Asp  Ala Ala Lys Val Lys  Lys Val Met
        1130                1135                1140

Leu Val Ser Gly Lys Leu Tyr  Tyr Glu Leu Ala Lys  Arg Lys Glu
        1145                1150                1155

Lys Asp Gly Arg Asp Asp Ile  Ala Ile Val Arg Ile  Glu Met Leu
        1160                1165                1170

His Pro Ile Pro Phe Asn Arg  Ile Ser Glu Ala Leu  Ala Gly Tyr
        1175                1180                1185

Pro Asn Ala Glu Glu Val Leu  Phe Val Gln Asp Glu  Pro Ala Asn
        1190                1195                1200

Gln Gly Pro Trp Pro Phe Tyr  Gln Glu His Leu Pro  Glu Leu Ile
        1205                1210                1215

Pro Asn Met Pro Lys Met Arg  Arg Val Ser Arg Arg  Ala Gln Ser
        1220                1225                1230

Ser Thr Ala Thr Gly Val Ala  Lys Val His Gln Leu  Glu Glu Lys
        1235                1240                1245

Gln Leu Ile Asp Glu Ala Phe  Glu Ala
        1250                1255

<210> SEQ ID NO 11
<211> LENGTH: 4391
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 11
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaagggc      300 cgaccgtatt cttgttgttg aacaaggacg tatcattgag gacggatctc acgacgcgtt     360
```

```
                                                        -continued gttgtctgct aacggcacct acgcccgcat gtggcattta atggcctgac acgttatttt      420
taggagaact gtcaacaaat ta atg cta caa ctg ggg ctt agg cat aat cag      472
                         Met Leu Gln Leu Gly Leu Arg His Asn Gln
                          1               5                      10 cca acg acc aac gtt aca gtg gat aaa ata aag ctc aat aaa ccc tca      520
Pro Thr Thr Asn Val Thr Val Asp Lys Ile Lys Leu Asn Lys Pro Ser
                 15                  20                  25 aga agc aag gaa aag agg cga gta cct gcc gtg agc agc gct agt act      568
Arg Ser Lys Glu Lys Arg Arg Val Pro Ala Val Ser Ser Ala Ser Thr
             30                  35                  40 ttc ggc cag aat gcg tgg ctg gta gac gag atg ttc cag cag ttc cag      616
Phe Gly Gln Asn Ala Trp Leu Val Asp Glu Met Phe Gln Gln Phe Gln
         45                  50                  55 aag gac ccc aag tcc gtg gac aag gaa tgg aga gaa ctc ttt gag gcg      664
Lys Asp Pro Lys Ser Val Asp Lys Glu Trp Arg Glu Leu Phe Glu Ala
     60                  65                  70 cag ggg gga cca aat gct acc ccc gct aca aca gaa gca cag cct tca      712
Gln Gly Gly Pro Asn Ala Thr Pro Ala Thr Thr Glu Ala Gln Pro Ser
 75                  80                  85                  90 gcg ccc aag gag tct gcg aaa cca gca cca aag gct gcc cct gca gcc      760
Ala Pro Lys Glu Ser Ala Lys Pro Ala Pro Lys Ala Ala Pro Ala Ala
                 95                 100                 105 aag gca gca ccg cgc gta gaa acc aag ccg gcc gcc aag acc gcc cct      808
Lys Ala Ala Pro Arg Val Glu Thr Lys Pro Ala Ala Lys Thr Ala Pro
             110                 115                 120 aag gcc aag gag tcc tca gtg cca cag caa cct aag ctt ccg gag cca      856
Lys Ala Lys Glu Ser Ser Val Pro Gln Gln Pro Lys Leu Pro Glu Pro
         125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
     140                 145                 150 gat atc tcc ctg gaa atc cca acc gca acc tcg gtt cgc gat atg cca      952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag     1000
Ala Arg Leu Met Phe Glu Asn Arg Ala Met Val Asn Asp Gln Leu Lys
                 175                 180                 185 cgc acc cgc ggt ggc aag atc tcc ttc acc cac atc att ggc tac gcc     1048
Arg Thr Arg Gly Gly Lys Ile Ser Phe Thr His Ile Ile Gly Tyr Ala
             190                 195                 200 atg gtg aag gca gtc atg gct cac ccg gac atg aac aac tcc tac cat     1096
Met Val Lys Ala Val Met Ala His Pro Asp Met Asn Asn Ser Tyr His
         205                 210                 215 cga cgg cag gcc cca acc ctg atc gtg cct gag cac atc aac ctg ggc     1144
Arg Arg Gln Ala Pro Thr Leu Ile Val Pro Glu His Ile Asn Leu Gly
     220                 225                 230 ctt gcc atc gac ctt cct cag aag gac ggc tcc cgc gca ctt gtc gta     1192
Leu Ala Ile Asp Leu Pro Gln Lys Asp Gly Ser Arg Ala Leu Val Val
235                 240                 245                 250 gca gcc atc aag gaa acc gag aag atg aac ttc tcc gag ttc ctc gca     1240
Ala Ala Ile Lys Glu Thr Glu Lys Met Asn Phe Ser Glu Phe Leu Ala
                 255                 260                 265 gca tac gaa gac atc gtg aca cgc tcc cgc aag ggc aag ctc acc atg     1288
Ala Tyr Glu Asp Ile Val Thr Arg Ser Arg Lys Gly Lys Leu Thr Met
             270                 275                 280 gat gac tac cag ggc gtt acc gtt tcc ttg acc aac cca ggt ggc atc     1336
Asp Asp Tyr Gln Gly Val Thr Val Ser Leu Thr Asn Pro Gly Gly Ile
         285                 290                 295
```

```
ggt acc cgc cac tct gtc cca cgt ctg acc aag ggc cag ggc acc atc      1384
Gly Thr Arg His Ser Val Pro Arg Leu Thr Lys Gly Gln Gly Thr Ile
300                 305                 310 atc ggt gtc ggt tcc atg gat tac cca gca gag ttc cag ggc gct tcc      1432
Ile Gly Val Gly Ser Met Asp Tyr Pro Ala Glu Phe Gln Gly Ala Ser
315                 320                 325                 330 gaa gac cgc ctt gca gag ctc ggc gtt gga aag ctt gtc acc atc acc      1480
Glu Asp Arg Leu Ala Glu Leu Gly Val Gly Lys Leu Val Thr Ile Thr
                335                 340                 345 tcc acc tac gat cac cgc gtg atc cag ggt gct gtg tcc ggt gaa ttc      1528
Ser Thr Tyr Asp His Arg Val Ile Gln Gly Ala Val Ser Gly Glu Phe
        350                 355                 360 ctg cgt acc atg tct cgc ctg ctc acc gat gat tcc ttc tgg gat gag      1576
Leu Arg Thr Met Ser Arg Leu Leu Thr Asp Asp Ser Phe Trp Asp Glu
365                 370                 375 atc ttc gac gca atg aac gtt cct tac acc cca atg cgt tgg gca cag      1624
Ile Phe Asp Ala Met Asn Val Pro Tyr Thr Pro Met Arg Trp Ala Gln
380                 385                 390 gac gtt cca aac acc ggt gtt gat aag aac acc cgc gtc atg cag ctc      1672
Asp Val Pro Asn Thr Gly Val Asp Lys Asn Thr Arg Val Met Gln Leu
395                 400                 405                 410 att gag gca tac cgc tcc cgt gga cac ctc atc gct gac acc aac cca      1720
Ile Glu Ala Tyr Arg Ser Arg Gly His Leu Ile Ala Asp Thr Asn Pro
                415                 420                 425 ctt tca tgg gtt cag cct ggc atg cca gtt cca gac cac cgc gac ctc      1768
Leu Ser Trp Val Gln Pro Gly Met Pro Val Pro Asp His Arg Asp Leu
        430                 435                 440 gac atc gag acc cac agc ctg acc atc tgg gat ctg gac cgt acc ttc      1816
Asp Ile Glu Thr His Ser Leu Thr Ile Trp Asp Leu Asp Arg Thr Phe
445                 450                 455 agc gtc ggt ggc ttc ggc ggc aag gag acc atg acc ctg cgc gag gta      1864
Ser Val Gly Gly Phe Gly Gly Lys Glu Thr Met Thr Leu Arg Glu Val
460                 465                 470 ctg tcc cgc ctg cgc gct gcc tac acc ttg aag gtc ggc tcc gaa tac      1912
Leu Ser Arg Leu Arg Ala Ala Tyr Thr Leu Lys Val Gly Ser Glu Tyr
475                 480                 485                 490 acc cac atc ctg gac cgc gac gag cgc acc tgg ctg cag gac cgc ctc      1960
Thr His Ile Leu Asp Arg Asp Glu Arg Thr Trp Leu Gln Asp Arg Leu
                495                 500                 505 gaa gcc gga atg cca aag cca acc cag gca gag cag aag tac atc ctg      2008
Glu Ala Gly Met Pro Lys Pro Thr Gln Ala Glu Gln Lys Tyr Ile Leu
        510                 515                 520 cag aag ctg aac gcc gca gag gct ttc gag aac ttc ctg cag acc aag      2056
Gln Lys Leu Asn Ala Ala Glu Ala Phe Glu Asn Phe Leu Gln Thr Lys
525                 530                 535 tac gtc ggc cag aag cgc ttc tcc ctc gaa ggt gca gaa gct ctc atc      2104
Tyr Val Gly Gln Lys Arg Phe Ser Leu Glu Gly Ala Glu Ala Leu Ile
540                 545                 550 cca ctg atg gac tcc gcc atc gac acc gcc gca ggc cag ggc ctc gac      2152
Pro Leu Met Asp Ser Ala Ile Asp Thr Ala Ala Gly Gln Gly Leu Asp
555                 560                 565                 570 gaa gtt gtc atc ggt atg cca cac cgt ggt cgc ctc aac gtg ctg ttc      2200
Glu Val Val Ile Gly Met Pro His Arg Gly Arg Leu Asn Val Leu Phe
                575                 580                 585 aac atc gtg ggc aag cca ctg gca tcc atc ttc aac gag ttt gaa ggc      2248
Asn Ile Val Gly Lys Pro Leu Ala Ser Ile Phe Asn Glu Phe Glu Gly
        590                 595                 600 caa atg gag cag ggc cag atc ggt ggc tcc ggt gac gtg aag tac cac      2296
Gln Met Glu Gln Gly Gln Ile Gly Gly Ser Gly Asp Val Lys Tyr His
605                 610                 615
```

-continued

| | |
|---|---|
| ctc ggt tcc gaa ggc cag cac ctg cag atg ttc ggc gac ggc gag atc<br>Leu Gly Ser Glu Gly Gln His Leu Gln Met Phe Gly Asp Gly Glu Ile<br>620                       625                     630 | 2344 |
| aag gtc tcc ctg act gct aac ccg tcc cac ctg gaa gct gtt aac cca<br>Lys Val Ser Leu Thr Ala Asn Pro Ser His Leu Glu Ala Val Asn Pro<br>635                     640                    645                  650 | 2392 |
| gtg atg gaa ggt atc gtc cgc gca aag cag gac tac ctg gac aag ggc<br>Val Met Glu Gly Ile Val Arg Ala Lys Gln Asp Tyr Leu Asp Lys Gly<br>                655                    660                  665 | 2440 |
| gta gac ggc aag act gtt gtg cca ctg ctc cac ggt gac gct gca<br>Val Asp Gly Lys Thr Val Val Pro Leu Leu His Gly Asp Ala Ala<br>           670                    675                  680 | 2488 |
| ttc gca ggc ctg ggc atc gtg cca gaa acc atc aac ctg gct aag ctg<br>Phe Ala Gly Leu Gly Ile Val Pro Glu Thr Ile Asn Leu Ala Lys Leu<br>685                     690                    695 | 2536 |
| cgt ggc tac gac gtc gga ggc acc atc cac atc gtg gtg aac aac cag<br>Arg Gly Tyr Asp Val Gly Gly Thr Ile His Ile Val Val Asn Asn Gln<br>           700                    705                  710 | 2584 |
| atc ggc ttc acc acc acc cca gac tcc agc cgc tcc atg cac tac gca<br>Ile Gly Phe Thr Thr Thr Pro Asp Ser Ser Arg Ser Met His Tyr Ala<br>715                     720                    725                  730 | 2632 |
| acc gac tac gcc aag gca ttc ggc tgc cca gtc ttc cac gtc aat ggt<br>Thr Asp Tyr Ala Lys Ala Phe Gly Cys Pro Val Phe His Val Asn Gly<br>                735                    740                  745 | 2680 |
| gat gac cca gag gca gtt gtc tgg gtt ggc cag ctg gca acc gag tac<br>Asp Asp Pro Glu Ala Val Val Trp Val Gly Gln Leu Ala Thr Glu Tyr<br>           750                    755                  760 | 2728 |
| cgt cgt cgc ttc ggc aag gac gtc ttc atc gac ctc gtt tgc tac cgc<br>Arg Arg Arg Phe Gly Lys Asp Val Phe Ile Asp Leu Val Cys Tyr Arg<br>765                     770                    775 | 2776 |
| ctc cgc ggc cac aac gaa gct gat gat cct tcc atg acc cag cca aag<br>Leu Arg Gly His Asn Glu Ala Asp Asp Pro Ser Met Thr Gln Pro Lys<br>           780                    785                  790 | 2824 |
| atg tat gag ctc atc acc ggc cgc gag acc gtt cgt gct cag tac acc<br>Met Tyr Glu Leu Ile Thr Gly Arg Glu Thr Val Arg Ala Gln Tyr Thr<br>795                     800                    805                  810 | 2872 |
| gaa gac ctg ctc gga cgt gga gac ctc tcc aac gaa gat gca gaa gca<br>Glu Asp Leu Leu Gly Arg Gly Asp Leu Ser Asn Glu Asp Ala Glu Ala<br>                815                    820                  825 | 2920 |
| gtc gtc cgc gac ttc cac gac cag atg gaa tct gtg ttc aac gaa gtc<br>Val Val Arg Asp Phe His Asp Gln Met Glu Ser Val Phe Asn Glu Val<br>           830                    835                  840 | 2968 |
| aag gaa ggc ggc aag aag cag gct gag gca cag acc ggc atc acc ggc<br>Lys Glu Gly Gly Lys Lys Gln Ala Glu Ala Gln Thr Gly Ile Thr Gly<br>845                     850                    855 | 3016 |
| tcc cag aag ctt cca cac ggc ctt gag acc aac atc tcc cgt gaa gag<br>Ser Gln Lys Leu Pro His Gly Leu Glu Thr Asn Ile Ser Arg Glu Glu<br>           860                    865                  870 | 3064 |
| ctc ctg gaa ctg gga cag gct ttc gcc aac acc cca gaa ggc ttc aac<br>Leu Leu Glu Leu Gly Gln Ala Phe Ala Asn Thr Pro Glu Gly Phe Asn<br>875                     880                    885                  890 | 3112 |
| tac cac cca cgt gtg gct cca gtt gct aag aag cgc gtc tcc tct gtc<br>Tyr His Pro Arg Val Ala Pro Val Ala Lys Lys Arg Val Ser Ser Val<br>                895                    900                  905 | 3160 |
| acc gaa ggt ggc atc gac tgg gca tgg ggc gag ctc ctc gcc ttc ggt<br>Thr Glu Gly Gly Ile Asp Trp Ala Trp Gly Glu Leu Leu Ala Phe Gly<br>           910                    915                  920 | 3208 |
| tcc ctg gct aac tcc ggc cgc ttg gtt cgc ctt gca ggt gaa gat tcc<br>Ser Leu Ala Asn Ser Gly Arg Leu Val Arg Leu Ala Gly Glu Asp Ser | 3256 |

-continued

```
            925                 930                 935
cgc cgc ggt acc ttc acc cag cgc cac gca gtt gcc atc gac cca gcg    3304
Arg Arg Gly Thr Phe Thr Gln Arg His Ala Val Ala Ile Asp Pro Ala
        940                 945                 950 acc gct gaa gag ttc aac cca ctc cac gag ctt gca cag tcc aag ggc    3352
Thr Ala Glu Glu Phe Asn Pro Leu His Glu Leu Ala Gln Ser Lys Gly
955                 960                 965                 970 aac aac ggt aag ttc ctg gtc tac aac tcc gca ctg acc gag tac gca    3400
Asn Asn Gly Lys Phe Leu Val Tyr Asn Ser Ala Leu Thr Glu Tyr Ala
                975                 980                 985 ggc atg ggc ttc gag tac ggc tac tcc gta gga aac gaa gac tcc gtc    3448
Gly Met Gly Phe Glu Tyr Gly Tyr Ser Val Gly Asn Glu Asp Ser Val
                990                 995                 1000 gtt gca tgg gaa gca cag ttc ggc gac ttc gcc aac ggc gct cag        3493
Val Ala Trp Glu Ala Gln Phe Gly Asp Phe Ala Asn Gly Ala Gln
            1005                1010                1015 acc atc atc gat gag tac gtc tcc tca ggc gaa gct aag tgg ggc        3538
Thr Ile Ile Asp Glu Tyr Val Ser Ser Gly Glu Ala Lys Trp Gly
            1020                1025                1030 cag acc tcc aag ctg atc ctt ctg ctg cct cac ggc tac gaa ggc        3583
Gln Thr Ser Lys Leu Ile Leu Leu Leu Pro His Gly Tyr Glu Gly
            1035                1040                1045 cag ggc cca gac cac tct tcc gca cgt atc gag cgc ttc ctg cag        3628
Gln Gly Pro Asp His Ser Ser Ala Arg Ile Glu Arg Phe Leu Gln
            1050                1055                1060 ctg tgc gct gag ggt tcc atg act gtt gct cag cca tcc acc cca        3673
Leu Cys Ala Glu Gly Ser Met Thr Val Ala Gln Pro Ser Thr Pro
            1065                1070                1075 gca aac cac ttc cac ctg ctg cgt cgt cac gct ctg tcc gac ctg        3718
Ala Asn His Phe His Leu Leu Arg Arg His Ala Leu Ser Asp Leu
            1080                1085                1090 aag cgt cca ctg gtt atc ttc acc ccg aag tcc atg ctg cgt aac        3763
Lys Arg Pro Leu Val Ile Phe Thr Pro Lys Ser Met Leu Arg Asn
            1095                1100                1105 aag gct gct gcc tcc gca cca gaa gac ttc act gag gtc acc aag        3808
Lys Ala Ala Ala Ser Ala Pro Glu Asp Phe Thr Glu Val Thr Lys
            1110                1115                1120 ttc caa tcc gtg atc gac gat cca aac gtt gca gat gca gcc aag        3853
Phe Gln Ser Val Ile Asp Asp Pro Asn Val Ala Asp Ala Ala Lys
            1125                1130                1135 gtg aag aag gtc atg ctg gtc tcc ggc aag ctg tac tac gaa ttg        3898
Val Lys Lys Val Met Leu Val Ser Gly Lys Leu Tyr Tyr Glu Leu
            1140                1145                1150 gca aag cgc aag gag aag gac gga cgc gac gac atc gcg atc gtt        3943
Ala Lys Arg Lys Glu Lys Asp Gly Arg Asp Asp Ile Ala Ile Val
            1155                1160                1165 cgt atc gaa atg ctc cac cca att ccg ttc aac cgc atc tcc gag        3988
Arg Ile Glu Met Leu His Pro Ile Pro Phe Asn Arg Ile Ser Glu
            1170                1175                1180 gct ctt gcc ggc tac cct aac gct gag gaa gtc ctc ttc gtt cag        4033
Ala Leu Ala Gly Tyr Pro Asn Ala Glu Glu Val Leu Phe Val Gln
            1185                1190                1195 gat gag cca gca aac cag ggc cca tgg ccg ttc tac cag gag cac        4078
Asp Glu Pro Ala Asn Gln Gly Pro Trp Pro Phe Tyr Gln Glu His
            1200                1205                1210 ctc cca gag ctg atc ccg aac atg cca aag atg cgc cgc gtt tcc        4123
Leu Pro Glu Leu Ile Pro Asn Met Pro Lys Met Arg Arg Val Ser
            1215                1220                1225 cgc cgc gct cag tcc tcc acc gca act ggt gtt gct aag gtg cac        4168
```

```
Arg Arg Ala Gln Ser Ser Thr Ala Thr Gly Val Ala Lys Val His
        1230                1235                1240 cag ctg gag gag aag cag ctt atc gac gag gct ttc gag gct taa        4213
Gln Leu Glu Glu Lys Gln Leu Ile Asp Glu Ala Phe Glu Ala
        1245                1250                1255 gtctttatag tcctgcacta gcctagaggg ccttatgcag tgtgaatcac acagcataag   4273 gcccttttg ctgccgtggt tgcctaaggt ggaaggcatg aaacgaatct gtgcggtcac    4333
gatctcttca gtacttttgc taagtggctg ctcctccact tccaccacgc agctcgag     4391

<210> SEQ ID NO 12
<211> LENGTH: 1256
<212> TYPE: PRT
<213> ORGANISM: Corynebacterium glutamicum

<400> SEQUENCE: 12

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr His Arg Arg Gln Ala Pro Thr
    210                 215                 220

Leu Ile Val Pro Glu His Ile Asn Leu Gly Leu Ala Ile Asp Leu Pro
225                 230                 235                 240

Gln Lys Asp Gly Ser Arg Ala Leu Val Val Ala Ile Lys Glu Thr
                245                 250                 255

Glu Lys Met Asn Phe Ser Glu Phe Leu Ala Ala Tyr Glu Asp Ile Val
            260                 265                 270

Thr Arg Ser Arg Lys Gly Lys Leu Thr Met Asp Asp Tyr Gln Gly Val
        275                 280                 285

Thr Val Ser Leu Thr Asn Pro Gly Gly Ile Gly Thr Arg His Ser Val
    290                 295                 300

Pro Arg Leu Thr Lys Gly Gln Gly Thr Ile Ile Gly Val Gly Ser Met
```

```
                    305                 310                 315                 320
Asp Tyr Pro Ala Glu Phe Gln Gly Ala Ser Glu Asp Arg Leu Ala Glu
                325                 330                 335
Leu Gly Val Gly Lys Leu Val Thr Ile Thr Ser Thr Tyr Asp His Arg
                340                 345                 350
Val Ile Gln Gly Ala Val Ser Gly Glu Phe Leu Arg Thr Met Ser Arg
                355                 360                 365
Leu Leu Thr Asp Asp Ser Phe Trp Asp Glu Ile Phe Asp Ala Met Asn
            370                 375                 380
Val Pro Tyr Thr Pro Met Arg Trp Ala Gln Asp Val Pro Asn Thr Gly
385                 390                 395                 400
Val Asp Lys Asn Thr Arg Val Met Gln Leu Ile Glu Ala Tyr Arg Ser
                405                 410                 415
Arg Gly His Leu Ile Ala Asp Thr Asn Pro Leu Ser Trp Val Gln Pro
                420                 425                 430
Gly Met Pro Val Pro Asp His Arg Asp Leu Asp Ile Glu Thr His Ser
            435                 440                 445
Leu Thr Ile Trp Asp Leu Asp Arg Thr Phe Ser Val Gly Gly Phe Gly
        450                 455                 460
Gly Lys Glu Thr Met Thr Leu Arg Glu Val Leu Ser Arg Leu Arg Ala
465                 470                 475                 480
Ala Tyr Thr Leu Lys Val Gly Ser Glu Tyr Thr His Ile Leu Asp Arg
                485                 490                 495
Asp Glu Arg Thr Trp Leu Gln Asp Arg Leu Glu Ala Gly Met Pro Lys
            500                 505                 510
Pro Thr Gln Ala Glu Gln Lys Tyr Ile Leu Gln Lys Leu Asn Ala Ala
        515                 520                 525
Glu Ala Phe Glu Asn Phe Leu Gln Thr Lys Tyr Val Gly Gln Lys Arg
        530                 535                 540
Phe Ser Leu Glu Gly Ala Glu Ala Leu Ile Pro Leu Met Asp Ser Ala
545                 550                 555                 560
Ile Asp Thr Ala Ala Gly Gln Gly Leu Asp Glu Val Val Ile Gly Met
                565                 570                 575
Pro His Arg Gly Arg Leu Asn Val Leu Phe Asn Ile Val Gly Lys Pro
            580                 585                 590
Leu Ala Ser Ile Phe Asn Glu Phe Glu Gly Gln Met Glu Gln Gly Gln
        595                 600                 605
Ile Gly Gly Ser Gly Asp Val Lys Tyr His Leu Gly Ser Glu Gly Gln
    610                 615                 620
His Leu Gln Met Phe Gly Asp Gly Glu Ile Lys Val Ser Leu Thr Ala
625                 630                 635                 640
Asn Pro Ser His Leu Glu Ala Val Asn Pro Val Met Glu Gly Ile Val
                645                 650                 655
Arg Ala Lys Gln Asp Tyr Leu Asp Lys Gly Val Asp Gly Lys Thr Val
                660                 665                 670
Val Pro Leu Leu Leu His Gly Asp Ala Ala Phe Ala Gly Leu Gly Ile
                675                 680                 685
Val Pro Glu Thr Ile Asn Leu Ala Lys Leu Arg Gly Tyr Asp Val Gly
            690                 695                 700
Gly Thr Ile His Ile Val Val Asn Asn Gln Ile Gly Phe Thr Thr Thr
705                 710                 715                 720
Pro Asp Ser Ser Arg Ser Met His Tyr Ala Thr Asp Tyr Ala Lys Ala
                725                 730                 735
```

-continued

```
Phe Gly Cys Pro Val Phe His Val Asn Gly Asp Asp Pro Glu Ala Val
            740                 745                 750
Val Trp Val Gly Gln Leu Ala Thr Glu Tyr Arg Arg Arg Phe Gly Lys
            755                 760                 765
Asp Val Phe Ile Asp Leu Val Cys Tyr Arg Leu Arg Gly His Asn Glu
            770                 775                 780
Ala Asp Asp Pro Ser Met Thr Gln Pro Lys Met Tyr Glu Leu Ile Thr
785                 790                 795                 800
Gly Arg Glu Thr Val Arg Ala Gln Tyr Thr Glu Asp Leu Leu Gly Arg
                805                 810                 815
Gly Asp Leu Ser Asn Glu Asp Ala Glu Ala Val Val Arg Asp Phe His
            820                 825                 830
Asp Gln Met Glu Ser Val Phe Asn Glu Val Lys Glu Gly Gly Lys Lys
            835                 840                 845
Gln Ala Glu Ala Gln Thr Gly Ile Thr Gly Ser Gln Lys Leu Pro His
            850                 855                 860
Gly Leu Glu Thr Asn Ile Ser Arg Glu Glu Leu Leu Glu Leu Gly Gln
865                 870                 875                 880
Ala Phe Ala Asn Thr Pro Glu Gly Phe Asn Tyr His Pro Arg Val Ala
                885                 890                 895
Pro Val Ala Lys Lys Arg Val Ser Ser Val Thr Glu Gly Gly Ile Asp
            900                 905                 910
Trp Ala Trp Gly Glu Leu Leu Ala Phe Gly Ser Leu Ala Asn Ser Gly
            915                 920                 925
Arg Leu Val Arg Leu Ala Gly Glu Asp Ser Arg Arg Gly Thr Phe Thr
            930                 935                 940
Gln Arg His Ala Val Ala Ile Asp Pro Ala Thr Ala Glu Glu Phe Asn
945                 950                 955                 960
Pro Leu His Glu Leu Ala Gln Ser Lys Gly Asn Asn Gly Lys Phe Leu
                965                 970                 975
Val Tyr Asn Ser Ala Leu Thr Glu Tyr Ala Gly Met Gly Phe Glu Tyr
            980                 985                 990
Gly Tyr Ser Val Gly Asn Glu Asp  Ser Val Val Ala Trp  Glu Ala Gln
            995                 1000                1005
Phe Gly  Asp Phe Ala Asn  Gly Ala Gln Thr Ile Ile  Asp Glu Tyr
            1010                1015                1020
Val Ser  Ser Gly Glu Ala Lys  Trp Gly Gln Thr Ser  Lys Leu Ile
            1025                1030                1035
Leu Leu  Leu Pro His Gly Tyr  Glu Gly Gln Gly Pro  Asp His Ser
            1040                1045                1050
Ser Ala  Arg Ile Glu Arg Phe  Leu Gln Leu Cys Ala  Glu Gly Ser
            1055                1060                1065
Met Thr  Val Ala Gln Pro Ser  Thr Pro Ala Asn His  Phe His Leu
            1070                1075                1080
Leu Arg  Arg His Ala Leu Ser  Asp Leu Lys Arg Pro  Leu Val Ile
            1085                1090                1095
Phe Thr  Pro Lys Ser Met Leu  Arg Asn Lys Ala Ala  Ala Ser Ala
            1100                1105                1110
Pro Glu  Asp Phe Thr Glu Val  Thr Lys Phe Gln Ser  Val Ile Asp
            1115                1120                1125
Asp Pro  Asn Val Ala Asp Ala  Ala Lys Val Lys Lys  Val Met Leu
            1130                1135                1140
```

-continued

| | | | | | | | | | | |
|---|---|---|---|---|---|---|---|---|---|---|
|Val|Ser|Gly|Lys|Leu|Tyr|Tyr|Glu|Leu|Ala|Lys Arg Lys Glu Lys|
| |1145| | | |1150| | | |1155| |

Asp Gly Arg Asp Asp Ile Ala Ile Val Arg Ile Glu Met Leu His
    1160            1165              1170

Pro Ile Pro Phe Asn Arg Ile Ser Glu Ala Leu Ala Gly Tyr Pro
    1175            1180              1185

Asn Ala Glu Glu Val Leu Phe Val Gln Asp Glu Pro Ala Asn Gln
    1190            1195              1200

Gly Pro Trp Pro Phe Tyr Gln Glu His Leu Pro Glu Leu Ile Pro
    1205            1210              1215

Asn Met Pro Lys Met Arg Arg Val Ser Arg Arg Ala Gln Ser Ser
    1220            1225              1230

Thr Ala Thr Gly Val Ala Lys Val His Gln Leu Glu Glu Lys Gln
    1235            1240              1245

Leu Ile Asp Glu Ala Phe Glu Ala
    1250            1255

<210> SEQ ID NO 13
<211> LENGTH: 4388
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 13

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag     472
                         Met Leu Gln Leu Gly Leu Arg His Asn Gln
                          1               5                  10
``` cca acg acc aac gtt aca gtg gat aaa ata aag ctc aat aaa ccc tca     520
Pro Thr Thr Asn Val Thr Val Asp Lys Ile Lys Leu Asn Lys Pro Ser
            15                  20                  25 aga agc aag gaa aag agg cga gta cct gcc gtg agc agc gct agt act     568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag     616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg     664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca     712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc     760
Ala Pro Lys Glu Ser Ala Lys Pro Ala Pro Lys Ala Ala Pro Ala Ala
                95                  100                 105 aag gca gca ccg cgc gta gaa acc aag ccg gcc gcc aag acc gcc cct     808
Lys Ala Ala Pro Arg Val Glu Thr Lys Pro Ala Ala Lys Thr Ala Pro -continued

```
                     110                 115                 120
aag gcc aag gag tcc tca gtg cca cag caa cct aag ctt ccg gag cca      856
Lys Ala Lys Glu Ser Ser Val Pro Gln Gln Pro Lys Leu Pro Glu Pro
            125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
        140                 145                 150 gat atc tcc ctg gaa atc cca acc gca acc tcg gtt cgc gat atg cca      952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag     1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc     1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac     1096
Met Val Lys Ala Val Met Ala His Pro Asp Met Asn Asn Ser Tyr Asp
        205                 210                 215 gtc atc gac ggc aag cca acc ctg atc gtg cct gag cac atc aac ctg     1144
Val Ile Asp Gly Lys Pro Thr Leu Ile Val Pro Glu His Ile Asn Leu
220                 225                 230 ggc ctt gcc atc gac ctt cct cag aag gac ggc tcc cgc gca ctt gtc     1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc     1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc     1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc     1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc     1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct     1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc     1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa     1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat     1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca     1624
Glu Ile Phe Asp Ala Met Asn Val Pro Tyr Thr Pro Met Arg Trp Ala
380                 385                 390 cag gac gtt cca aac acc ggt gtt gat aag aac acc cgc gtc atg cag     1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac     1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac     1768
```

-continued

```
Pro Leu Ser Trp Val Gln Pro Gly Met Pro Val Pro Asp His Arg Asp
        430                 435                 440 ctc gac atc gag acc cac agc ctg acc atc tgg gat ctg gac cgt acc    1816
Leu Asp Ile Glu Thr His Ser Leu Thr Ile Trp Asp Leu Asp Arg Thr
            445                 450                 455 ttc agc gtc ggt ggc ttc ggc ggc aag gag acc atg acc ctg cgc gag    1864
Phe Ser Val Gly Gly Phe Gly Gly Lys Glu Thr Met Thr Leu Arg Glu
    460                 465                 470 gta ctg tcc cgc ctg cgc gct gcc tac acc ttg aag gtc ggc tcc gaa    1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc    1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc    2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc    2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gct ctc    2104
Lys Tyr Val Gly Gln Lys Arg Phe Ser Leu Glu Gly Ala Glu Ala Leu
    540                 545                 550 atc cca ctg atg gac tcc gcc atc gac acc gcc gca ggc cag ggc ctc    2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg    2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa    2248
Phe Asn Ile Val Gly Lys Pro Leu Ala Ser Ile Phe Asn Glu Phe Glu
            590                 595                 600 ggc caa atg gag cag ggc cag atc ggt ggc tcc ggt gac gtg aag tac    2296
Gly Gln Met Glu Gln Gly Gln Ile Gly Gly Ser Gly Asp Val Lys Tyr
        605                 610                 615 cac ctc ggt tcc gaa ggc cag cac ctg cag atg ttc ggc gac ggc gag    2344
His Leu Gly Ser Glu Gly Gln His Leu Gln Met Phe Gly Asp Gly Glu
    620                 625                 630 atc aag gtc tcc ctg act gct aac ccg tcc cac ctg gaa gct gtt aac    2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag    2440
Pro Val Met Glu Gly Ile Val Arg Ala Lys Gln Asp Tyr Leu Asp Lys
                655                 660                 665 ggc gta gac ggc aag act gtt gtg cca ctg ctg ctc cac ggt gac gct    2488
Gly Val Asp Gly Lys Thr Val Val Pro Leu Leu Leu His Gly Asp Ala
            670                 675                 680 gca ttc gca ggc ctg ggc atc gtg cca gaa acc atc aac ctg gct aag    2536
Ala Phe Ala Gly Leu Gly Ile Val Pro Glu Thr Ile Asn Leu Ala Lys
        685                 690                 695 cgc gtc gac gtc gga ggc acc atc cac atc gtg gtg aac aac cag atc    2584
Arg Val Asp Val Gly Gly Thr Ile His Ile Val Val Asn Asn Gln Ile
    700                 705                 710 ggc ttc acc acc acc cca gac tcc agc cgc tcc atg cac tac gca acc    2632
Gly Phe Thr Thr Thr Pro Asp Ser Ser Arg Ser Met His Tyr Ala Thr
715                 720                 725                 730 gac tac gcc aag gca ttc ggc tgc cca gtc ttc cac gtc aat ggt gat    2680
Asp Tyr Ala Lys Ala Phe Gly Cys Pro Val Phe His Val Asn Gly Asp
                735                 740                 745
```

```
gac cca gag gca gtt gtc tgg gtt ggc cag ctg gca acc gag tac cgt     2728
Asp Pro Glu Ala Val Val Trp Val Gly Gln Leu Ala Thr Glu Tyr Arg
        750                 755                 760 cgt cgc ttc ggc aag gac gtc ttc atc gac ctc gtt tgc tac cgc ctc     2776
Arg Arg Phe Gly Lys Asp Val Phe Ile Asp Leu Val Cys Tyr Arg Leu
765                 770                 775 cgc ggc cac aac gaa gct gat gat cct tcc atg acc cag cca aag atg     2824
Arg Gly His Asn Glu Ala Asp Asp Pro Ser Met Thr Gln Pro Lys Met
        780                 785                 790 tat gag ctc atc acc ggc cgc gag acc gtt cgt gct cag tac acc gaa     2872
Tyr Glu Leu Ile Thr Gly Arg Glu Thr Val Arg Ala Gln Tyr Thr Glu
795                 800                 805                 810 gac ctg ctc gga cgt gga gac ctc tcc aac gaa gat gca gaa gca gtc     2920
Asp Leu Leu Gly Arg Gly Asp Leu Ser Asn Glu Asp Ala Glu Ala Val
            815                 820                 825 gtc cgc gac ttc cac gac cag atg gaa tct gtg ttc aac gaa gtc aag     2968
Val Arg Asp Phe His Asp Gln Met Glu Ser Val Phe Asn Glu Val Lys
                830                 835                 840 gaa ggc ggc aag aag cag gct gag gca cag acc ggc atc acc ggc tcc     3016
Glu Gly Gly Lys Lys Gln Ala Glu Ala Gln Thr Gly Ile Thr Gly Ser
        845                 850                 855 cag aag ctt cca cac ggc ctt gag acc aac atc tcc cgt gaa gag ctc     3064
Gln Lys Leu Pro His Gly Leu Glu Thr Asn Ile Ser Arg Glu Glu Leu
860                 865                 870 ctg gaa ctg gga cag gct ttc gcc aac acc cca gaa ggc ttc aac tac     3112
Leu Glu Leu Gly Gln Ala Phe Ala Asn Thr Pro Glu Gly Phe Asn Tyr
875                 880                 885                 890 cac cca cgt gtg gct cca gtt gct aag aag cgc gtc tcc tct gtc acc     3160
His Pro Arg Val Ala Pro Val Ala Lys Lys Arg Val Ser Ser Val Thr
            895                 900                 905 gaa ggt ggc atc gac tgg gca tgg ggc gag ctc ctc gcc ttc ggt tcc     3208
Glu Gly Gly Ile Asp Trp Ala Trp Gly Glu Leu Leu Ala Phe Gly Ser
                910                 915                 920 ctg gct aac tcc ggc cgc ttg gtt cgc ctt gca ggt gaa gat tcc cgc     3256
Leu Ala Asn Ser Gly Arg Leu Val Arg Leu Ala Gly Glu Asp Ser Arg
        925                 930                 935 cgc ggt acc ttc acc cag cgc cac gca gtt gcc atc gac cca gcg acc     3304
Arg Gly Thr Phe Thr Gln Arg His Ala Val Ala Ile Asp Pro Ala Thr
940                 945                 950 gct gaa gag ttc aac cca ctc cac gag ctt gca cag tcc aag ggc aac     3352
Ala Glu Glu Phe Asn Pro Leu His Glu Leu Ala Gln Ser Lys Gly Asn
955                 960                 965                 970 aac ggt aag ttc ctg gtc tac aac tcc gca ctg acc gag tac gca ggc     3400
Asn Gly Lys Phe Leu Val Tyr Asn Ser Ala Leu Thr Glu Tyr Ala Gly
            975                 980                 985 atg ggc ttc gag tac ggc tac tcc gta gga aac gaa gac tcc  gtc gtt    3448
Met Gly Phe Glu Tyr Gly Tyr Ser Val Gly Asn Glu Asp Ser  Val Val
                990                 995                 1000 gca tgg gaa  gca cag ttc ggc gac  ttc gcc aac ggc gct  cag acc      3493
Ala Trp Glu  Ala Gln Phe Gly Asp  Phe Ala Asn Gly Ala  Gln Thr
             1005                 1010                 1015 atc atc gat  gag tac gtc tcc tca  ggc gaa gct aag tgg  ggc cag      3538
Ile Ile Asp  Glu Tyr Val Ser Ser  Gly Glu Ala Lys Trp  Gly Gln
             1020                 1025                 1030 acc tcc aag  ctg atc ctt ctg ctg  cct cac ggc tac gaa  ggc cag      3583
Thr Ser Lys  Leu Ile Leu Leu Leu  Pro His Gly Tyr Glu  Gly Gln
             1035                 1040                 1045 ggc cca gac  cac tct tcc gca cgt  atc gag cgc ttc ctg  cag ctg      3628
Gly Pro Asp  His Ser Ser Ala Arg  Ile Glu Arg Phe Leu  Gln Leu
             1050                 1055                 1060
```

```
tgc gct gag ggt tcc atg act gtt gct cag cca tcc acc cca gca      3673
Cys Ala Glu Gly Ser Met Thr Val Ala Gln Pro Ser Thr Pro Ala
            1065                1070                1075 aac cac ttc cac ctg ctg cgt cgt cac gct ctg tcc gac ctg aag      3718
Asn His Phe His Leu Leu Arg Arg His Ala Leu Ser Asp Leu Lys
            1080                1085                1090 cgt cca ctg gtt atc ttc acc ccg aag tcc atg ctg cgt aac aag      3763
Arg Pro Leu Val Ile Phe Thr Pro Lys Ser Met Leu Arg Asn Lys
            1095                1100                1105 gct gct gcc tcc gca cca gaa gac ttc act gag gtc acc aag ttc      3808
Ala Ala Ala Ser Ala Pro Glu Asp Phe Thr Glu Val Thr Lys Phe
            1110                1115                1120 caa tcc gtg atc gac gat cca aac gtt gca gat gca gcc aag gtg      3853
Gln Ser Val Ile Asp Asp Pro Asn Val Ala Asp Ala Ala Lys Val
            1125                1130                1135 aag aag gtc atg ctg gtc tcc ggc aag ctg tac tac gaa ttg gca      3898
Lys Lys Val Met Leu Val Ser Gly Lys Leu Tyr Tyr Glu Leu Ala
            1140                1145                1150 aag cgc aag gag aag gac gga cgc gac gac atc gcg atc gtt cgt      3943
Lys Arg Lys Glu Lys Asp Gly Arg Asp Asp Ile Ala Ile Val Arg
            1155                1160                1165 atc gaa atg ctc cac cca att ccg ttc aac cgc atc tcc gag gct      3988
Ile Glu Met Leu His Pro Ile Pro Phe Asn Arg Ile Ser Glu Ala
            1170                1175                1180 ctt gcc ggc tac cct aac gct gag gaa gtc ctc ttc gtt cag gat      4033
Leu Ala Gly Tyr Pro Asn Ala Glu Glu Val Leu Phe Val Gln Asp
            1185                1190                1195 gag cca gca aac cag ggc cca tgg ccg ttc tac cag gag cac ctc      4078
Glu Pro Ala Asn Gln Gly Pro Trp Pro Phe Tyr Gln Glu His Leu
            1200                1205                1210 cca gag ctg atc ccg aac atg cca aag atg cgc cgc gtt tcc cgc      4123
Pro Glu Leu Ile Pro Asn Met Pro Lys Met Arg Arg Val Ser Arg
            1215                1220                1225 cgc gct cag tcc tcc acc gca act ggt gtt gct aag gtg cac cag      4168
Arg Ala Gln Ser Ser Thr Ala Thr Gly Val Ala Lys Val His Gln
            1230                1235                1240 ctg gag gag aag cag ctt atc gac gag gct ttc gag gct taa gtc      4213
Leu Glu Glu Lys Gln Leu Ile Asp Glu Ala Phe Glu Ala     Val
            1245                1250                1255 tttatagtcc tgcactagcc tagagggcct tatgcagtgt gaatcacaca gcataaggcc   4273 cttttttgctg ccgtggttgc ctaaggtgga aggcatgaaa cgaatctgtg cggtcacgat   4333
ctcttcagta cttttgctaa gtggctgctc ctccacttcc accacgcagc tcgag        4388
```

<210> SEQ ID NO 14
<211> LENGTH: 1255
<212> TYPE: PRT
<213> ORGANISM: Corynebacterium glutamicum

<400> SEQUENCE: 14

```
Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60
```

```
Asp Lys Glu Trp Arg Glu Leu Phe Glu Ala Gln Gly Pro Asn Ala
 65              70                  75                  80

Thr Pro Ala Thr Thr Glu Ala Gln Pro Ser Ala Pro Lys Glu Ser Ala
                 85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
    370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Ser Leu Thr Ile Trp Asp Leu Asp Arg Thr Phe Ser Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
```

-continued

```
                485                 490                 495
Arg Asp Glu Arg Thr Trp Leu Gln Asp Arg Leu Glu Ala Gly Met Pro
                500                 505                 510
Lys Pro Thr Gln Ala Glu Gln Lys Tyr Ile Leu Gln Lys Leu Asn Ala
                515                 520                 525
Ala Glu Ala Phe Glu Asn Phe Leu Gln Thr Lys Tyr Val Gly Gln Lys
                530                 535                 540
Arg Phe Ser Leu Glu Gly Ala Glu Ala Leu Ile Pro Leu Met Asp Ser
545                 550                 555                 560
Ala Ile Asp Thr Ala Gly Gln Gly Leu Asp Glu Val Val Ile Gly
                565                 570                 575
Met Pro His Arg Gly Arg Leu Asn Val Leu Phe Asn Ile Val Gly Lys
                580                 585                 590
Pro Leu Ala Ser Ile Phe Asn Glu Phe Glu Gly Gln Met Glu Gln Gly
                595                 600                 605
Gln Ile Gly Gly Ser Gly Asp Val Lys Tyr His Leu Gly Ser Glu Gly
                610                 615                 620
Gln His Leu Gln Met Phe Gly Asp Gly Glu Ile Lys Val Ser Leu Thr
625                 630                 635                 640
Ala Asn Pro Ser His Leu Glu Ala Val Asn Pro Val Met Glu Gly Ile
                645                 650                 655
Val Arg Ala Lys Gln Asp Tyr Leu Asp Lys Gly Val Asp Gly Lys Thr
                660                 665                 670
Val Val Pro Leu Leu Leu His Gly Asp Ala Ala Phe Ala Gly Leu Gly
                675                 680                 685
Ile Val Pro Glu Thr Ile Asn Leu Ala Lys Arg Val Asp Val Gly Gly
                690                 695                 700
Thr Ile His Ile Val Asn Asn Gln Ile Gly Phe Thr Thr Thr Pro
705                 710                 715                 720
Asp Ser Ser Arg Ser Met His Tyr Ala Thr Asp Tyr Ala Lys Ala Phe
                725                 730                 735
Gly Cys Pro Val Phe His Val Asn Gly Asp Asp Pro Glu Ala Val Val
                740                 745                 750
Trp Val Gly Gln Leu Ala Thr Glu Tyr Arg Arg Arg Phe Gly Lys Asp
                755                 760                 765
Val Phe Ile Asp Leu Val Cys Tyr Arg Leu Arg Gly His Asn Glu Ala
                770                 775                 780
Asp Asp Pro Ser Met Thr Gln Pro Lys Met Tyr Glu Leu Ile Thr Gly
785                 790                 795                 800
Arg Glu Thr Val Arg Ala Gln Tyr Thr Glu Asp Leu Leu Gly Arg Gly
                805                 810                 815
Asp Leu Ser Asn Glu Asp Ala Glu Ala Val Val Arg Asp Phe His Asp
                820                 825                 830
Gln Met Glu Ser Val Phe Asn Glu Val Lys Glu Gly Lys Lys Gln
                835                 840                 845
Ala Glu Ala Gln Thr Gly Ile Thr Gly Ser Gln Lys Leu Pro His Gly
                850                 855                 860
Leu Glu Thr Asn Ile Ser Arg Glu Glu Leu Leu Glu Leu Gly Gln Ala
865                 870                 875                 880
Phe Ala Asn Thr Pro Glu Gly Phe Asn Tyr His Pro Arg Val Ala Pro
                885                 890                 895
Val Ala Lys Lys Arg Val Ser Ser Val Thr Glu Gly Gly Ile Asp Trp
                900                 905                 910
```

```
Ala Trp Gly Glu Leu Leu Ala Phe Gly Ser Leu Ala Asn Ser Gly Arg
        915                 920                 925

Leu Val Arg Leu Ala Gly Glu Asp Ser Arg Arg Gly Thr Phe Thr Gln
        930                 935                 940

Arg His Ala Val Ala Ile Asp Pro Ala Thr Ala Glu Glu Phe Asn Pro
945                 950                 955                 960

Leu His Glu Leu Ala Gln Ser Lys Gly Asn Asn Gly Lys Phe Leu Val
                965                 970                 975

Tyr Asn Ser Ala Leu Thr Glu Tyr Ala Gly Met Gly Phe Glu Tyr Gly
            980                 985                 990

Tyr Ser Val Gly Asn Glu Asp Ser  Val Val Ala Trp Glu  Ala Gln Phe
        995                 1000                1005

Gly Asp  Phe Ala Asn Gly Ala  Gln Thr Ile Ile Asp  Glu Tyr Val
    1010                1015                1020

Ser Ser  Gly Glu Ala Lys Trp  Gly Gln Thr Ser Lys  Leu Ile Leu
    1025                1030                1035

Leu Leu  Pro His Gly Tyr Glu  Gly Gln Gly Pro Asp  His Ser Ser
    1040                1045                1050

Ala Arg  Ile Glu Arg Phe Leu  Gln Leu Cys Ala Glu  Gly Ser Met
    1055                1060                1065

Thr Val  Ala Gln Pro Ser Thr  Pro Ala Asn His Phe  His Leu Leu
    1070                1075                1080

Arg Arg  His Ala Leu Ser Asp  Leu Lys Arg Pro Leu  Val Ile Phe
    1085                1090                1095

Thr Pro  Lys Ser Met Leu Arg  Asn Lys Ala Ala Ala  Ser Ala Pro
    1100                1105                1110

Glu Asp  Phe Thr Glu Val Thr  Lys Phe Gln Ser Val  Ile Asp Asp
    1115                1120                1125

Pro Asn  Val Ala Asp Ala Ala  Lys Val Lys Lys Val  Met Leu Val
    1130                1135                1140

Ser Gly  Lys Leu Tyr Tyr Glu  Leu Ala Lys Arg Lys  Glu Lys Asp
    1145                1150                1155

Gly Arg  Asp Asp Ile Ala Ile  Val Arg Ile Glu Met  Leu His Pro
    1160                1165                1170

Ile Pro  Phe Asn Arg Ile Ser  Glu Ala Leu Ala Gly  Tyr Pro Asn
    1175                1180                1185

Ala Glu  Glu Val Leu Phe Val  Gln Asp Glu Pro Ala  Asn Gln Gly
    1190                1195                1200

Pro Trp  Pro Phe Tyr Gln Glu  His Leu Pro Glu Leu  Ile Pro Asn
    1205                1210                1215

Met Pro  Lys Met Arg Arg Val  Ser Arg Arg Ala Gln  Ser Ser Thr
    1220                1225                1230

Ala Thr  Gly Val Ala Lys Val  His Gln Leu Glu Glu  Lys Gln Leu
    1235                1240                1245

Ile Asp  Glu Ala Phe Glu Ala
    1250                1255

<210> SEQ ID NO 15
<211> LENGTH: 4385
<212> TYPE: DNA
<213> ORGANISM: Corynebacterium glutamicum
<220> FEATURE:
<221> NAME/KEY: CDS
<222> LOCATION: (443)..(4213)
```

<400> SEQUENCE: 15

```
gtcgacaagc aaaatcgaag cggcagcacg ccgcgtcgga gccttaaacg ccatcgccgc    60
catccctgat ggtttcaatc atcaagtcgg tgaacgcggg cgcaacctgt catccggaca   120
gcgccaactg atcgcgctgg cgcgcgccga actcatcgag ccttccatca tgcttctcga   180
cgaagccacc tccaccctcg accccgccac cgaagccgtt atcctcaacg cctccgatcg   240
agtcactaag ggacgcacca gcatcatcgt cgcgcaccgc ttggcaaccg ctaaaagggc   300
cgaccgtatt cttgttgttg aacaaggacg tatcattgag gacggatctc acgacgcgtt   360
gttgtctgct aacggcaccct acgccgcat gtggcattta atggcctgac acgttatttt   420
taggagaact gtcaacaaat ta atg cta caa ctg ggg ctt agg cat aat cag   472
                          Met Leu Gln Leu Gly Leu Arg His Asn Gln
                           1               5                  10
```

| cca acg acc aac gtt aca gtg gat aaa ata aag ctc aat aaa ccc tca | 520 |
|---|---|
| Pro Thr Thr Asn Val Thr Val Asp Lys Ile Lys Leu Asn Lys Pro Ser | |
|               15              20           25 | |

```
aga agc aag gaa aag agg cga gta cct gcc gtg agc agc gct agt act    568
Arg Ser Lys Glu Lys Arg Arg Val Pro Ala Val Ser Ser Ala Ser Thr
             30                  35                  40 ttc ggc cag aat gcg tgg ctg gta gac gag atg ttc cag cag ttc cag    616
Phe Gly Gln Asn Ala Trp Leu Val Asp Glu Met Phe Gln Gln Phe Gln
     45                  50                  55 aag gac ccc aag tcc gtg gac aag gaa tgg aga gaa ctc ttt gag gcg    664
Lys Asp Pro Lys Ser Val Asp Lys Glu Trp Arg Glu Leu Phe Glu Ala
 60                  65                  70 cag ggg gga cca aat gct acc ccc gct aca aca gaa gca cag cct tca    712
Gln Gly Gly Pro Asn Ala Thr Pro Ala Thr Thr Glu Ala Gln Pro Ser
 75                  80                  85                  90 gcg ccc aag gag tct gcg aaa cca gca cca aag gct gcc cct gca gcc    760
Ala Pro Lys Glu Ser Ala Lys Pro Ala Pro Lys Ala Ala Pro Ala Ala
                 95                 100                 105 aag gca gca ccg cgc gta gaa acc aag ccg gcc gcc aag acc gcc cct    808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca    856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg    904
Gly Gln Thr Pro Ile Arg Gly Ile Phe Lys Ser Ile Ala Lys Asn Met
    140                 145                 150 gat atc tcc ctg gaa atc cca acc gca acc tcg gtt cgc gat atg cca    952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag   1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc   1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac cat   1096
Met Val Lys Ala Val Met Ala His Pro Asp Met Asn Asn Ser Tyr His
        205                 210                 215 cga cgg cag gcc cca acc ctg atc gtg cct gag cac atc aac ctg ggc   1144
Arg Arg Gln Ala Pro Thr Leu Ile Val Pro Glu His Ile Asn Leu Gly
    220                 225                 230 ctt gcc atc gac ctt cct cag aag gac ggc tcc cgc gca ctt gtc gta   1192
Leu Ala Ile Asp Leu Pro Gln Lys Asp Gly Ser Arg Ala Leu Val Val
235                 240                 245                 250
```

```
gca gcc atc aag gaa acc gag aag atg aac ttc tcc gag ttc ctc gca    1240
Ala Ala Ile Lys Glu Thr Glu Lys Met Asn Phe Ser Glu Phe Leu Ala
            255                 260                 265 gca tac gaa gac atc gtg aca cgc tcc cgc aag ggc aag ctc acc atg    1288
Ala Tyr Glu Asp Ile Val Thr Arg Ser Arg Lys Gly Lys Leu Thr Met
        270                 275                 280 gat gac tac cag ggc gtt acc gtt tcc ttg acc aac cca ggt ggc atc    1336
Asp Asp Tyr Gln Gly Val Thr Val Ser Leu Thr Asn Pro Gly Gly Ile
    285                 290                 295 ggt acc cgc cac tct gtc cca cgt ctg acc aag ggc cag ggc acc atc    1384
Gly Thr Arg His Ser Val Pro Arg Leu Thr Lys Gly Gln Gly Thr Ile
300                 305                 310 atc ggt gtc ggt tcc atg gat tac cca gca gag ttc cag ggc gct tcc    1432
Ile Gly Val Gly Ser Met Asp Tyr Pro Ala Glu Phe Gln Gly Ala Ser
315                 320                 325                 330 gaa gac cgc ctt gca gag ctc ggc gtt gga aag ctt gtc acc atc acc    1480
Glu Asp Arg Leu Ala Glu Leu Gly Val Gly Lys Leu Val Thr Ile Thr
                335                 340                 345 tcc acc tac gat cac cgc gtg atc cag ggt gct gtg tcc ggt gaa ttc    1528
Ser Thr Tyr Asp His Arg Val Ile Gln Gly Ala Val Ser Gly Glu Phe
            350                 355                 360 ctg cgt acc atg tct cgc ctg ctc acc gat gat tcc ttc tgg gat gag    1576
Leu Arg Thr Met Ser Arg Leu Leu Thr Asp Asp Ser Phe Trp Asp Glu
        365                 370                 375 atc ttc gac gca atg aac gtt cct tac acc cca atg cgt tgg gca cag    1624
Ile Phe Asp Ala Met Asn Val Pro Tyr Thr Pro Met Arg Trp Ala Gln
    380                 385                 390 gac gtt cca aac acc ggt gtt gat aag aac acc cgc gtc atg cag ctc    1672
Asp Val Pro Asn Thr Gly Val Asp Lys Asn Thr Arg Val Met Gln Leu
395                 400                 405                 410 att gag gca tac cgc tcc cgt gga cac ctc atc gct gac acc aac cca    1720
Ile Glu Ala Tyr Arg Ser Arg Gly His Leu Ile Ala Asp Thr Asn Pro
                415                 420                 425 ctt tca tgg gtt cag cct ggc atg cca gtt cca gac cac cgc gac ctc    1768
Leu Ser Trp Val Gln Pro Gly Met Pro Val Pro Asp His Arg Asp Leu
            430                 435                 440 gac atc gag acc cac agc ctg acc atc tgg gat ctg gac cgt acc ttc    1816
Asp Ile Glu Thr His Ser Leu Thr Ile Trp Asp Leu Asp Arg Thr Phe
        445                 450                 455 agc gtc ggt ggc ttc ggc ggc aag gag acc atg acc ctg cgc gag gta    1864
Ser Val Gly Gly Phe Gly Gly Lys Glu Thr Met Thr Leu Arg Glu Val
    460                 465                 470 ctg tcc cgc ctg cgc gct gcc tac acc ttg aag gtc ggc tcc gaa tac    1912
Leu Ser Arg Leu Arg Ala Ala Tyr Thr Leu Lys Val Gly Ser Glu Tyr
475                 480                 485                 490 acc cac atc ctg gac cgc gac gag cgc acc tgg ctg cag gac cgc ctc    1960
Thr His Ile Leu Asp Arg Asp Glu Arg Thr Trp Leu Gln Asp Arg Leu
                495                 500                 505 gaa gcc gga atg cca aag cca acc cag gca gag cag aag tac atc ctg    2008
Glu Ala Gly Met Pro Lys Pro Thr Gln Ala Glu Gln Lys Tyr Ile Leu
            510                 515                 520 cag aag ctg aac gcc gca gag gct ttc gag aac ttc ctg cag acc aag    2056
Gln Lys Leu Asn Ala Ala Glu Ala Phe Glu Asn Phe Leu Gln Thr Lys
        525                 530                 535 tac gtc ggc cag aag cgc ttc tcc ctc gaa ggt gca gaa gct ctc atc    2104
Tyr Val Gly Gln Lys Arg Phe Ser Leu Glu Gly Ala Glu Ala Leu Ile
    540                 545                 550 cca ctg atg gac tcc gcc atc gac acc gcc gca ggc cag ggc ctc gac    2152
Pro Leu Met Asp Ser Ala Ile Asp Thr Ala Ala Gly Gln Gly Leu Asp
```

-continued

| | | | | |
|---|---|---|---|---|
| 555 | 560 | 565 | 570 | |
| gaa gtt gtc atc ggt atg cca cac cgt ggt cgc ctc aac gtg ctg ttc<br>Glu Val Val Ile Gly Met Pro His Arg Gly Arg Leu Asn Val Leu Phe<br>575 580 585 | | | | 2200 |
| aac atc gtg ggc aag cca ctg gca tcc atc ttc aac gag ttt gaa ggc<br>Asn Ile Val Gly Lys Pro Leu Ala Ser Ile Phe Asn Glu Phe Glu Gly<br>590 595 600 | | | | 2248 |
| caa atg gag cag ggc cag atc ggt ggc tcc ggt gac gtg aag tac cac<br>Gln Met Glu Gln Gly Gln Ile Gly Gly Ser Gly Asp Val Lys Tyr His<br>605 610 615 | | | | 2296 |
| ctc ggt tcc gaa ggc cag cac ctg cag atg ttc ggc gac ggc gag atc<br>Leu Gly Ser Glu Gly Gln His Leu Gln Met Phe Gly Asp Gly Glu Ile<br>620 625 630 | | | | 2344 |
| aag gtc tcc ctg act gct aac ccg tcc cac ctg gaa gct gtt aac cca<br>Lys Val Ser Leu Thr Ala Asn Pro Ser His Leu Glu Ala Val Asn Pro<br>635 640 645 650 | | | | 2392 |
| gtg atg gaa ggt atc gtc cgc gca aag cag gac tac ctg gac aag ggc<br>Val Met Glu Gly Ile Val Arg Ala Lys Gln Asp Tyr Leu Asp Lys Gly<br>655 660 665 | | | | 2440 |
| gta gac ggc aag act gtt gtg cca ctg ctc ctc cac ggt gac gct gca<br>Val Asp Gly Lys Thr Val Val Pro Leu Leu Leu His Gly Asp Ala Ala<br>670 675 680 | | | | 2488 |
| ttc gca ggc ctg ggc atc gtg cca gaa acc atc aac ctg gct aag cgc<br>Phe Ala Gly Leu Gly Ile Val Pro Glu Thr Ile Asn Leu Ala Lys Arg<br>685 690 695 | | | | 2536 |
| gtc gac gtc gga ggc acc atc cac atc gtg gtg aac aac cag atc ggc<br>Val Asp Val Gly Gly Thr Ile His Ile Val Val Asn Asn Gln Ile Gly<br>700 705 710 | | | | 2584 |
| ttc acc acc acc cca gac tcc agc cgc tcc atg cac tac gca acc gac<br>Phe Thr Thr Thr Pro Asp Ser Ser Arg Ser Met His Tyr Ala Thr Asp<br>715 720 725 730 | | | | 2632 |
| tac gcc aag gca ttc ggc tgc cca gtc ttc cac gtc aat ggt gat gac<br>Tyr Ala Lys Ala Phe Gly Cys Pro Val Phe His Val Asn Gly Asp Asp<br>735 740 745 | | | | 2680 |
| cca gag gca gtt gtc tgg gtt ggc cag ctg gca acc gag tac cgt cgt<br>Pro Glu Ala Val Val Trp Val Gly Gln Leu Ala Thr Glu Tyr Arg Arg<br>750 755 760 | | | | 2728 |
| cgc ttc ggc aag gac gtc ttc atc gac ctc gtt tgc tac cgc ctc cgc<br>Arg Phe Gly Lys Asp Val Phe Ile Asp Leu Val Cys Tyr Arg Leu Arg<br>765 770 775 | | | | 2776 |
| ggc cac aac gaa gct gat gat cct tcc atg acc cag cca aag atg tat<br>Gly His Asn Glu Ala Asp Asp Pro Ser Met Thr Gln Pro Lys Met Tyr<br>780 785 790 | | | | 2824 |
| gag ctc atc acc ggc cgc gag acc gtt cgt gct cag tac acc gaa gac<br>Glu Leu Ile Thr Gly Arg Glu Thr Val Arg Ala Gln Tyr Thr Glu Asp<br>795 800 805 810 | | | | 2872 |
| ctg ctc gga cgt gga gac ctc tcc aac gaa gat gca gaa gca gtc gtc<br>Leu Leu Gly Arg Gly Asp Leu Ser Asn Glu Asp Ala Glu Ala Val Val<br>815 820 825 | | | | 2920 |
| cgc gac ttc cac gac cag atg gaa tct gtg ttc aac gaa gtc aag gaa<br>Arg Asp Phe His Asp Gln Met Glu Ser Val Phe Asn Glu Val Lys Glu<br>830 835 840 | | | | 2968 |
| ggc ggc aag aag cag gct gag gca cag acc ggc atc acc ggc tcc cag<br>Gly Gly Lys Lys Gln Ala Glu Ala Gln Thr Gly Ile Thr Gly Ser Gln<br>845 850 855 | | | | 3016 |
| aag ctt cca cac ggc ctt gag acc aac atc tcc cgt gaa gag ctc ctg<br>Lys Leu Pro His Gly Leu Glu Thr Asn Ile Ser Arg Glu Glu Leu Leu<br>860 865 870 | | | | 3064 |
| gaa ctg gga cag gct ttc gcc aac acc cca gaa ggc ttc aac tac cac<br>Glu Leu Gly Gln Ala Phe Ala Asn Thr Pro Glu Gly Phe Asn Tyr His | | | | 3112 |

```
Glu Leu Gly Gln Ala Phe Ala Asn Thr Pro Glu Gly Phe Asn Tyr His
875                 880                 885                 890 cca cgt gtg gct cca gtt gct aag aag cgc gtc tcc tct gtc acc gaa         3160
Pro Arg Val Ala Pro Val Ala Lys Lys Arg Val Ser Ser Val Thr Glu
                    895                 900                 905 ggt ggc atc gac tgg gca tgg ggc gag ctc ctc gcc ttc ggt tcc ctg         3208
Gly Gly Ile Asp Trp Ala Trp Gly Glu Leu Leu Ala Phe Gly Ser Leu
            910                 915                 920 gct aac tcc ggc cgc ttg gtt cgc ctt gca ggt gaa gat tcc cgc cgc         3256
Ala Asn Ser Gly Arg Leu Val Arg Leu Ala Gly Glu Asp Ser Arg Arg
        925                 930                 935 ggt acc ttc acc cag cgc cac gca gtt gcc atc gac cca gcg acc gct         3304
Gly Thr Phe Thr Gln Arg His Ala Val Ala Ile Asp Pro Ala Thr Ala
    940                 945                 950 gaa gag ttc aac cca ctc cac gag ctt gca cag tcc aag ggc aac aac         3352
Glu Glu Phe Asn Pro Leu His Glu Leu Ala Gln Ser Lys Gly Asn Asn
955                 960                 965                 970 ggt aag ttc ctg gtc tac aac tcc gca ctg acc gag tac gca ggc atg         3400
Gly Lys Phe Leu Val Tyr Asn Ser Ala Leu Thr Glu Tyr Ala Gly Met
                975                 980                 985 ggc ttc gag tac ggc tac tcc gta gga aac gaa gac tcc gtc  gtt gca        3448
Gly Phe Glu Tyr Gly Tyr Ser Val Gly Asn Glu Asp Ser Val  Val Ala
            990                 995                 1000 tgg gaa gca  cag ttc ggc gac ttc  gcc aac ggc gct cag  acc atc          3493
Trp Glu Ala  Gln Phe Gly Asp Phe  Ala Asn Gly Ala Gln  Thr Ile
             1005                 1010                 1015 atc gat gag  tac gtc tcc tca ggc  gaa gct aag tgg ggc  cag acc          3538
Ile Asp Glu  Tyr Val Ser Ser Gly  Glu Ala Lys Trp Gly  Gln Thr
             1020                 1025                 1030 tcc aag ctg  atc ctt ctg ctg cct  cac ggc tac gaa ggc  cag ggc          3583
Ser Lys Leu  Ile Leu Leu Leu Pro  His Gly Tyr Glu Gly  Gln Gly
             1035                 1040                 1045 cca gac cac  tct tcc gca cgt atc  gag cgc ttc ctg cag  ctg tgc          3628
Pro Asp His  Ser Ser Ala Arg Ile  Glu Arg Phe Leu Gln  Leu Cys
             1050                 1055                 1060 gct gag ggt  tcc atg act gtt gct  cag cca tcc acc cca  gca aac          3673
Ala Glu Gly  Ser Met Thr Val Ala  Gln Pro Ser Thr Pro  Ala Asn
             1065                 1070                 1075 cac ttc cac  ctg ctg cgt cgt cac  gct ctg tcc gac ctg  aag cgt          3718
His Phe His  Leu Leu Arg Arg His  Ala Leu Ser Asp Leu  Lys Arg
             1080                 1085                 1090 cca ctg gtt  atc ttc acc ccg aag  tcc atg ctg cgt aac  aag gct          3763
Pro Leu Val  Ile Phe Thr Pro Lys  Ser Met Leu Arg Asn  Lys Ala
             1095                 1100                 1105 gct gcc tcc  gca cca gaa gac ttc  act gag gtc acc aag  ttc caa          3808
Ala Ala Ser  Ala Pro Glu Asp Phe  Thr Glu Val Thr Lys  Phe Gln
             1110                 1115                 1120 tcc gtg atc  gac gat cca aac gtt  gca gat gca gcc aag  gtg aag          3853
Ser Val Ile  Asp Asp Pro Asn Val  Ala Asp Ala Ala Lys  Val Lys
             1125                 1130                 1135 aag gtc atg  ctg gtc tcc ggc aag  ctg tac tac gaa ttg  gca aag          3898
Lys Val Met  Leu Val Ser Gly Lys  Leu Tyr Tyr Glu Leu  Ala Lys
             1140                 1145                 1150 cgc aag gag  aag gac gga cgc gac  gac atc gcg atc gtt  cgt atc          3943
Arg Lys Glu  Lys Asp Gly Arg Asp  Asp Ile Ala Ile Val  Arg Ile
             1155                 1160                 1165 gaa atg ctc  cac cca att ccg ttc  aac cgc atc tcc gag  gct ctt          3988
Glu Met Leu  His Pro Ile Pro Phe  Asn Arg Ile Ser Glu  Ala Leu
             1170                 1175                 1180
```

```
gcc ggc tac cct aac gct gag gaa gtc ctc ttc gtt cag gat gag      4033
Ala Gly Tyr Pro Asn Ala Glu Glu Val Leu Phe Val Gln Asp Glu
            1185                1190                1195 cca gca aac cag ggc cca tgg ccg ttc tac cag gag cac ctc cca      4078
Pro Ala Asn Gln Gly Pro Trp Pro Phe Tyr Gln Glu His Leu Pro
        1200                1205                1210 gag ctg atc ccg aac atg cca aag atg cgc cgc gtt tcc cgc cgc      4123
Glu Leu Ile Pro Asn Met Pro Lys Met Arg Arg Val Ser Arg Arg
    1215                1220                1225 gct cag tcc tcc acc gca act ggt gtt gct aag gtg cac cag ctg      4168
Ala Gln Ser Ser Thr Ala Thr Gly Val Ala Lys Val His Gln Leu
1230                1235                1240 gag gag aag cag ctt atc gac gag gct ttc gag gct taa gtc ttt      4213
Glu Glu Lys Gln Leu Ile Asp Glu Ala Phe Glu Ala     Val Phe
        1245                1250                1255 atagtcctgc actagcctag agggccttat gcagtgtgaa tcacacagca taaggccctt      4273
tttgctgccg tggttgccta aggtggaagg catgaaacga atctgtgcgg tcacgatctc      4333
ttcagtactt tgctaagtg gctgctcctc cacttccacc acgcagctcg ag            4385
```

<210> SEQ ID NO 16
<211> LENGTH: 1254
<212> TYPE: PRT
<213> ORGANISM: Corynebacterium glutamicum

<400> SEQUENCE: 16

```
Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr His Arg Arg Gln Ala Pro Thr
    210                 215                 220

Leu Ile Val Pro Glu His Ile Asn Leu Gly Leu Ala Ile Asp Leu Pro
225                 230                 235                 240
```

```
Gln Lys Asp Gly Ser Arg Ala Leu Val Val Ala Ala Ile Lys Glu Thr
                245                 250                 255

Glu Lys Met Asn Phe Ser Glu Phe Leu Ala Ala Tyr Glu Asp Ile Val
            260                 265                 270

Thr Arg Ser Arg Lys Gly Lys Leu Thr Met Asp Asp Tyr Gln Gly Val
        275                 280                 285

Thr Val Ser Leu Thr Asn Pro Gly Ile Gly Thr Arg His Ser Val
    290                 295                 300

Pro Arg Leu Thr Lys Gly Gln Gly Thr Ile Ile Gly Val Gly Ser Met
305                 310                 315                 320

Asp Tyr Pro Ala Glu Phe Gln Gly Ala Ser Glu Asp Arg Leu Ala Glu
                325                 330                 335

Leu Gly Val Gly Lys Leu Val Thr Ile Thr Ser Thr Tyr Asp His Arg
            340                 345                 350

Val Ile Gln Gly Ala Val Ser Gly Glu Phe Leu Arg Thr Met Ser Arg
        355                 360                 365

Leu Leu Thr Asp Asp Ser Phe Trp Asp Glu Ile Phe Asp Ala Met Asn
    370                 375                 380

Val Pro Tyr Thr Pro Met Arg Trp Ala Gln Asp Val Pro Asn Thr Gly
385                 390                 395                 400

Val Asp Lys Asn Thr Arg Val Met Gln Leu Ile Glu Ala Tyr Arg Ser
                405                 410                 415

Arg Gly His Leu Ile Ala Asp Thr Asn Pro Leu Ser Trp Val Gln Pro
            420                 425                 430

Gly Met Pro Val Pro Asp His Arg Asp Leu Asp Ile Glu Thr His Ser
        435                 440                 445

Leu Thr Ile Trp Asp Leu Asp Arg Thr Phe Ser Val Gly Gly Phe Gly
    450                 455                 460

Gly Lys Glu Thr Met Thr Leu Arg Glu Val Leu Ser Arg Leu Arg Ala
465                 470                 475                 480

Ala Tyr Thr Leu Lys Val Gly Ser Glu Tyr Thr His Ile Leu Asp Arg
                485                 490                 495

Asp Glu Arg Thr Trp Leu Gln Asp Arg Leu Glu Ala Gly Met Pro Lys
            500                 505                 510

Pro Thr Gln Ala Glu Gln Lys Tyr Ile Leu Gln Lys Leu Asn Ala Ala
        515                 520                 525

Glu Ala Phe Glu Asn Phe Leu Gln Thr Lys Tyr Val Gly Gln Lys Arg
    530                 535                 540

Phe Ser Leu Glu Gly Ala Glu Ala Leu Ile Pro Leu Met Asp Ser Ala
545                 550                 555                 560

Ile Asp Thr Ala Ala Gly Gln Gly Leu Asp Glu Val Val Ile Gly Met
                565                 570                 575

Pro His Arg Gly Arg Leu Asn Val Leu Phe Asn Ile Val Gly Lys Pro
            580                 585                 590

Leu Ala Ser Ile Phe Asn Glu Phe Glu Gly Gln Met Glu Gln Gly Gln
        595                 600                 605

Ile Gly Gly Ser Gly Asp Val Lys Tyr His Leu Gly Ser Glu Gly Gln
    610                 615                 620

His Leu Gln Met Phe Gly Asp Gly Glu Ile Lys Val Ser Leu Thr Ala
625                 630                 635                 640

Asn Pro Ser His Leu Glu Ala Val Asn Pro Val Met Glu Gly Ile Val
                645                 650                 655

Arg Ala Lys Gln Asp Tyr Leu Asp Lys Gly Val Asp Gly Lys Thr Val
```

-continued

```
                    660             665             670
Val Pro Leu Leu His Gly Asp Ala Ala Phe Ala Gly Leu Gly Ile
        675             680             685
Val Pro Glu Thr Ile Asn Leu Ala Lys Arg Val Asp Val Gly Gly Thr
        690             695             700
Ile His Ile Val Val Asn Asn Gln Ile Gly Phe Thr Thr Thr Pro Asp
705             710             715             720
Ser Ser Arg Ser Met His Tyr Ala Thr Asp Tyr Ala Lys Ala Phe Gly
                725             730             735
Cys Pro Val Phe His Val Asn Gly Asp Asp Pro Glu Ala Val Val Trp
        740             745             750
Val Gly Gln Leu Ala Thr Glu Tyr Arg Arg Phe Gly Lys Asp Val
        755             760             765
Phe Ile Asp Leu Val Cys Tyr Arg Leu Arg Gly His Asn Glu Ala Asp
        770             775             780
Asp Pro Ser Met Thr Gln Pro Lys Met Tyr Glu Leu Ile Thr Gly Arg
785             790             795             800
Glu Thr Val Arg Ala Gln Tyr Thr Glu Asp Leu Leu Gly Arg Gly Asp
            805             810             815
Leu Ser Asn Glu Asp Ala Glu Ala Val Val Arg Asp Phe His Asp Gln
        820             825             830
Met Glu Ser Val Phe Asn Glu Val Lys Glu Gly Gly Lys Lys Gln Ala
    835             840             845
Glu Ala Gln Thr Gly Ile Thr Gly Ser Gln Lys Leu Pro His Gly Leu
    850             855             860
Glu Thr Asn Ile Ser Arg Glu Glu Leu Leu Glu Leu Gly Gln Ala Phe
865             870             875             880
Ala Asn Thr Pro Glu Gly Phe Asn Tyr His Pro Arg Val Ala Pro Val
                885             890             895
Ala Lys Lys Arg Val Ser Ser Val Thr Glu Gly Gly Ile Asp Trp Ala
            900             905             910
Trp Gly Glu Leu Leu Ala Phe Gly Ser Leu Ala Asn Ser Gly Arg Leu
        915             920             925
Val Arg Leu Ala Gly Glu Asp Ser Arg Arg Gly Thr Phe Thr Gln Arg
    930             935             940
His Ala Val Ala Ile Asp Pro Ala Thr Ala Glu Glu Phe Asn Pro Leu
945             950             955             960
His Glu Leu Ala Gln Ser Lys Gly Asn Asn Gly Lys Phe Leu Val Tyr
                965             970             975
Asn Ser Ala Leu Thr Glu Tyr Ala Gly Met Gly Phe Glu Tyr Gly Tyr
            980             985             990
Ser Val Gly Asn Glu Asp Ser Val  Val Ala Trp Glu Ala  Gln Phe Gly
            995             1000             1005
Asp Phe Ala Asn Gly Ala Gln  Thr Ile Ile Asp Glu  Tyr Val Ser
        1010             1015             1020
Ser Gly Glu Ala Lys Trp Gly  Gln Thr Ser Lys Leu  Ile Leu Leu
        1025             1030             1035
Leu Pro His Gly Tyr Glu Gly  Gln Gly Pro Asp His  Ser Ser Ala
        1040             1045             1050
Arg Ile Glu Arg Phe Leu Gln  Leu Cys Ala Glu Gly  Ser Met Thr
        1055             1060             1065
Val Ala  Gln Pro Ser Thr Pro  Ala Asn His Phe His  Leu Leu Arg
        1070             1075             1080
```

```
Arg His Ala Leu Ser Asp Leu Lys Arg Pro Leu Val Ile Phe Thr
    1085                1090                1095

Pro Lys Ser Met Leu Arg Asn Lys Ala Ala Ser Ala Pro Glu
    1100                1105                1110

Asp Phe Thr Glu Val Thr Lys Phe Gln Ser Val Ile Asp Asp Pro
    1115                1120                1125

Asn Val Ala Asp Ala Ala Lys Val Lys Lys Val Met Leu Val Ser
    1130                1135                1140

Gly Lys Leu Tyr Tyr Glu Leu Ala Lys Arg Lys Glu Lys Asp Gly
    1145                1150                1155

Arg Asp Asp Ile Ala Ile Val Arg Ile Glu Met Leu His Pro Ile
    1160                1165                1170

Pro Phe Asn Arg Ile Ser Glu Ala Leu Ala Gly Tyr Pro Asn Ala
    1175                1180                1185

Glu Glu Val Leu Phe Val Gln Asp Glu Pro Ala Asn Gln Gly Pro
    1190                1195                1200

Trp Pro Phe Tyr Gln Glu His Leu Pro Glu Leu Ile Pro Asn Met
    1205                1210                1215

Pro Lys Met Arg Arg Val Ser Arg Arg Ala Gln Ser Ser Thr Ala
    1220                1225                1230

Thr Gly Val Ala Lys Val His Gln Leu Glu Glu Lys Gln Leu Ile
    1235                1240                1245

Asp Glu Ala Phe Glu Ala
    1250

<210> SEQ ID NO 17
<211> LENGTH: 1800
<212> TYPE: DNA
<213> ORGANISM: Corynebacterium glutamicum
<220> FEATURE:
<221> NAME/KEY: CDS
<222> LOCATION: (211)..(1620)

<400> SEQUENCE: 17
gatcctccgc attcagtaat cttttcccaca gcatcggctt gttctaaaac agcacggtgc      60
ttagaccgta cataaaacac ctgcatttct gtgcccattt gggcccggat gtgggtgttt     120 ttcatttttct tccactctaa aattaagtat ggaaaaccaa ccgcacccgg atgcacgaca    180
atgacccact aaacacgtat ccttgaatgc gtg act gaa cat tat gac gta gta     234
                                 Met Thr Glu His Tyr Asp Val Val
                                   1               5 gta ctc gga gcc ggc ccc ggt ggc tat gtc tcc gcc atc cgt gca gcg      282
Val Leu Gly Ala Gly Pro Gly Gly Tyr Val Ser Ala Ile Arg Ala Ala
        10                  15                  20 cag ctt ggc aag aag gtt gct gta att gag aag cag tac tgg ggt ggt      330
Gln Leu Gly Lys Lys Val Ala Val Ile Glu Lys Gln Tyr Trp Gly Gly
25                  30                  35                  40 gtt tgc cta aac gtg ggc tgc att cct tcc aag tct ctg atc aaa aac      378
Val Cys Leu Asn Val Gly Cys Ile Pro Ser Lys Ser Leu Ile Lys Asn
                45                  50                  55 gct gaa gtt gcc cat acc ttt acc cat gag aag aag acc ttc ggc atc      426
Ala Glu Val Ala His Thr Phe Thr His Glu Lys Lys Thr Phe Gly Ile
            60                  65                  70 aat ggc gaa gtg acc ttc aac tat gag gat gct cac aag cgt tcc cgt      474
Asn Gly Glu Val Thr Phe Asn Tyr Glu Asp Ala His Lys Arg Ser Arg
        75                  80                  85 ggc gtt tcc gac aag atc gtt gga ggc gtt cat tac ttg atg aag aag      522
```

```
Gly Val Ser Asp Lys Ile Val Gly Val His Tyr Leu Met Lys Lys
     90               95              100 aac aag atc atc gaa att cat ggt ctt gga aac ttc aag gat gct aag        570
Asn Lys Ile Ile Glu Ile His Gly Leu Gly Asn Phe Lys Asp Ala Lys
105              110              115              120 act ctt gag gtc acc gac ggt aag gat gct ggc aag acc atc acc ttt        618
Thr Leu Glu Val Thr Asp Gly Lys Asp Ala Gly Lys Thr Ile Thr Phe
                125              130              135 gat gac tgc atc atc gca acc ggt tcg gta gtc aac acc ctc cgt ggc        666
Asp Asp Cys Ile Ile Ala Thr Gly Ser Val Val Asn Thr Leu Arg Gly
            140              145              150 gtt gac ttc tca gag aac gtt gtg tct ttt gaa gag cag att ctt aac        714
Val Asp Phe Ser Glu Asn Val Val Ser Phe Glu Glu Gln Ile Leu Asn
        155              160              165 cct gtt gcg cca aag aag atg gtc att gtt ggt gca ggc gca att gga        762
Pro Val Ala Pro Lys Lys Met Val Ile Val Gly Ala Gly Ala Ile Gly
    170              175              180 atg gaa ttc gcc tac gtt ctt ggt aac tac ggt gta gat gta acc gtc        810
Met Glu Phe Ala Tyr Val Leu Gly Asn Tyr Gly Val Asp Val Thr Val
185              190              195              200 atc gag ttc atg gat cgt gtg ctt cca aat gaa gat gct gaa gtc tcc        858
Ile Glu Phe Met Asp Arg Val Leu Pro Asn Glu Asp Ala Glu Val Ser
                205              210              215 aag gtt att gca aag gcc tac aag aag atg ggc gtt aag ctt ctt cct        906
Lys Val Ile Ala Lys Ala Tyr Lys Lys Met Gly Val Lys Leu Leu Pro
            220              225              230 ggc cat gca acc act gct gtt cgg gac aac ggt gac ttt gtc gag gtt        954
Gly His Ala Thr Thr Ala Val Arg Asp Asn Gly Asp Phe Val Glu Val
        235              240              245 gat tac cag aag aag ggc tct gac aag aca gag act ctt act gtt gat       1002
Asp Tyr Gln Lys Lys Gly Ser Asp Lys Thr Glu Thr Leu Thr Val Asp
    250              255              260 cga gtc atg gtt tcc gtt ggt ttc cgt cca cgc gtt gag gga ttt ggt       1050
Arg Val Met Val Ser Val Gly Phe Arg Pro Arg Val Glu Gly Phe Gly
265              270              275              280 ctt gaa aac act ggc gtt aag ctc acc gag cgt ggc gca atc gag atc       1098
Leu Glu Asn Thr Gly Val Lys Leu Thr Glu Arg Gly Ala Ile Glu Ile
                285              290              295 gat gat tac atg cgt acc aac gtc gat ggc att tac gcc atc ggt gac       1146
Asp Asp Tyr Met Arg Thr Asn Val Asp Gly Ile Tyr Ala Ile Gly Asp
            300              305              310 gtg acc gcc aag ctt cag ctt gct cac gtc gca gaa gca cag ggc att       1194
Val Thr Ala Lys Leu Gln Leu Ala His Val Ala Glu Ala Gln Gly Ile
        315              320              325 gtt gcc gca gag act att gct ggt gca gaa act cag act ctt ggt gat       1242
Val Ala Ala Glu Thr Ile Ala Gly Ala Glu Thr Gln Thr Leu Gly Asp
    330              335              340 tac atg atg atg cca cgt gca acc ttc tgc aac cca cag gtt tct tcc       1290
Tyr Met Met Met Pro Arg Ala Thr Phe Cys Asn Pro Gln Val Ser Ser
345              350              355              360 ttt ggt tac acc gaa gag cag gcc aag gag aag tgg cca gat cgt gag       1338
Phe Gly Tyr Thr Glu Glu Gln Ala Lys Glu Lys Trp Pro Asp Arg Glu
                365              370              375 atc aag gtt gct tcc ctc cca ttc tct gca aac ggt aaa gca gtt ggc       1386
Ile Lys Val Ala Ser Leu Pro Phe Ser Ala Asn Gly Lys Ala Val Gly
            380              385              390 ctg gca gaa act gat ggt ttc gca aag atc gtt gct gat gca gaa ttc       1434
Leu Ala Glu Thr Asp Gly Phe Ala Lys Ile Val Ala Asp Ala Glu Phe
        395              400              405
```

-continued

```
ggt gag ctg ctc ggt gca cac ctg gtt gga gca aat gca tca gag ctc    1482
Gly Glu Leu Leu Gly Ala His Leu Val Gly Ala Asn Ala Ser Glu Leu
        410                 415                 420 atc aat gaa ttg gtg ctt gct cag aac tgg gat ctc acc act gaa gag    1530
Ile Asn Glu Leu Val Leu Ala Gln Asn Trp Asp Leu Thr Thr Glu Glu
425                 430                 435                 440 atc tct cgt agc gtc cat att cac cca acg cta tct gag gca gtt aag    1578
Ile Ser Arg Ser Val His Ile His Pro Thr Leu Ser Glu Ala Val Lys
                445                 450                 455 gaa gct gca cac ggt atc tct gga cac atg atc aac ttc tag            1620
Glu Ala Ala His Gly Ile Ser Gly His Met Ile Asn Phe
                460                 465 aatccacctc gttggccctg tttctgtatg gaaacagggc caaaaccgat tttcaatcca  1680
aaccgagtgc tggttagtgc tcatactcac acaaactttt cgattatcaa agagaattat  1740
ttctaaaatt cggtatcgtc taagaaatga gtttgccaat agctcagcat caaaatgctg  1800
```

<210> SEQ ID NO 18
<211> LENGTH: 469
<212> TYPE: PRT
<213> ORGANISM: Corynebacterium glutamicum

<400> SEQUENCE: 18

```
Met Thr Glu His Tyr Asp Val Val Leu Gly Ala Gly Pro Gly Gly
1               5                   10                  15

Tyr Val Ser Ala Ile Arg Ala Ala Gln Leu Gly Lys Lys Val Ala Val
                20                  25                  30

Ile Glu Lys Gln Tyr Trp Gly Gly Val Cys Leu Asn Val Gly Cys Ile
            35                  40                  45

Pro Ser Lys Ser Leu Ile Lys Asn Ala Glu Val Ala His Thr Phe Thr
        50                  55                  60

His Glu Lys Lys Thr Phe Gly Ile Asn Gly Glu Val Thr Phe Asn Tyr
65                  70                  75                  80

Glu Asp Ala His Lys Arg Ser Arg Gly Val Ser Asp Lys Ile Val Gly
                85                  90                  95

Gly Val His Tyr Leu Met Lys Lys Asn Lys Ile Ile Glu Ile His Gly
                100                 105                 110

Leu Gly Asn Phe Lys Asp Ala Lys Thr Leu Glu Val Thr Asp Gly Lys
            115                 120                 125

Asp Ala Gly Lys Thr Ile Thr Phe Asp Asp Cys Ile Ile Ala Thr Gly
        130                 135                 140

Ser Val Val Asn Thr Leu Arg Gly Val Asp Phe Ser Glu Asn Val Val
145                 150                 155                 160

Ser Phe Glu Glu Gln Ile Leu Asn Pro Val Ala Pro Lys Lys Met Val
                165                 170                 175

Ile Val Gly Ala Gly Ala Ile Gly Met Glu Phe Ala Tyr Val Leu Gly
            180                 185                 190

Asn Tyr Gly Val Asp Val Thr Val Ile Glu Phe Met Asp Arg Val Leu
        195                 200                 205

Pro Asn Glu Asp Ala Glu Val Ser Lys Val Ile Ala Lys Ala Tyr Lys
    210                 215                 220

Lys Met Gly Val Lys Leu Leu Pro Gly His Ala Thr Thr Ala Val Arg
225                 230                 235                 240

Asp Asn Gly Asp Phe Val Glu Val Asp Tyr Gln Lys Lys Gly Ser Asp
                245                 250                 255

Lys Thr Glu Thr Leu Thr Val Asp Arg Val Met Val Ser Val Gly Phe
```

-continued

```
                260                 265                 270
Arg Pro Arg Val Glu Gly Phe Gly Leu Glu Asn Thr Gly Val Lys Leu
        275                 280                 285

Thr Glu Arg Gly Ala Ile Glu Ile Asp Asp Tyr Met Arg Thr Asn Val
    290                 295                 300

Asp Gly Ile Tyr Ala Ile Gly Asp Val Thr Ala Lys Leu Gln Leu Ala
305                 310                 315                 320

His Val Ala Glu Ala Gln Gly Ile Val Ala Ala Glu Thr Ile Ala Gly
                325                 330                 335

Ala Glu Thr Gln Thr Leu Gly Asp Tyr Met Met Pro Arg Ala Thr
        340                 345                 350

Phe Cys Asn Pro Gln Val Ser Ser Phe Gly Tyr Thr Glu Glu Gln Ala
        355                 360                 365

Lys Glu Lys Trp Pro Asp Arg Glu Ile Lys Val Ala Ser Leu Pro Phe
        370                 375                 380

Ser Ala Asn Gly Lys Ala Val Gly Leu Ala Glu Thr Asp Gly Phe Ala
385                 390                 395                 400

Lys Ile Val Ala Asp Ala Glu Phe Gly Glu Leu Leu Gly Ala His Leu
                405                 410                 415

Val Gly Ala Asn Ala Ser Glu Leu Ile Asn Glu Leu Val Leu Ala Gln
                420                 425                 430

Asn Trp Asp Leu Thr Thr Glu Glu Ile Ser Arg Ser Val His Ile His
            435                 440                 445

Pro Thr Leu Ser Glu Ala Val Lys Glu Ala His Gly Ile Ser Gly
        450                 455                 460

His Met Ile Asn Phe
465
```

<210> SEQ ID NO 19
<211> LENGTH: 2014
<212> TYPE: DNA
<213> ORGANISM: Bacillus subtilis
<220> FEATURE:
<221> NAME/KEY: CDS
<222> LOCATION: (464)..(1885)

<400> SEQUENCE: 19

```
gatccttttt aacccatcac atatacctgc cgttcactat tatttagtga aatgagatat     60
tatgatattt tctgaattgt gattaaaaag gcaactttat gcccatgcaa cagaaactat    120
aaaaaataca gagaatgaaa agaaacagat agatttttta gttctttagg cccgtagtct    180
gcaaatcctt ttatgatttt ctatcaaaca aagaggaaaa atagaccagt tgcaatccaa    240
acgagagtct aatagaatga ggtcgaaaag taaatcgcgc gggtttgtta ctgataaagc    300
aggcaagacc taaatgtgt aaagggcaaa gtgtatactt tggcgtcacc ccttacatat     360
tttaggtctt ttttattgt gcgtaactaa cttgccatct tcaaacagga gggctggaag     420
aagcagaccg ctaacacagt acataaaaaa ggagacatga cg atg aac atc aaa       475
                                                Met Asn Ile Lys
                                                 1 aag ttt gca aaa caa gca aca gta tta acc ttt act acc gca ctg ctg     523
Lys Phe Ala Lys Gln Ala Thr Val Leu Thr Phe Thr Thr Ala Leu Leu
 5                  10                  15                  20 gca gga ggc gca act caa gcg ttt gcg aaa gaa acg aac caa aag cca     571
Ala Gly Gly Ala Thr Gln Ala Phe Ala Lys Glu Thr Asn Gln Lys Pro
                25                  30                  35 tat aag gaa aca tac ggc att tcc cat att aca cgc cat gat atg ctg     619
```

```
                    Tyr Lys Glu Thr Tyr Gly Ile Ser His Ile Thr Arg His Asp Met Leu
                                40                  45                  50 caa atc cct gaa cag caa aaa aat gaa aaa tat caa gtt cct gaa ttc                667
Gln Ile Pro Glu Gln Gln Lys Asn Glu Lys Tyr Gln Val Pro Glu Phe
        55                  60                  65 gat tcg tcc aca att aaa aat atc tct tct gca aaa ggc ctg gac gtt                715
Asp Ser Ser Thr Ile Lys Asn Ile Ser Ser Ala Lys Gly Leu Asp Val
    70                  75                  80 tgg gac agc tgg cca tta caa aac gct gac ggc act gtc gca aac tat                763
Trp Asp Ser Trp Pro Leu Gln Asn Ala Asp Gly Thr Val Ala Asn Tyr
 85                  90                  95                 100 cac ggc tac cac atc gtc ttt gca tta gcc gga gat cct aaa aat gcg                811
His Gly Tyr His Ile Val Phe Ala Leu Ala Gly Asp Pro Lys Asn Ala
                105                 110                 115 gat gac aca tcg att tac atg ttc tat caa aaa gtc ggc gaa act tct                859
Asp Asp Thr Ser Ile Tyr Met Phe Tyr Gln Lys Val Gly Glu Thr Ser
        120                 125                 130 att gac agc tgg aaa aac gct ggc cgc gtc ttt aaa gac agc gac aaa                907
Ile Asp Ser Trp Lys Asn Ala Gly Arg Val Phe Lys Asp Ser Asp Lys
    135                 140                 145 ttc gat gca aat gat tct atc cta aaa gac caa aca caa gaa tgg tca                955
Phe Asp Ala Asn Asp Ser Ile Leu Lys Asp Gln Thr Gln Glu Trp Ser
150                 155                 160 ggt tca gcc aca ttt aca tct gac gga aaa atc cgt tta ttc tac act               1003
Gly Ser Ala Thr Phe Thr Ser Asp Gly Lys Ile Arg Leu Phe Tyr Thr
165                 170                 175                 180 gat ttc tcc ggt aaa cat tac ggc aaa caa aca ctg aca act gca caa               1051
Asp Phe Ser Gly Lys His Tyr Gly Lys Gln Thr Leu Thr Thr Ala Gln
                185                 190                 195 gtt aac gta tca gca tca gac agc tct ttg aac atc aac ggt gta gag               1099
Val Asn Val Ser Ala Ser Asp Ser Ser Leu Asn Ile Asn Gly Val Glu
        200                 205                 210 gat tat aaa tca atc ttt gac ggt gac gga aaa acg tat caa aat gta               1147
Asp Tyr Lys Ser Ile Phe Asp Gly Asp Gly Lys Thr Tyr Gln Asn Val
    215                 220                 225 cag cag ttc atc gat gaa ggc aac tac agc tca ggc gac aac cat acg               1195
Gln Gln Phe Ile Asp Glu Gly Asn Tyr Ser Ser Gly Asp Asn His Thr
230                 235                 240 ctg aga gat cct cac tac gta gaa gat aaa ggc cac aaa tac tta gta               1243
Leu Arg Asp Pro His Tyr Val Glu Asp Lys Gly His Lys Tyr Leu Val
245                 250                 255                 260 ttt gaa gca aac act gga act gaa gat ggc tac caa ggc gaa gaa tct               1291
Phe Glu Ala Asn Thr Gly Thr Glu Asp Gly Tyr Gln Gly Glu Glu Ser
                265                 270                 275 tta ttt aac aaa gca tac tat ggc aaa agc aca tca ttc ttc cgt caa               1339
Leu Phe Asn Lys Ala Tyr Tyr Gly Lys Ser Thr Ser Phe Phe Arg Gln
        280                 285                 290 gaa agt caa aaa ctt ctg caa agc gat aaa aaa cgc acg gct gag tta               1387
Glu Ser Gln Lys Leu Leu Gln Ser Asp Lys Lys Arg Thr Ala Glu Leu
    295                 300                 305 gca aac ggc gct ctc ggt atg att gag cta aac gat gat tac aca ctg               1435
Ala Asn Gly Ala Leu Gly Met Ile Glu Leu Asn Asp Asp Tyr Thr Leu
310                 315                 320 aaa aaa gtg atg aaa ccg ctg att gca tct aac aca gta aca gat gaa               1483
Lys Lys Val Met Lys Pro Leu Ile Ala Ser Asn Thr Val Thr Asp Glu
325                 330                 335                 340 att gaa cgc gcg aac gtc ttt aaa atg aac ggc aaa tgg tac ctg ttc               1531
Ile Glu Arg Ala Asn Val Phe Lys Met Asn Gly Lys Trp Tyr Leu Phe
                345                 350                 355
```

```
act gac tcc cgc gga tca aaa atg acg att gac ggc att acg tct aac    1579
Thr Asp Ser Arg Gly Ser Lys Met Thr Ile Asp Gly Ile Thr Ser Asn
        360                 365                 370 gat att tac atg ctt ggt tat gtt tct aat tct tta act ggc cca tac    1627
Asp Ile Tyr Met Leu Gly Tyr Val Ser Asn Ser Leu Thr Gly Pro Tyr
            375                 380                 385 aag ccg ctg aac aaa act ggc ctt gtg tta aaa atg gat ctt gat cct    1675
Lys Pro Leu Asn Lys Thr Gly Leu Val Leu Lys Met Asp Leu Asp Pro
390                 395                 400 aac gat gta acc ttt act tac tca cac ttc gct gta cct caa gcg aaa    1723
Asn Asp Val Thr Phe Thr Tyr Ser His Phe Ala Val Pro Gln Ala Lys
405                 410                 415                 420 gga aac aat gtc gtg att aca agc tat atg aca aac aga gga ttc tac    1771
Gly Asn Asn Val Val Ile Thr Ser Tyr Met Thr Asn Arg Gly Phe Tyr
                425                 430                 435 gca gac aaa caa tca acg ttt gcg cca agc ttc ctg ctg aac atc aaa    1819
Ala Asp Lys Gln Ser Thr Phe Ala Pro Ser Phe Leu Leu Asn Ile Lys
                440                 445                 450 ggc aag aaa aca tct gtt gtc aaa gac agc atc ctt gaa caa gga caa    1867
Gly Lys Lys Thr Ser Val Val Lys Asp Ser Ile Leu Glu Gln Gly Gln
                455                 460                 465 tta aca gtt aac aaa taa aaacgcaaaa gaaaatgccg atatcctatt          1915
Leu Thr Val Asn Lys
        470 ggcattttct tttatttctt atcaacataa aggtgaatcc catatgaact atataaaagc  1975 aggcaaatgg ctaaccgtat tcctaacctt ttgaagatc                         2014

<210> SEQ ID NO 20
<211> LENGTH: 473
<212> TYPE: PRT
<213> ORGANISM: Bacillus subtilis

<400> SEQUENCE: 20

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190
```

```
Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 21
<211> LENGTH: 24
<212> TYPE: DNA
<213> ORGANISM: Artificial sequence
<220> FEATURE:
<223> OTHER INFORMATION: primer

<400> SEQUENCE: 21
cgggatcctt tttaacccat caca                                          24

<210> SEQ ID NO 22
<211> LENGTH: 29
<212> TYPE: DNA
<213> ORGANISM: Artificial sequence
<220> FEATURE:
<223> OTHER INFORMATION: primer

<400> SEQUENCE: 22
gaagatcttc aaaaggttag gaatacggt                                     29
```

```
<210> SEQ ID NO 23
<211> LENGTH: 23
<212> TYPE: DNA
<213> ORGANISM: Artificial sequence
<220> FEATURE:
<223> OTHER INFORMATION: primer

<400> SEQUENCE: 23 cctttttgaag atcgaccagt tgg                                            23

<210> SEQ ID NO 24
<211> LENGTH: 44
<212> TYPE: DNA
<213> ORGANISM: Artificial sequence
<220> FEATURE:
<223> OTHER INFORMATION: primer

<400> SEQUENCE: 24
tacctggaat gctgttttcc cagggatcgc agtggtgagt aacc                      44

<210> SEQ ID NO 25
<211> LENGTH: 28
<212> TYPE: DNA
<213> ORGANISM: Artificial sequence
<220> FEATURE:
<223> OTHER INFORMATION: primer

<400> SEQUENCE: 25
cctgggaaaa cagcattcca ggtattag                                        28

<210> SEQ ID NO 26
<211> LENGTH: 23
<212> TYPE: DNA
<213> ORGANISM: Artificial sequence
<220> FEATURE:
<223> OTHER INFORMATION: primer

<400> SEQUENCE: 26
tgcaggtcga ctctagagga tcc                                             23

<210> SEQ ID NO 27
<211> LENGTH: 2028
<212> TYPE: DNA
<213> ORGANISM: Corynebacterium glutamicum
<220> FEATURE:
<221> NAME/KEY: CDS
<222> LOCATION: (1)..(2028)

<400> SEQUENCE: 27
```

| | | | | | | | | | | | | | | | | |
|---|---|---|---|---|---|---|---|---|---|---|---|---|---|---|---|---|
| atg | gcg | ttc | tcc | gta | gag | atg | ccc | gag | ctg | ggc | gaa | tca | gta | acc | gaa | 48 |
| Met | Ala | Phe | Ser | Val | Glu | Met | Pro | Glu | Leu | Gly | Glu | Ser | Val | Thr | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | acg | atc | acc | cag | tgg | ttg | aag | tct | gtt | ggt | gac | act | gtt | gag | gta | 96 |
| Gly | Thr | Ile | Thr | Gln | Trp | Leu | Lys | Ser | Val | Gly | Asp | Thr | Val | Glu | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gag | ccg | ttg | ctc | gag | gtc | tca | act | gac | aag | gtc | gac | acc | gag | att | 144 |
| Asp | Glu | Pro | Leu | Leu | Glu | Val | Ser | Thr | Asp | Lys | Val | Asp | Thr | Glu | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| ccc | tct | cct | gtc | gcc | ggt | gtc | atc | cta | gag | att | aag | gct | gaa | gag | gat | 192 |
| Pro | Ser | Pro | Val | Ala | Gly | Val | Ile | Leu | Glu | Ile | Lys | Ala | Glu | Glu | Asp | |
| 50 | | | | | 55 | | | | | 60 | | | | | | |

| | | | | | | | | | | | | | | | | |
|---|---|---|---|---|---|---|---|---|---|---|---|---|---|---|---|---|
| gac | acc | gtc | gac | gtc | ggc | ggt | gtc | att | gca | ata | atc | ggc | gat | gct | gat | 240 |
| Asp | Thr | Val | Asp | Val | Gly | Gly | Val | Ile | Ala | Ile | Ile | Gly | Asp | Ala | Asp | |
| 65 | | | | | 70 | | | | | 75 | | | | | 80 | |

-continued

| | | |
|---|---|---|
| gag act cct gcc aac gaa gct cct gcc gac gag gca cca gct cct gcc<br>Glu Thr Pro Ala Asn Glu Ala Pro Ala Asp Glu Ala Pro Ala Pro Ala<br>85 90 95 | 288 |
| gaa gag gaa gaa cca gtt aag gaa gag cca aag aag gag gca gct cct<br>Glu Glu Glu Glu Pro Val Lys Glu Glu Pro Lys Lys Glu Ala Ala Pro<br>100 105 110 | 336 |
| gaa gct cca gca gca act ggc gcc gca acc gat gtg gaa atg cca gaa<br>Glu Ala Pro Ala Ala Thr Gly Ala Ala Thr Asp Val Glu Met Pro Glu<br>115 120 125 | 384 |
| ctc ggc gaa tcc gtc acc gaa ggc acc att acc cag tgg ctc aag gct<br>Leu Gly Glu Ser Val Thr Glu Gly Thr Ile Thr Gln Trp Leu Lys Ala<br>130 135 140 | 432 |
| gtc ggc gac acc gtc gaa gta gac gaa cca ctt ctt gag gtc tcc acc<br>Val Gly Asp Thr Val Glu Val Asp Glu Pro Leu Leu Glu Val Ser Thr<br>145 150 155 160 | 480 |
| gac aag gtc gac acc gaa atc cca tcc cca gta gca ggc acc atc gtg<br>Asp Lys Val Asp Thr Glu Ile Pro Ser Pro Val Ala Gly Thr Ile Val<br>165 170 175 | 528 |
| gag atc ctt gca gac gaa gac gac acc gtc gac gtc ggc gca gtc atc<br>Glu Ile Leu Ala Asp Glu Asp Asp Thr Val Asp Val Gly Ala Val Ile<br>180 185 190 | 576 |
| gcc cgc atc ggt gac gca aac gca gct gca gca cct gcc gaa gag gaa<br>Ala Arg Ile Gly Asp Ala Asn Ala Ala Ala Ala Pro Ala Glu Glu Glu<br>195 200 205 | 624 |
| gca gct cct gcc gaa gag gaa gaa cca gtt aag gaa gag cca aag aag<br>Ala Ala Pro Ala Glu Glu Glu Glu Pro Val Lys Glu Glu Pro Lys Lys<br>210 215 220 | 672 |
| gag gca gct cct gaa gct cca gca gca act ggc gcc gca acc gat gtg<br>Glu Ala Ala Pro Glu Ala Pro Ala Ala Thr Gly Ala Ala Thr Asp Val<br>225 230 235 240 | 720 |
| gaa atg cca gaa ctc ggc gaa tcc gtc acc gaa ggc acc att acc cag<br>Glu Met Pro Glu Leu Gly Glu Ser Val Thr Glu Gly Thr Ile Thr Gln<br>245 250 255 | 768 |
| tgg ctc aag gct gtc ggc gac acc gtc gaa gta gac gaa cca ctt ctt<br>Trp Leu Lys Ala Val Gly Asp Thr Val Glu Val Asp Glu Pro Leu Leu<br>260 265 270 | 816 |
| gag gtc tcc acc gac aag gtc gac acc gaa atc cca tcc cca gta gca<br>Glu Val Ser Thr Asp Lys Val Asp Thr Glu Ile Pro Ser Pro Val Ala<br>275 280 285 | 864 |
| ggc acc atc gtg gag atc ctt gca gac gaa gac gac acc gtc gac gtc<br>Gly Thr Ile Val Glu Ile Leu Ala Asp Glu Asp Asp Thr Val Asp Val<br>290 295 300 | 912 |
| ggc gca gtc atc gcc cgc atc ggt gac gca aac gca gct gca gca cct<br>Gly Ala Val Ile Ala Arg Ile Gly Asp Ala Asn Ala Ala Ala Ala Pro<br>305 310 315 320 | 960 |
| gcc gaa gag gaa gca gct cct gcc gaa gag gag gaa cca gtt aag gaa<br>Ala Glu Glu Glu Ala Ala Pro Ala Glu Glu Glu Pro Val Lys Glu<br>325 330 335 | 1008 |
| gag cca aag aag gaa gag ccc aag aag gaa gag ccc aag aag gaa gca<br>Glu Pro Lys Lys Glu Glu Pro Lys Lys Glu Glu Pro Lys Lys Glu Ala<br>340 345 350 | 1056 |
| gct act aca cct gct gcg gca tcc gca act gtg tcc gct tct ggc gac<br>Ala Thr Thr Pro Ala Ala Ala Ser Ala Thr Val Ser Ala Ser Gly Asp<br>355 360 365 | 1104 |
| aac gtt cca tac gtc acc cca ctg gtg cgc aag ctt gct gaa aag cac<br>Asn Val Pro Tyr Val Thr Pro Leu Val Arg Lys Leu Ala Glu Lys His<br>370 375 380 | 1152 |
| ggc gtt gac ttg aac acc gtg acc ggt acc ggt atc ggt ggc cgt atc<br>Gly Val Asp Leu Asn Thr Val Thr Gly Thr Gly Ile Gly Gly Arg Ile<br>385 390 395 400 | 1200 |

-continued

```
cgc aag cag gat gtt ttg gct gct gcg aac ggc gag gct gca cct gct    1248
Arg Lys Gln Asp Val Leu Ala Ala Ala Asn Gly Glu Ala Ala Pro Ala
            405                 410                 415 gag gct gct gct cct gtt tcc gct tgg tcc act aag tct gtt gac cct    1296
Glu Ala Ala Ala Pro Val Ser Ala Trp Ser Thr Lys Ser Val Asp Pro
        420                 425                 430 gag aag gct aag ctc cgt ggt acc act cag aag gtc aac cgc atc cgt    1344
Glu Lys Ala Lys Leu Arg Gly Thr Thr Gln Lys Val Asn Arg Ile Arg
    435                 440                 445 gag atc acc gcg atg aag acc gtc gag gct ctg cag att tct gct cag    1392
Glu Ile Thr Ala Met Lys Thr Val Glu Ala Leu Gln Ile Ser Ala Gln
450                 455                 460 ctc acc cag ctg cac gag gtc gat atg act cgc gtt gct gag ctg cgt    1440
Leu Thr Gln Leu His Glu Val Asp Met Thr Arg Val Ala Glu Leu Arg
465                 470                 475                 480 aag aag aac aag ccc gcg ttc atc gag aag cac ggt gtg aac ctc act    1488
Lys Lys Asn Lys Pro Ala Phe Ile Glu Lys His Gly Val Asn Leu Thr
                485                 490                 495 tac ctg cca ttc ttc gtg aag gca gtt gtc gag gct ttg gtt tcc cat    1536
Tyr Leu Pro Phe Phe Val Lys Ala Val Val Glu Ala Leu Val Ser His
            500                 505                 510 cca aac gtc aac gcg tct ttc aac gcg aag acc aag gag atg acc tac    1584
Pro Asn Val Asn Ala Ser Phe Asn Ala Lys Thr Lys Glu Met Thr Tyr
        515                 520                 525 cac tcc tcc gtt aac ctc tcc atc gct gtt gat acc cca gct ggt ctg    1632
His Ser Ser Val Asn Leu Ser Ile Ala Val Asp Thr Pro Ala Gly Leu
    530                 535                 540 ttg acc cca gtc att cac gat gct cag gat ctc tcc atc cca gag atc    1680
Leu Thr Pro Val Ile His Asp Ala Gln Asp Leu Ser Ile Pro Glu Ile
545                 550                 555                 560 gca aag gca att gtt gac ctg gct gat cgt tca cgc aac aac aag ctg    1728
Ala Lys Ala Ile Val Asp Leu Ala Asp Arg Ser Arg Asn Asn Lys Leu
                565                 570                 575 aag cca aac gat ctg tcc ggt ggc acc ttc acc atc acc aac att ggt    1776
Lys Pro Asn Asp Leu Ser Gly Gly Thr Phe Thr Ile Thr Asn Ile Gly
            580                 585                 590 tct gaa ggc gca ctg tct gat acc cca atc ctg gtt cca cca cag gct    1824
Ser Glu Gly Ala Leu Ser Asp Thr Pro Ile Leu Val Pro Pro Gln Ala
        595                 600                 605 ggc atc ttg ggc acc ggc gcg atc gtg aag cgt cca gtt gtc atc acc    1872
Gly Ile Leu Gly Thr Gly Ala Ile Val Lys Arg Pro Val Val Ile Thr
    610                 615                 620 gag gat gga att gat tcc atc gcg atc cgt cag atg gtc ttc cta cca    1920
Glu Asp Gly Ile Asp Ser Ile Ala Ile Arg Gln Met Val Phe Leu Pro
625                 630                 635                 640 ctg acc tac gac cac cag gtt gta gat ggc gca gat gct ggt cgc ttc    1968
Leu Thr Tyr Asp His Gln Val Val Asp Gly Ala Asp Ala Gly Arg Phe
                645                 650                 655 ctg acc acc atc aag gac cgc ctt gag acc gct aac ttc gaa ggc gat    2016
Leu Thr Thr Ile Lys Asp Arg Leu Glu Thr Ala Asn Phe Glu Gly Asp
            660                 665                 670 ctg cag ctc taa                                                    2028
Leu Gln Leu
        675

<210> SEQ ID NO 28
<211> LENGTH: 675
<212> TYPE: PRT
<213> ORGANISM: Corynebacterium glutamicum
```

<400> SEQUENCE: 28

| | | | | | | | | | | | | | | |
|---|---|---|---|---|---|---|---|---|---|---|---|---|---|---|
|Met|Ala|Phe|Ser|Val|Glu|Met|Pro|Glu|Leu|Gly|Glu|Ser|Val|Thr|Glu|
|1| | | |5| | | | |10| | | | |15| |

Gly Thr Ile Thr Gln Trp Leu Lys Ser Val Gly Asp Thr Val Glu Val
            20                25                30

Asp Glu Pro Leu Leu Glu Val Ser Thr Asp Lys Val Asp Thr Glu Ile
            35                40                45

Pro Ser Pro Val Ala Gly Val Ile Leu Glu Ile Lys Ala Glu Glu Asp
    50                55                60

Asp Thr Val Asp Val Gly Gly Val Ile Ala Ile Gly Asp Ala Asp
65                70                75              80

Glu Thr Pro Ala Asn Glu Ala Pro Ala Asp Glu Ala Pro Ala Pro Ala
            85                90                95

Glu Glu Glu Glu Pro Val Lys Glu Glu Pro Lys Lys Glu Ala Ala Pro
            100              105              110

Glu Ala Pro Ala Ala Thr Gly Ala Thr Asp Val Glu Met Pro Glu
            115              120              125

Leu Gly Glu Ser Val Thr Glu Gly Thr Ile Thr Gln Trp Leu Lys Ala
130                135                140

Val Gly Asp Thr Val Glu Val Asp Glu Pro Leu Leu Glu Val Ser Thr
145                150              155              160

Asp Lys Val Asp Thr Glu Ile Pro Ser Pro Val Ala Gly Thr Ile Val
            165              170              175

Glu Ile Leu Ala Asp Glu Asp Thr Val Asp Val Gly Ala Val Ile
            180              185              190

Ala Arg Ile Gly Asp Ala Asn Ala Ala Ala Pro Ala Glu Glu Glu
            195              200              205

Ala Ala Pro Ala Glu Glu Glu Pro Val Lys Glu Pro Lys Lys
            210              215              220

Glu Ala Ala Pro Glu Ala Pro Ala Ala Thr Gly Ala Ala Thr Asp Val
225                230              235              240

Glu Met Pro Glu Leu Gly Glu Ser Val Thr Glu Gly Thr Ile Thr Gln
            245              250              255

Trp Leu Lys Ala Val Gly Asp Thr Val Glu Val Asp Glu Pro Leu Leu
            260              265              270

Glu Val Ser Thr Asp Lys Val Asp Thr Glu Ile Pro Ser Pro Val Ala
            275              280              285

Gly Thr Ile Val Glu Ile Leu Ala Asp Glu Asp Thr Val Asp Val
            290              295              300

Gly Ala Val Ile Ala Arg Ile Gly Asp Ala Asn Ala Ala Ala Pro
305                310              315              320

Ala Glu Glu Glu Ala Ala Pro Ala Glu Glu Glu Pro Val Lys Glu
            325              330              335

Glu Pro Lys Lys Glu Pro Lys Lys Glu Pro Lys Lys Glu Ala
            340              345              350

Ala Thr Thr Pro Ala Ala Ser Ala Thr Val Ser Ala Ser Gly Asp
            355              360              365

Asn Val Pro Tyr Val Thr Pro Leu Val Arg Lys Leu Ala Glu Lys His
            370              375              380

Gly Val Asp Leu Asn Thr Val Thr Gly Thr Gly Ile Gly Gly Arg Ile
385                390              395              400

Arg Lys Gln Asp Val Leu Ala Ala Asn Gly Glu Ala Ala Pro Ala
            405              410              415

```
Glu Ala Ala Ala Pro Val Ser Ala Trp Ser Thr Lys Ser Val Asp Pro
            420                 425                 430

Glu Lys Ala Lys Leu Arg Gly Thr Thr Gln Lys Val Asn Arg Ile Arg
            435                 440                 445

Glu Ile Thr Ala Met Lys Thr Val Glu Ala Leu Gln Ile Ser Ala Gln
            450                 455                 460

Leu Thr Gln Leu His Glu Val Asp Met Thr Arg Val Ala Glu Leu Arg
465                 470                 475                 480

Lys Lys Asn Lys Pro Ala Phe Ile Glu Lys His Gly Val Asn Leu Thr
            485                 490                 495

Tyr Leu Pro Phe Phe Val Lys Ala Val Val Glu Ala Leu Val Ser His
            500                 505                 510

Pro Asn Val Asn Ala Ser Phe Asn Ala Lys Thr Lys Glu Met Thr Tyr
            515                 520                 525

His Ser Ser Val Asn Leu Ser Ile Ala Val Asp Thr Pro Ala Gly Leu
            530                 535                 540

Leu Thr Pro Val Ile His Asp Ala Gln Asp Leu Ser Ile Pro Glu Ile
545                 550                 555                 560

Ala Lys Ala Ile Val Asp Leu Ala Asp Arg Ser Arg Asn Asn Lys Leu
            565                 570                 575

Lys Pro Asn Asp Leu Ser Gly Gly Thr Phe Thr Ile Thr Asn Ile Gly
            580                 585                 590

Ser Glu Gly Ala Leu Ser Asp Thr Pro Ile Leu Val Pro Pro Gln Ala
            595                 600                 605

Gly Ile Leu Gly Thr Gly Ala Ile Val Lys Arg Pro Val Val Ile Thr
            610                 615                 620

Glu Asp Gly Ile Asp Ser Ile Ala Ile Arg Gln Met Val Phe Leu Pro
625                 630                 635                 640

Leu Thr Tyr Asp His Gln Val Val Asp Gly Ala Asp Ala Gly Arg Phe
            645                 650                 655

Leu Thr Thr Ile Lys Asp Arg Leu Glu Thr Ala Asn Phe Glu Gly Asp
            660                 665                 670

Leu Gln Leu
    675

<210> SEQ ID NO 29
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)
<223> OTHER INFORMATION: yggB

<400> SEQUENCE: 29
gatcttgccg atttcggcag gatcaatgtc ggcgtgaatg atcttggcat caggtgcgaa      60
agtgtcaacg tcaccggtga cgcggtcatc aaagcgggag ccgatagcaa tcagcaggtc     120
gctgcgctgc agtgcaccaa cagcggacac agtgccatgc atgcctggca tacccatgtg     180
cagctcgtgg gactctggga aggttcccag cgccatcaat gtggtgacaa ctggaatgcc     240
ggtgtgctca gcgaacgcac gaagctcttc gtgggcatca gccttgataa cgccgccgcc     300
aacgtaaagg acaggcttct tagactcacc gatcagtttg acagcctgct caatctgtcg     360
agcatgcggt gttgaaactg gcggtagcc tggcaggtcg atctttggtg ccagacgaa      420 atccaattca gcgttctgaa catccttggg gatatccact agaacaggac cagggcgacc     480
```

-continued

```
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg gccggtgatg caaccatgg gaacggagtc     660 caagtttgca tcagcgattg ggtaaccaa gttggttgcg cctgggccag aggttgcaat     720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc aggggcggcg gatcgaccac ggcttgcaac    960
cgtggcggga gtgggctgtt gagaagctgc cacattcacg actttctggc tcctttacta   1020
aataaggatt ttcacaggac ccgtccaagc caagccgatt tcaactcagc ctaaagacaa   1080
agccctcatt taaaattgtt ccgacgcgga tgcgtgtgca cgcagtgcga cagatgtctg   1140
ttgcaaagtt ggctacttgg gtcataacca acaagaaagc cctcgttcca acactgtggt   1200
gagtgttgtc gagggcgctt gacgagacga cttggaaggc cgttacggca ggcgccgcgc   1260
ggttactact acaagtcgaa taatggtcat ggtgtgtcat gctacacaca tcgagtttcc   1320
aattccacaa cgcacgaaaa ttcccacccc caaaactccc ccacttcggt taaggaatca   1380
ggattctcac aaagttcagg caggctcccg ctacttttca gcgctaatct tggctc atg   1439
                                                                Met
                                                                 1 att tta ggc gta ccc att caa tat ttg ctc tat tca ttg tgg aat tgg    1487
Ile Leu Gly Val Pro Ile Gln Tyr Leu Leu Tyr Ser Leu Trp Asn Trp
        5                   10                  15 att gtc gat acc ggt ttt gat gta gca att atc ctg gtc ttg gcg ttt    1535
Ile Val Asp Thr Gly Phe Asp Val Ala Ile Ile Leu Val Leu Ala Phe
20                  25                  30 ttg att cca cgt atc ggc cga ctg gcc atg cgt att atc aag cag cga    1583
Leu Ile Pro Arg Ile Gly Arg Leu Ala Met Arg Ile Ile Lys Gln Arg
            35                  40                  45 gtg gag tct gca gcc gat gcg gac acc act aag aac cag ctc gcg ttc    1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt    1679
Ala Gly Val Gly Val Tyr Ile Ala Gln Ile Val Ala Phe Phe Met Leu
                70                  75                  80 gcc gtc tcc gcg atg cag gct ttt ggt ttc tct ctc gcg ggc gct gcg    1727
Ala Val Ser Ala Met Gln Ala Phe Gly Phe Ser Leu Ala Gly Ala Ala
            85                  90                  95 att ccg gca acc att gcg tca gct gcc att ggt ctt ggt gcg cag tcg    1775
Ile Pro Ala Thr Ile Ala Ser Ala Ala Ile Gly Leu Gly Ala Gln Ser
        100                 105                 110 att gtt gcg gac ttc ttg gcc gga ttt ttc atc ctg acg gaa aag caa    1823
Ile Val Ala Asp Phe Leu Ala Gly Phe Phe Ile Leu Thr Glu Lys Gln
    115                 120                 125 ttc ggc gtg ggt gac tgg gtg cgc ttt gag ggc aac ggc atc gtt gtt    1871
Phe Gly Val Gly Asp Trp Val Arg Phe Glu Gly Asn Gly Ile Val Val
130                 135                 140                 145 gaa ggc acc gtc att gag atc acc atg cgc gcg acc aaa att cgc acg    1919
Glu Gly Thr Val Ile Glu Ile Thr Met Arg Ala Thr Lys Ile Arg Thr
                150                 155                 160 att gca caa gag acc gtg atc atc ccg aac tcc acg gcg aaa gtg tgc    1967
Ile Ala Gln Glu Thr Val Ile Ile Pro Asn Ser Thr Ala Lys Val Cys
            165                 170                 175
```

-continued

| | | |
|---|---|---|
| atc aac aat tct aat aac tgg tcg cgt gcg gtt gtc gtt att ccg atc<br>Ile Asn Asn Ser Asn Asn Trp Ser Arg Ala Val Val Val Ile Pro Ile<br>     180                   185                 190 | | 2015 |
| ccc atg ttg ggt tct gaa aac atc aca gat gtc atc gcg cgc tct gaa<br>Pro Met Leu Gly Ser Glu Asn Ile Thr Asp Val Ile Ala Arg Ser Glu<br>195                   200                 205 | | 2063 |
| gct gcg act cgt cgc gca ctt ggc cag gag aaa atc gca ccg gaa atc<br>Ala Ala Thr Arg Arg Ala Leu Gly Gln Glu Lys Ile Ala Pro Glu Ile<br>210                 215               220               225 | | 2111 |
| ctc ggt gaa ctc gat gtg cac cca gcc acg gaa gtc aca ccg cca acg<br>Leu Gly Glu Leu Asp Val His Pro Ala Thr Glu Val Thr Pro Pro Thr<br>               230                 235               240 | | 2159 |
| gtg gtc ggc atg ccg tgg atg gtc acc atg cgt ttc ctc gtg caa gtc<br>Val Val Gly Met Pro Trp Met Val Thr Met Arg Phe Leu Val Gln Val<br>               245                 250               255 | | 2207 |
| acc gcc ggc aat caa tgg ctg gtc gaa cgc gcc atc cgc aca gaa atc<br>Thr Ala Gly Asn Gln Trp Leu Val Glu Arg Ala Ile Arg Thr Glu Ile<br>260                   265                 270 | | 2255 |
| atc aac gaa ttc tgg gaa gaa tac ggc agc gca acc act aca tcg gga<br>Ile Asn Glu Phe Trp Glu Glu Tyr Gly Ser Ala Thr Thr Thr Ser Gly<br>               275                 280               285 | | 2303 |
| acc ctc att gat tcc tta cac gtt gag cat gaa gag cca aag acc tcg<br>Thr Leu Ile Asp Ser Leu His Val Glu His Glu Glu Pro Lys Thr Ser<br>290                   295                 300               305 | | 2351 |
| ctt atc gac gcc tcc ccc cag gct ctt aag gaa ccg aag ccg gag gct<br>Leu Ile Asp Ala Ser Pro Gln Ala Leu Lys Glu Pro Lys Pro Glu Ala<br>               310                 315               320 | | 2399 |
| gcg gcg acg gtt gca tcg cta gct gca tcg tct aac gac gat gca gac<br>Ala Ala Thr Val Ala Ser Leu Ala Ala Ser Ser Asn Asp Asp Ala Asp<br>               325                 330               335 | | 2447 |
| aat gca gac gcc tcg gcg atc aat gca ggc aat cca gag aag gaa ctt<br>Asn Ala Asp Ala Ser Ala Ile Asn Ala Gly Asn Pro Glu Lys Glu Leu<br>340                   345                 350 | | 2495 |
| gat tcc gat gtg ctg gaa caa gaa ctc tcc agc gaa gaa ccg gaa gaa<br>Asp Ser Asp Val Leu Glu Gln Glu Leu Ser Ser Glu Glu Pro Glu Glu<br>               355                 360               365 | | 2543 |
| aca gca aaa cca gat cac tct ctc cga ggc ttc ttc cgc act gat tac<br>Thr Ala Lys Pro Asp His Ser Leu Arg Gly Phe Phe Arg Thr Asp Tyr<br>370                   375                 380               385 | | 2591 |
| tac cca aat cgg tgg cag aag atc ctg tcg ttt ggc gga cgt gtc cgc<br>Tyr Pro Asn Arg Trp Gln Lys Ile Leu Ser Phe Gly Gly Arg Val Arg<br>               390                 395               400 | | 2639 |
| atg agc act tcc ctg ttg ttg ggt gcg ctg ctc ttg ctg tca cta ttt<br>Met Ser Thr Ser Leu Leu Leu Gly Ala Leu Leu Leu Leu Ser Leu Phe<br>               405                 410               415 | | 2687 |
| aag gtc atg act gtg gaa cca agt gag aat tgg caa aac tcc agt gga<br>Lys Val Met Thr Val Glu Pro Ser Glu Asn Trp Gln Asn Ser Ser Gly<br>420                   425                 430 | | 2735 |
| tgg ctg tca cca agc act gcc acc tca act gcg gtg acc acc tcc gaa<br>Trp Leu Ser Pro Ser Thr Ala Thr Ser Thr Ala Val Thr Thr Ser Glu<br>               435                 440               445 | | 2783 |
| act tcc gcg cca gca agc acg cct tcg atg aca gtg ccc act acg gtg<br>Thr Ser Ala Pro Ala Ser Thr Pro Ser Met Thr Val Pro Thr Thr Val<br>450                   455                 460               465 | | 2831 |
| gag gag acc cca acg atg gaa tct agc gtc gaa acg cag cag gaa acc<br>Glu Glu Thr Pro Thr Met Glu Ser Ser Val Glu Thr Gln Gln Glu Thr<br>               470                 475               480 | | 2879 |
| tca acc cct gca acc gca acg ccc cag cga gcc gac acc atc gaa ccg<br>Ser Thr Pro Ala Thr Ala Thr Pro Gln Arg Ala Asp Thr Ile Glu Pro<br>               485                 490               495 | | 2927 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| acc | gag | gaa | gcc | acg | tcg | cag | gag | gaa | acg | act | gca | tcg | cag | acg | cag | 2975 |
| Thr | Glu | Glu | Ala | Thr | Ser | Gln | Glu | Glu | Thr | Thr | Ala | Ser | Gln | Thr | Gln |      |
|     |     |     | 500 |     |     |     |     | 505 |     |     |     |     | 510 |     |     |      |
| tct | cca | gca | gtg | gaa | gca | cca | acc | gcg | gtc | caa | gaa | aca | gtt | gcg | ccg | 3023 |
| Ser | Pro | Ala | Val | Glu | Ala | Pro | Thr | Ala | Val | Gln | Glu | Thr | Val | Ala | Pro |      |
|     | 515 |     |     |     |     | 520 |     |     |     |     | 525 |     |     |     |     |      |
| acg | tcc | acc | cct | taggacgctg | attacagacg | tgtcccattt | ctttactact | | | | | | | | | 3075 |
| Thr | Ser | Thr | Pro |            |            |            |            | | | | | | | | |      |
| 530 |     |     |     |            |            |            |            | | | | | | | | |      | attggaaatt atgagttcag acgcagaaaa ggcatccgtg agctttccg aaaaatttca  3135 cccagaacgc acccatattt tgggcgccgt tgtttttggc ctgatctcat tattagtcat  3195 cggcgcagcc cctcagtacc tgttttggct gctcgcgctc cctgtcatct tcggttactg  3255 ggttctaaaa tcatccacga tcgttgatga acagggcatc accgcaaact acgccttcaa  3315 gggcaaaaag gttgtggcct gggaagacct cgcaggaatc ggattcaagg gtgcccgcac  3375 tttcgctcgc accacctccg atgcagaagt caccctcccc ggcgtcacct tcaactccct  3435 tccccgcctt gaagctgctt cccacggccg catccccgat gcgatc  3481

<210> SEQ ID NO 30
<211> LENGTH: 533
<212> TYPE: PRT
<213> ORGANISM: Corynebacterium glutamicum

<400> SEQUENCE: 30

| Met | Ile | Leu | Gly | Val | Pro | Ile | Gln | Tyr | Leu | Leu | Tyr | Ser | Leu | Trp | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Trp | Ile | Val | Asp | Thr | Gly | Phe | Asp | Val | Ala | Ile | Ile | Leu | Val | Leu | Ala |
|-----|-----|-----|-----|-----|-----|-----|-----|-----|-----|-----|-----|-----|-----|-----|-----|
|     |     | 20  |     |     |     |     | 25  |     |     |     |     | 30  |     |     |     |

| Phe | Leu | Ile | Pro | Arg | Ile | Gly | Arg | Leu | Ala | Met | Arg | Ile | Ile | Lys | Gln |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Arg | Val | Glu | Ser | Ala | Ala | Asp | Ala | Asp | Thr | Thr | Lys | Asn | Gln | Leu | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Ala | Gly | Val | Gly | Val | Tyr | Ile | Ala | Gln | Ile | Val | Ala | Phe | Phe | Met |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Ala | Val | Ser | Ala | Met | Gln | Ala | Phe | Gly | Phe | Ser | Leu | Ala | Gly | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Ile | Pro | Ala | Thr | Ile | Ala | Ser | Ala | Ala | Ile | Gly | Leu | Gly | Ala | Gln |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Ile | Val | Ala | Asp | Phe | Leu | Ala | Gly | Phe | Phe | Ile | Leu | Thr | Glu | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gln | Phe | Gly | Val | Gly | Asp | Trp | Val | Arg | Phe | Glu | Gly | Asn | Gly | Ile | Val |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Val | Glu | Gly | Thr | Val | Ile | Glu | Ile | Thr | Met | Arg | Ala | Thr | Lys | Ile | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Thr | Ile | Ala | Gln | Glu | Thr | Val | Ile | Ile | Pro | Asn | Ser | Thr | Ala | Lys | Val |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Cys | Ile | Asn | Asn | Ser | Asn | Asn | Trp | Ser | Arg | Ala | Val | Val | Ile | Pro |
|-----|-----|-----|-----|-----|-----|-----|-----|-----|-----|-----|-----|-----|-----|-----|
|     |     |     | 180 |     |     |     |     | 185 |     |     |     |     | 190 |     |

| Ile | Pro | Met | Leu | Gly | Ser | Glu | Asn | Ile | Thr | Asp | Val | Ile | Ala | Arg | Ser |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Glu | Ala | Ala | Thr | Arg | Arg | Ala | Leu | Gly | Gln | Glu | Lys | Ile | Ala | Pro | Glu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Ile | Leu | Gly | Glu | Leu | Asp | Val | His | Pro | Ala | Thr | Glu | Val | Thr | Pro | Pro |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

```
Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530

<210> SEQ ID NO 31
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)

<400> SEQUENCE: 31
gatcttgccg atttcggcag gatcaatgtc ggcgtgaatg atcttggcat caggtgcgaa      60
agtgtcaacg tcaccggtga cgcggtcatc aaagcgggag ccgatagcaa tcagcaggtc    120
gctgcgctgc agtgcaccaa cagcggacac agtgccatgc atgcctggca tacccatgtg    180
cagctcgtgg gactctggga aggttcccag cgccatcaat gtggtgacaa ctggaatgcc    240
ggtgtgctca gcgaacgcac gaagctcttc gtgggcatca gccttgataa cgccgccgcc    300
```

-continued

```
aacgtaaagg acaggcttct tagactcacc gatcagtttg acagcctgct caatctgtcg    360
agcatgcggt gttgaaactg ggcggtagcc tggcaggtcg atctttggtg gccagacgaa    420
atccaattca gcgttctgaa catccttggg gatatccact agaacaggac cagggcgacc    480
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg gccggtgatg caaccatgg gaacggagtc     660 caagtttgca tcagcgattg ggtaaccaa gttggttgcg cctgggccag aggttgcaat     720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc agggcggcg atcgaccac ggcttgcaac      960 cgtggcggga gtgggctgtt gagaagctgc cacattcacg actttctggc tcctttacta   1020
aataaggatt ttcacaggac ccgtccaagc caagccgatt tcaactcagc ctaaagacaa    1080
agccctcatt taaaattgtt ccgacgcgga tgcgtgtgca cgcagtgcga cagatgtctg    1140
ttgcaaagtt ggctacttgg gtcataacca acaagaaagc cctcgttcca acactgtggt    1200
gagtgttgtc gagggcgctt gacgagacga cttggaaggc cgttacggca ggcgccgcgc    1260
ggttactact acaagtcgaa taatggtcat ggtgtgtcat gctacacaca tcgagtttcc    1320
aattccacaa cgcacgaaaa ttcccacccc caaaactccc ccacttcggt taaggaatca    1380
ggattctcac aaagttcagg caggctcccg ctacttttca gcgctaatct tggctc atg   1439
                                                                Met
                                                                  1 att tta ggc gta ccc att caa tat ttg ctc tat tca ttg tgg aat tgg     1487
Ile Leu Gly Val Pro Ile Gln Tyr Leu Leu Tyr Ser Leu Trp Asn Trp
        5                  10                  15 att gtc gat acc ggt ttt gat gta gca att atc ctg gtc ttg gcg ttt     1535
Ile Val Asp Thr Gly Phe Asp Val Ala Ile Ile Leu Val Leu Ala Phe
         20                  25                  30 ttg att cca cgt atc ggc cga ctg gcc atg cgt att atc aag cag cga     1583
Leu Ile Pro Arg Ile Gly Arg Leu Ala Met Arg Ile Ile Lys Gln Arg
     35                  40                  45 gtg gag tct gca gcc gat gcg gac acc act aag aac cag ctc gcg ttc     1631
Val Glu Ser Ala Ala Asp Ala Asp Thr Thr Lys Asn Gln Leu Ala Phe
 50                  55                  60                  65 gct ggc gtt ggc gtt tat atc gcg caa att gtg gcg ttt ttc atg ctt     1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg     1727
Ala Val Ser Ala Met Gln Ala Phe Gly Phe Ser Leu Ala Gly Ala Ala
             85                  90                  95 att ccg gca acc att gcg tca gct gcc att ggt ctt ggt gtg cag tcg     1775
Ile Pro Ala Thr Ile Ala Ser Ala Ala Ile Gly Leu Gly Val Gln Ser
        100                 105                 110 att gtt gcg gac ttc ttg gcc gga ttt ttc atc ctg acg gaa aag caa     1823
Ile Val Ala Asp Phe Leu Ala Gly Phe Phe Ile Leu Thr Glu Lys Gln
    115                 120                 125 ttc ggc gtg ggt gac tgg gtg cgc ttt gag ggc aac ggc atc gtt gtt     1871
Phe Gly Val Gly Asp Trp Val Arg Phe Glu Gly Asn Gly Ile Val Val
130                 135                 140                 145 gaa ggc acc gtc att gag atc acc atg cgc gcg acc aaa att cgc acg     1919
Glu Gly Thr Val Ile Glu Ile Thr Met Arg Ala Thr Lys Ile Arg Thr
                150                 155                 160
```

-continued

| | |
|---|---|
| att gca caa gag acc gtg atc atc ccg aac tcc acg gcg aaa gtg tgc<br>Ile Ala Gln Glu Thr Val Ile Ile Pro Asn Ser Thr Ala Lys Val Cys<br>165                    170                   175 | 1967 |
| atc aac aat tct aat aac tgg tcg cgt gcg gtt gtc gtt att ccg atc<br>Ile Asn Asn Ser Asn Asn Trp Ser Arg Ala Val Val Val Ile Pro Ile<br>180                    185                  190 | 2015 |
| ccc atg ttg ggt tct gaa aac atc aca gat gtc atc gcg cgc tct gaa<br>Pro Met Leu Gly Ser Glu Asn Ile Thr Asp Val Ile Ala Arg Ser Glu<br>195                    200                  205 | 2063 |
| gct gcg act cgt cgc gca ctt ggc cag gag aaa atc gca ccg gaa atc<br>Ala Ala Thr Arg Arg Ala Leu Gly Gln Glu Lys Ile Ala Pro Glu Ile<br>210                    215                  220                  225 | 2111 |
| ctc ggt gaa ctc gat gtg cac cca gcc acg gaa gtc aca ccg cca acg<br>Leu Gly Glu Leu Asp Val His Pro Ala Thr Glu Val Thr Pro Pro Thr<br>                    230                  235                  240 | 2159 |
| gtg gtc ggc atg ccg tgg atg gtc acc atg cgt ttc ctc gtg caa gtc<br>Val Val Gly Met Pro Trp Met Val Thr Met Arg Phe Leu Val Gln Val<br>                    245                  250                  255 | 2207 |
| acc gcc ggc aat caa tgg ctg gtc gaa cgc gcc atc cgc aca gaa atc<br>Thr Ala Gly Asn Gln Trp Leu Val Glu Arg Ala Ile Arg Thr Glu Ile<br>                    260                  265                  270 | 2255 |
| atc aac gaa ttc tgg gaa gaa tac ggc agc gca acc act aca tcg gga<br>Ile Asn Glu Phe Trp Glu Glu Tyr Gly Ser Ala Thr Thr Thr Ser Gly<br>275                    280                  285 | 2303 |
| acc ctc att gat tcc tta cac gtt gag cat gaa gag cca aag acc tcg<br>Thr Leu Ile Asp Ser Leu His Val Glu His Glu Glu Pro Lys Thr Ser<br>290                    295                  300                  305 | 2351 |
| ctt atc gac gcc tcc ccc cag gct ctt aag gaa ccg aag ccg gag gct<br>Leu Ile Asp Ala Ser Pro Gln Ala Leu Lys Glu Pro Lys Pro Glu Ala<br>                    310                  315                  320 | 2399 |
| gcg gcg acg gtt gca tcg cta gct gca tcg tct aac gac gat gca gac<br>Ala Ala Thr Val Ala Ser Leu Ala Ala Ser Ser Asn Asp Asp Ala Asp<br>                    325                  330                  335 | 2447 |
| aat gca gac gcc tcg gcg atc aat gca ggc aat cca gag aag gaa ctt<br>Asn Ala Asp Ala Ser Ala Ile Asn Ala Gly Asn Pro Glu Lys Glu Leu<br>                    340                  345                  350 | 2495 |
| gat tcc gat gtg ctg gaa caa gaa ctc tcc agc gaa gaa ccg gaa gaa<br>Asp Ser Asp Val Leu Glu Gln Glu Leu Ser Ser Glu Glu Pro Glu Glu<br>355                    360                  365 | 2543 |
| aca gca aaa cca gat cac tct ctc cga ggc ttc ttc cgc act gat tac<br>Thr Ala Lys Pro Asp His Ser Leu Arg Gly Phe Phe Arg Thr Asp Tyr<br>370                    375                  380                  385 | 2591 |
| tac cca aat cgg tgg cag aag atc ctg tcg ttt ggc gga cgt gtc cgc<br>Tyr Pro Asn Arg Trp Gln Lys Ile Leu Ser Phe Gly Gly Arg Val Arg<br>                    390                  395                  400 | 2639 |
| atg agc act tcc ctg ttg ttg ggt gcg ctg ctc ttg ctg tca cta ttt<br>Met Ser Thr Ser Leu Leu Leu Gly Ala Leu Leu Leu Leu Ser Leu Phe<br>                    405                  410                  415 | 2687 |
| aag gtc atg act gtg gaa cca agt gag aat tgg caa aac tcc agt gga<br>Lys Val Met Thr Val Glu Pro Ser Glu Asn Trp Gln Asn Ser Ser Gly<br>                    420                  425                  430 | 2735 |
| tgg ctg tca cca agc act gcc acc tca act gcg gtg acc acc tcc gaa<br>Trp Leu Ser Pro Ser Thr Ala Thr Ser Thr Ala Val Thr Thr Ser Glu<br>435                    440                  445 | 2783 |
| act tcc gcg cca gca agc acg cct tcg atg aca gtg ccc act acg gtg<br>Thr Ser Ala Pro Ala Ser Thr Pro Ser Met Thr Val Pro Thr Thr Val<br>450                    455                  460                  465 | 2831 |
| gag gag acc cca acg atg gaa tct agc gtc gaa acg cag cag gaa acc<br>Glu Glu Thr Pro Thr Met Glu Ser Ser Val Glu Thr Gln Gln Glu Thr | 2879 |

-continued

```
                 470             475             480
tca acc cct gca acc gca acg ccc cag cga gcc gac acc atc gaa ccg    2927
Ser Thr Pro Ala Thr Ala Thr Pro Gln Arg Ala Asp Thr Ile Glu Pro
             485             490             495 acc gag gaa gcc acg tcg cag gag gaa acg act gca tcg cag acg cag    2975
Thr Glu Glu Ala Thr Ser Gln Glu Glu Thr Thr Ala Ser Gln Thr Gln
         500             505             510 tct cca gca gtg gaa gca cca acc gcg gtc caa gaa aca gtt gcg ccg    3023
Ser Pro Ala Val Glu Ala Pro Thr Ala Val Gln Glu Thr Val Ala Pro
     515             520             525 acg tcc acc cct taggacgctg attacagacg tgtcccattt ctttactact        3075
Thr Ser Thr Pro
530 attggaaatt atgagttcag acgcagaaaa ggcatccgtg gagctttccg aaaaatttca  3135 cccagaacgc acccatattt tgggcgccgt tgttttggc ctgatctcat tattagtcat   3195 cggcgcagcc cctcagtacc tgttttggct gctcgcgctc cctgtcatct tcggttactg  3255 ggttctaaaa tcatccacga tcgttgatga acagggcatc accgcaaact acgccttcaa  3315 gggcaaaaag gttgtggcct gggaagacct cgcaggaatc ggattcaagg gtgcccgcac  3375 tttcgctcgc accacctccg atgcagaagt caccctcccc ggcgtcacct tcaactccct  3435 tccccgcctt gaagctgctt cccacggccg catccccgat gcgatc                3481
```

<210> SEQ ID NO 32
<211> LENGTH: 533
<212> TYPE: PRT
<213> ORGANISM: Corynebacterium glutamicum

<400> SEQUENCE: 32

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ile Gly Leu Gly Val Gln
            100                 105                 110

Ser Ile Val Ala Asp Phe Leu Ala Gly Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205
```

```
Glu Ala Ala Thr Arg Arg Ala Leu Gly Gln Glu Lys Ile Ala Pro Glu
    210                 215                 220
Ile Leu Gly Glu Leu Asp Val His Pro Ala Thr Glu Val Thr Pro Pro
225                 230                 235                 240
Thr Val Val Gly Met Pro Trp Met Val Thr Met Arg Phe Leu Val Gln
                245                 250                 255
Val Thr Ala Gly Asn Gln Trp Leu Val Glu Arg Ala Ile Arg Thr Glu
            260                 265                 270
Ile Ile Asn Glu Phe Trp Glu Glu Tyr Gly Ser Ala Thr Thr Thr Ser
        275                 280                 285
Gly Thr Leu Ile Asp Ser Leu His Val Glu His Glu Pro Lys Thr
    290                 295                 300
Ser Leu Ile Asp Ala Ser Pro Gln Ala Leu Lys Glu Pro Lys Pro Glu
305                 310                 315                 320
Ala Ala Ala Thr Val Ala Ser Leu Ala Ala Ser Ser Asn Asp Asp Ala
                325                 330                 335
Asp Asn Ala Asp Ala Ser Ala Ile Asn Ala Gly Asn Pro Glu Lys Glu
            340                 345                 350
Leu Asp Ser Asp Val Leu Glu Gln Glu Leu Ser Ser Glu Pro Glu
    355                 360                 365
Glu Thr Ala Lys Pro Asp His Ser Leu Arg Gly Phe Phe Arg Thr Asp
    370                 375                 380
Tyr Tyr Pro Asn Arg Trp Gln Lys Ile Leu Ser Phe Gly Gly Arg Val
385                 390                 395                 400
Arg Met Ser Thr Ser Leu Leu Leu Gly Ala Leu Leu Leu Leu Ser Leu
                405                 410                 415
Phe Lys Val Met Thr Val Glu Pro Ser Glu Asn Trp Gln Asn Ser Ser
            420                 425                 430
Gly Trp Leu Ser Pro Ser Thr Ala Thr Ser Thr Ala Val Thr Thr Ser
        435                 440                 445
Glu Thr Ser Ala Pro Ala Ser Thr Pro Ser Met Thr Val Pro Thr Thr
    450                 455                 460
Val Glu Glu Thr Pro Thr Met Glu Ser Ser Val Glu Thr Gln Gln Glu
465                 470                 475                 480
Thr Ser Thr Pro Ala Thr Ala Thr Pro Gln Arg Ala Asp Thr Ile Glu
                485                 490                 495
Pro Thr Glu Glu Ala Thr Ser Gln Glu Thr Thr Ala Ser Gln Thr
            500                 505                 510
Gln Ser Pro Ala Val Glu Ala Pro Thr Ala Val Gln Glu Thr Val Ala
        515                 520                 525
Pro Thr Ser Thr Pro
    530
```

<210> SEQ ID NO 33
<211> LENGTH: 20
<212> TYPE: DNA
<213> ORGANISM: Artificial sequence
<220> FEATURE:
<223> OTHER INFORMATION: yggB N-terminus primer

<400> SEQUENCE: 33
ggctgttgag aagctgccac                                           20

<210> SEQ ID NO 34
<211> LENGTH: 29
<212> TYPE: DNA

```
<213> ORGANISM: Artificial sequence
<220> FEATURE:
<223> OTHER INFORMATION: yggB N-terminus primer2

<400> SEQUENCE: 34
ccgcaacaat cgactgcaca ccaagacca                                29

<210> SEQ ID NO 35
<211> LENGTH: 28
<212> TYPE: DNA
<213> ORGANISM: Artificial sequence
<220> FEATURE:
<223> OTHER INFORMATION: yggB C-terminus primer1

<400> SEQUENCE: 35
gggagctcca cggcatgccg accaccgt                                 28

<210> SEQ ID NO 36
<211> LENGTH: 29
<212> TYPE: DNA
<213> ORGANISM: Artificial sequence
<220> FEATURE:
<223> OTHER INFORMATION: yggB C-terminus primer2

<400> SEQUENCE: 36
tggtcttggt gtgcagtcga ttgttgcgg                                29

<210> SEQ ID NO 37
<211> LENGTH: 28
<212> TYPE: DNA
<213> ORGANISM: Artificial sequence
<220> FEATURE:
<223> OTHER INFORMATION: yggB 2nd primer

<400> SEQUENCE: 37
gggagctcga ctttctggct cctttact                                 28

<210> SEQ ID NO 38
<211> LENGTH: 28
<212> TYPE: DNA
<213> ORGANISM: Artificial sequence
<220> FEATURE:
<223> OTHER INFORMATION: sucA8primer

<400> SEQUENCE: 38
ctgcgtcgac gtcggaggca ccatccac                                 28

<210> SEQ ID NO 39
<211> LENGTH: 30
<212> TYPE: DNA
<213> ORGANISM: Artificial sequence
<220> FEATURE:
<223> OTHER INFORMATION: sucA801primer

<400> SEQUENCE: 39
ctgcgtctcg acgtcggagg caccatccac                               30

<210> SEQ ID NO 40
<211> LENGTH: 36
<212> TYPE: DNA
<213> ORGANISM: Artificial sequence
<220> FEATURE:
<223> OTHER INFORMATION: sucA805primer

<400> SEQUENCE: 40
gctaaaagct gcgtcgacgt cggaggcacc atccac                        36
```

<210> SEQ ID NO 41
<211> LENGTH: 36
<212> TYPE: DNA
<213> ORGANISM: Artificial sequence
<220> FEATURE:
<223> OTHER INFORMATION: Synthetic DNA

<400> SEQUENCE: 41
gctataagct gcgtcgacgt cggaggcacc atccac                36

<210> SEQ ID NO 42
<211> LENGTH: 4389
<212> TYPE: DNA
<213> ORGANISM: Corynebacterium glutamicum
<220> FEATURE:
<221> NAME/KEY: CDS
<222> LOCATION: (443)..(2542)

<400> SEQUENCE: 42

| | | |
|---|---|---|
| gtcgacaagc aaaatcgaag cggcagcacg ccgcgtcgga gccttaaacg ccatcgccgc | 60 |
| catccctgat ggtttcaatc atcaagtcgg tgaacgcggg cgcaacctgt catccggaca | 120 |
| gcgccaactg atcgcgctgg cgcgcgccga actcatcgag ccttccatca tgcttctcga | 180 |
| cgaagccacc tccaccctcg accccgccac cgaagccgtt atcctcaacg cctccgatcg | 240 |
| agtcactaag ggacgcacca gcatcatcgt cgcgcaccgc ttggcaaccg ctaaaagggc | 300 |
| cgaccgtatt cttgttgttg aacaaggacg tatcattgag gacggatctc acgacgcgtt | 360 |
| gttgtctgct aacggcacct acgcccgcat gtggcattta atggcctgac acgttatttt | 420 |
| taggagaact gtcaacaaat ta atg cta caa ctg ggg ctt agg cat aat cag | 472 |
|   Met Leu Gln Leu Gly Leu Arg His Asn Gln | |
|   1               5                   10 | |
| cca acg acc aac gtt aca gtg gat aaa ata aag ctc aat aaa ccc tca | 520 |
| Pro Thr Thr Asn Val Thr Val Asp Lys Ile Lys Leu Asn Lys Pro Ser | |
|         15                  20                  25 | |
| aga agc aag gaa aag agg cga gta cct gcc gtg agc agc gct agt act | 568 |
| Arg Ser Lys Glu Lys Arg Arg Val Pro Ala Val Ser Ser Ala Ser Thr | |
|     30                  35                  40 | |
| ttc ggc cag aat gcg tgg ctg gta gac gag atg ttc cag cag ttc cag | 616 |
| Phe Gly Gln Asn Ala Trp Leu Val Asp Glu Met Phe Gln Gln Phe Gln | |
| 45                  50                  55 | |
| aag gac ccc aag tcc gtg gac aag gaa tgg aga gaa ctc ttt gag gcg | 664 |
| Lys Asp Pro Lys Ser Val Asp Lys Glu Trp Arg Glu Leu Phe Glu Ala | |
|         60                  65                  70 | |
| cag ggg gga cca aat gct acc ccc gct aca aca gaa gca cag cct tca | 712 |
| Gln Gly Gly Pro Asn Ala Thr Pro Ala Thr Thr Glu Ala Gln Pro Ser | |
| 75                  80                  85                  90 | |
| gcg ccc aag gag tct gcg aaa cca gca cca aag gct gcc cct gca gcc | 760 |
| Ala Pro Lys Glu Ser Ala Lys Pro Ala Pro Lys Ala Ala Pro Ala Ala | |
|             95                 100                 105 | |
| aag gca gca ccg cgc gta gaa acc aag ccg gcc gcc aag acc gcc cct | 808 |
| Lys Ala Ala Pro Arg Val Glu Thr Lys Pro Ala Ala Lys Thr Ala Pro | |
|         110                 115                 120 | |
| aag gcc aag gag tcc tca gtg cca cag caa cct aag ctt ccg gag cca | 856 |
| Lys Ala Lys Glu Ser Ser Val Pro Gln Gln Pro Lys Leu Pro Glu Pro | |
|     125                 130                 135 | |
| gga caa acc cca atc agg ggt att ttc aag tcc atc gcg aag aac atg | 904 |
| Gly Gln Thr Pro Ile Arg Gly Ile Phe Lys Ser Ile Ala Lys Asn Met | |
| 140                 145                 150 | |
| gat atc tcc ctg gaa atc cca acc gca acc tcg gtt cgc gat atg cca | 952 |

-continued

```
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag      1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc      1048
Arg Thr Arg Gly Gly Lys Ile Ser Phe Thr His Ile Ile Gly Tyr Ala
                190                 195                 200 atg gtg aag gca gtc atg gct cac ccg gac atg aac aac tcc tac gac      1096
Met Val Lys Ala Val Met Ala His Pro Asp Met Asn Asn Ser Tyr Asp
            205                 210                 215 gtc atc gac ggc aag cca acc ctg atc gtg cct gag cac atc aac ctg      1144
Val Ile Asp Gly Lys Pro Thr Leu Ile Val Pro Glu His Ile Asn Leu
        220                 225                 230 ggc ctt gcc atc gac ctt cct cag aag gac ggc tcc cgc gca ctt gtc      1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc      1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc      1288
Ala Ala Tyr Glu Asp Ile Val Thr Arg Ser Arg Lys Gly Lys Leu Thr
                270                 275                 280 atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
            285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
        300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
                350                 355                 360 ttc ctg cgt acc atg tct cgc ctg ctc acc gat gat tcc ttc tgg gat      1576
Phe Leu Arg Thr Met Ser Arg Leu Leu Thr Asp Asp Ser Phe Trp Asp
            365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
        380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac      1768
Pro Leu Ser Trp Val Gln Pro Gly Met Pro Val Pro Asp His Arg Asp
                430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
            445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
        460                 465                 470
```

```
gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc      1960
Tyr Thr His Ile Leu Asp Arg Asp Glu Arg Thr Trp Leu Gln Asp Arg
            495                 500                 505 ctc gaa gcc gga atg cca aag cca acc cag gca gag cag aag tac atc      2008
Leu Glu Ala Gly Met Pro Lys Pro Thr Gln Ala Glu Gln Lys Tyr Ile
        510                 515                 520 ctg cag aag ctg aac gcc gca gag gct ttc gag aac ttc ctg cag acc      2056
Leu Gln Lys Leu Asn Ala Ala Glu Ala Phe Glu Asn Phe Leu Gln Thr
    525                 530                 535 aag tac gtc ggc cag aag cgc ttc tcc ctc gaa ggt gca gaa gct ctc      2104
Lys Tyr Val Gly Gln Lys Arg Phe Ser Leu Glu Gly Ala Glu Ala Leu
540                 545                 550 atc cca ctg atg gac tcc gcc atc gac acc gcc gca ggc cag ggc ctc      2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg      2200
Asp Glu Val Val Ile Gly Met Pro His Arg Gly Arg Leu Asn Val Leu
            575                 580                 585 ttc aac atc gtg ggc aag cca ctg gca tcc atc ttc aac gag ttt gaa      2248
Phe Asn Ile Val Gly Lys Pro Leu Ala Ser Ile Phe Asn Glu Phe Glu
        590                 595                 600 ggc caa atg gag cag ggc cag atc ggt ggc tcc ggt gac gtg aag tac      2296
Gly Gln Met Glu Gln Gly Gln Ile Gly Gly Ser Gly Asp Val Lys Tyr
    605                 610                 615 cac ctc ggt tcc gaa ggc cag cac ctg cag atg ttc ggc gac ggc gag      2344
His Leu Gly Ser Glu Gly Gln His Leu Gln Met Phe Gly Asp Gly Glu
620                 625                 630 atc aag gtc tcc ctg act gct aac ccg tcc cac ctg gaa gct gtt aac      2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag      2440
Pro Val Met Glu Gly Ile Val Arg Ala Lys Gln Asp Tyr Leu Asp Lys
            655                 660                 665 ggc gta gac ggc aag act gtt gtg cca ctg ctc ctc cac ggt gac gct      2488
Gly Val Asp Gly Lys Thr Val Val Pro Leu Leu Leu His Gly Asp Ala
        670                 675                 680 gca ttc gca ggc ctg ggc atc gtg cca gaa acc atc aac ctg gct aag      2536
Ala Phe Ala Gly Leu Gly Ile Val Pro Glu Thr Ile Asn Leu Ala Lys
    685                 690                 695 ctg cgt cgacgtcgga ggcaccatcc acatcgtggt gaacaaccag atcggcttca      2592
Leu Arg
700 ccaccacccc agactccagc cgctccatgc actacgcaac cgactacgcc aaggcattcg      2652 gctgcccagt cttccacgtc aatggtgatg acccagaggc agttgtctgg gttggccagc      2712 tggcaaccga gtaccgtcgt cgcttcggca aggacgtctt catcgacctc gtttgctacc      2772 gcctccgcgg ccacaacgaa gctgatgatc cttccatgac ccagccaaag atgtatgagc      2832 tcatcaccgg ccgcgagacc gttcgtgctc agtacaccga agacctgctc ggacgtggag      2892 acctctccaa cgaagatgca gaagcagtcg tccgcgactt ccacgaccag atggaatctg      2952 tgttcaacga agtcaaggaa ggcggcaaga agcaggctga ggcacagacc ggcatcaccg      3012 gctcccagaa gcttccacac ggccttgaga ccaacatctc ccgtgaagag ctcctggaac      3072 tgggacaggg tttcgccaac accccagaag gcttcaacta ccaccacgt gtggctccag      3132 ttgctaagaa gcgcgtctcc tctgtcaccg aaggtggcat cgactgggca tggggcgagc      3192
```

-continued

```
tcctcgcctt cggttccctg gctaactccg gccgcttggt tcgccttgca ggtgaagatt    3252
cccgccgcgg taccttcacc cagcgccacg cagttgccat cgacccagcg accgctgaag    3312
agttcaaccc actccacgag cttgcacagt ccaagggcaa caacggtaag ttcctggtct    3372
acaactccgc actgaccgag tacgcaggca tgggcttcga gtacggctac tccgtaggaa    3432
acgaagactc cgtcgttgca tgggaagcac agttcggcga cttcgccaac ggcgctcaga    3492
ccatcatcga tgagtacgtc tcctcaggcg aagctaagtg gggccagacc tccaagctga    3552
tccttctgct gcctcacggc tacgaaggcc agggcccaga ccactcttcc gcacgtatcg    3612
agcgcttcct gcagctgtgc gctgagggtt ccatgactgt tgctcagcca tccacccccag   3672
caaaccactt ccacctgctg cgtcgtcacg ctctgtccga cctgaagcgt ccactggtta    3732
tcttcacccc gaagtccatg ctgcgtaaca aggctgctgc ctccgcacca aagacttca    3792
ctgaggtcac caagttccaa tccgtgatcg acgatccaaa cgttgcagat gcagccaagg    3852
tgaagaaggt catgctggtc tccggcaagc tgtactacga attggcaaag cgcaaggaga    3912
aggacggacg cgacgacatc gcgatcgttc gtatcgaaat gctccacccca attccgttca    3972
accgcatctc cgaggctctt gccggctacc ctaacgctga ggaagtcctc ttcgttcagg    4032
atgagccagc aaaccagggc ccatggccgt tctaccagga gcacctccca gagctgatcc    4092
cgaacatgcc aaagatgcgc cgcgtttccc gccgcgctca gtcctccacc gcaactggtg    4152
ttgctaaggt gcaccagctg gaggagaagc agcttatcga cgaggctttc gaggcttaag    4212
tctttatagt cctgcactag cctagagggc cttatgcagt gtgaatcaca cagcataagg    4272
ccctttttgc tgccgtggtt gcctaaggtg gaaggcatga aacgaatctg tgcggtcacg    4332
atctcttcag tacttttgct aagtggctgc tcctccactt ccaccacgca gctcgag       4389
```

<210> SEQ ID NO 43
<211> LENGTH: 700
<212> TYPE: PRT
<213> ORGANISM: Corynebacterium glutamicum

<400> SEQUENCE: 43

```
Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160
```

-continued

```
Pro Thr Ala Thr Ser Val Arg Asp Met Pro Ala Arg Leu Met Phe Glu
            165                 170                 175

Asn Arg Ala Met Val Asn Asp Gln Leu Lys Arg Thr Arg Gly Gly Lys
                180                 185                 190

Ile Ser Phe Thr His Ile Ile Gly Tyr Ala Met Val Lys Ala Val Met
            195                 200                 205

Ala His Pro Asp Met Asn Asn Ser Tyr Asp Val Ile Asp Gly Lys Pro
210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
            275                 280                 285

Val Thr Val Ser Leu Thr Asn Pro Gly Gly Ile Gly Thr Arg His Ser
            290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
            355                 360                 365

Arg Leu Leu Thr Asp Asp Ser Phe Trp Asp Glu Ile Phe Asp Ala Met
            370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
            435                 440                 445

Ser Leu Thr Ile Trp Asp Leu Asp Arg Thr Phe Ser Val Gly Gly Phe
450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
            515                 520                 525

Ala Glu Ala Phe Glu Asn Phe Leu Gln Thr Lys Tyr Val Gly Gln Lys
            530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
```

-continued

```
                580                 585                 590
Pro Leu Ala Ser Ile Phe Asn Glu Phe Glu Gly Gln Met Glu Gln Gly
            595                 600                 605
Gln Ile Gly Gly Ser Gly Asp Val Lys Tyr His Leu Gly Ser Glu Gly
        610                 615                 620
Gln His Leu Gln Met Phe Gly Asp Gly Glu Ile Lys Val Ser Leu Thr
625                 630                 635                 640
Ala Asn Pro Ser His Leu Glu Ala Val Asn Pro Val Met Glu Gly Ile
                645                 650                 655
Val Arg Ala Lys Gln Asp Tyr Leu Asp Lys Gly Val Asp Gly Lys Thr
            660                 665                 670
Val Val Pro Leu Leu Leu His Gly Asp Ala Ala Phe Ala Gly Leu Gly
        675                 680                 685
Ile Val Pro Glu Thr Ile Asn Leu Ala Lys Leu Arg
690                 695                 700
```

<210> SEQ ID NO 44
<211> LENGTH: 4391
<212> TYPE: DNA
<213> ORGANISM: Corynebacterium glutamicum
<220> FEATURE:
<221> NAME/KEY: CDS
<222> LOCATION: (443)..(4210)
<223> OTHER INFORMATION: sucA801

<400> SEQUENCE: 44

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag     472
                         Met Leu Gln Leu Gly Leu Arg His Asn Gln
                         1               5                  10
```

```
cca acg acc aac gtt aca gtg gat aaa ata aag ctc aat aaa ccc tca     520
Pro Thr Thr Asn Val Thr Val Asp Lys Ile Lys Leu Asn Lys Pro Ser
            15                  20                  25 aga agc aag gaa aag agg cga gta cct gcc gtg agc agc gct agt act     568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag     616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg     664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca     712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc     760
Ala Pro Lys Glu Ser Ala Lys Pro Ala Pro Lys Ala Ala Pro Ala Ala
                95                 100                 105 aag gca gca ccg cgc gta gaa acc aag ccg gcc gcc aag acc gcc cct     808
Lys Ala Ala Pro Arg Val Glu Thr Lys Pro Ala Ala Lys Thr Ala Pro
```

-continued

```
                      110                 115                 120
aag gcc aag gag tcc tca gtg cca cag caa cct aag ctt ccg gag cca         856
Lys Ala Lys Glu Ser Ser Val Pro Gln Gln Pro Lys Leu Pro Glu Pro
            125                 130                 135 gga caa acc cca atc agg ggt att ttc aag tcc atc gcg aag aac atg         904
Gly Gln Thr Pro Ile Arg Gly Ile Phe Lys Ser Ile Ala Lys Asn Met
        140                 145                 150 gat atc tcc ctg gaa atc cca acc gca acc tcg gtt cgc gat atg cca         952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag        1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc        1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac        1096
Met Val Lys Ala Val Met Ala His Pro Asp Met Asn Asn Ser Tyr Asp
        205                 210                 215 gtc atc gac ggc aag cca acc ctg atc gtg cct gag cac atc aac ctg        1144
Val Ile Asp Gly Lys Pro Thr Leu Ile Val Pro Glu His Ile Asn Leu
220                 225                 230 ggc ctt gcc atc gac ctt cct cag aag gac ggc tcc cgc gca ctt gtc        1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc        1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc        1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc        1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc        1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct        1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc        1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa        1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat        1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca        1624
Glu Ile Phe Asp Ala Met Asn Val Pro Tyr Thr Pro Met Arg Trp Ala
380                 385                 390 cag gac gtt cca aac acc ggt gtt gat aag aac acc cgc gtc atg cag        1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac        1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac        1768
```

-continued

```
Pro Leu Ser Trp Val Gln Pro Gly Met Pro Val Pro Asp His Arg Asp
            430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
                445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
    460                 465                 470 gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc      1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc      2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc      2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gct ctc      2104
Lys Tyr Val Gly Gln Lys Arg Phe Ser Leu Glu Gly Ala Glu Ala Leu
    540                 545                 550 atc cca ctg atg gac tcc gcc atc gac acc gcc gca ggc cag ggc ctc      2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg      2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa      2248
Phe Asn Ile Val Gly Lys Pro Leu Ala Ser Ile Phe Asn Glu Phe Glu
            590                 595                 600 ggc caa atg gag cag ggc cag atc ggt ggc tcc ggt gac gtg aag tac      2296
Gly Gln Met Glu Gln Gly Gln Ile Gly Gly Ser Gly Asp Val Lys Tyr
        605                 610                 615 cac ctc ggt tcc gaa ggc cag cac ctg cag atg ttc ggc gac ggc gag      2344
His Leu Gly Ser Glu Gly Gln His Leu Gln Met Phe Gly Asp Gly Glu
    620                 625                 630 atc aag gtc tcc ctg act gct aac ccg tcc cac ctg gaa gct gtt aac      2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag      2440
Pro Val Met Glu Gly Ile Val Arg Ala Lys Gln Asp Tyr Leu Asp Lys
                655                 660                 665 ggc gta gac ggc aag act gtt gtg cca ctg ctg ctc cac ggt gac gct      2488
Gly Val Asp Gly Lys Thr Val Val Pro Leu Leu Leu His Gly Asp Ala
            670                 675                 680 gca ttc gca ggc ctg ggc atc gtg cca gaa acc atc aac ctg gct aag      2536
Ala Phe Ala Gly Leu Gly Ile Val Pro Glu Thr Ile Asn Leu Ala Lys
        685                 690                 695 ctg cgt ctc gac gtc gga ggc acc atc cac atc gtg gtg aac aac cag      2584
Leu Arg Leu Asp Val Gly Gly Thr Ile His Ile Val Val Asn Asn Gln
    700                 705                 710 atc ggc ttc acc acc acc cca gac tcc agc cgc tcc atg cac tac gca      2632
Ile Gly Phe Thr Thr Thr Pro Asp Ser Ser Arg Ser Met His Tyr Ala
715                 720                 725                 730 acc gac tac gcc aag gca ttc ggc tgc cca gtc ttc cac gtc aat ggt      2680
Thr Asp Tyr Ala Lys Ala Phe Gly Cys Pro Val Phe His Val Asn Gly
                735                 740                 745
```

```
                                                                       -continued gat gac cca gag gca gtt gtc tgg gtt ggc cag ctg gca acc gag tac        2728
Asp Asp Pro Glu Ala Val Val Trp Val Gly Gln Leu Ala Thr Glu Tyr
            750                 755                 760 cgt cgt cgc ttc ggc aag gac gtc ttc atc gac ctc gtt tgc tac cgc        2776
Arg Arg Arg Phe Gly Lys Asp Val Phe Ile Asp Leu Val Cys Tyr Arg
765                 770                 775 ctc cgc ggc cac aac gaa gct gat gat cct tcc atg acc cag cca aag        2824
Leu Arg Gly His Asn Glu Ala Asp Asp Pro Ser Met Thr Gln Pro Lys
        780                 785                 790 atg tat gag ctc atc acc ggc cgc gag acc gtt cgt gct cag tac acc        2872
Met Tyr Glu Leu Ile Thr Gly Arg Glu Thr Val Arg Ala Gln Tyr Thr
795                 800                 805                 810 gaa gac ctg ctc gga cgt gga gac ctc tcc aac gaa gat gca gaa gca        2920
Glu Asp Leu Leu Gly Arg Gly Asp Leu Ser Asn Glu Asp Ala Glu Ala
                815                 820                 825 gtc gtc cgc gac ttc cac gac cag atg gaa tct gtg ttc aac gaa gtc        2968
Val Val Arg Asp Phe His Asp Gln Met Glu Ser Val Phe Asn Glu Val
            830                 835                 840 aag gaa ggc ggc aag aag cag gct gag gca cag acc ggc atc acc ggc        3016
Lys Glu Gly Gly Lys Lys Gln Ala Glu Ala Gln Thr Gly Ile Thr Gly
        845                 850                 855 tcc cag aag ctt cca cac ggc ctt gag acc aac atc tcc cgt gaa gag        3064
Ser Gln Lys Leu Pro His Gly Leu Glu Thr Asn Ile Ser Arg Glu Glu
    860                 865                 870 ctc ctg gaa ctg gga cag gct ttc gcc aac acc cca gaa ggc ttc aac        3112
Leu Leu Glu Leu Gly Gln Ala Phe Ala Asn Thr Pro Glu Gly Phe Asn
875                 880                 885                 890 tac cac cca cgt gtg gct cca gtt gct aag aag cgc gtc tcc tct gtc        3160
Tyr His Pro Arg Val Ala Pro Val Ala Lys Lys Arg Val Ser Ser Val
                895                 900                 905 acc gaa ggt ggc atc gac tgg gca tgg ggc gag ctc ctc gcc ttc ggt        3208
Thr Glu Gly Gly Ile Asp Trp Ala Trp Gly Glu Leu Leu Ala Phe Gly
            910                 915                 920 tcc ctg gct aac tcc ggc cgc ttg gtt cgc ctt gca ggt gaa gat tcc        3256
Ser Leu Ala Asn Ser Gly Arg Leu Val Arg Leu Ala Gly Glu Asp Ser
        925                 930                 935 cgc cgc ggt acc ttc acc cag cgc cac gca gtt gcc atc gac cca gcg        3304
Arg Arg Gly Thr Phe Thr Gln Arg His Ala Val Ala Ile Asp Pro Ala
    940                 945                 950 acc gct gaa gag ttc aac cca ctc cac gag ctt gca cag tcc aag ggc        3352
Thr Ala Glu Glu Phe Asn Pro Leu His Glu Leu Ala Gln Ser Lys Gly
955                 960                 965                 970 aac aac ggt aag ttc ctg gtc tac aac tcc gca ctg acc gag tac gca        3400
Asn Asn Gly Lys Phe Leu Val Tyr Asn Ser Ala Leu Thr Glu Tyr Ala
                975                 980                 985 ggc atg ggc ttc gag tac ggc tac tcc gta gga aac gaa gac tcc gtc        3448
Gly Met Gly Phe Glu Tyr Gly Tyr Ser Val Gly Asn Glu Asp Ser Val
            990                 995                 1000 gtt gca tgg gaa gca cag ttc ggc gac ttc gcc aac ggc gct cag             3493
Val Ala Trp Glu Ala Gln Phe Gly Asp Phe Ala Asn Gly Ala Gln
        1005                1010                1015 acc atc atc gat gag tac gtc tcc tca ggc gaa gct aag tgg ggc             3538
Thr Ile Ile Asp Glu Tyr Val Ser Ser Gly Glu Ala Lys Trp Gly
    1020                1025                1030 cag acc tcc aag ctg atc ctt ctg ctg cct cac ggc tac gaa ggc             3583
Gln Thr Ser Lys Leu Ile Leu Leu Leu Pro His Gly Tyr Glu Gly
1035                1040                1045 cag ggc cca gac cac tct tcc gca cgt atc gag cgc ttc ctg cag             3628
Gln Gly Pro Asp His Ser Ser Ala Arg Ile Glu Arg Phe Leu Gln
                1050                1055                1060
```

-continued

| | | |
|---|---|---|
| ctg tgc gct gag ggt tcc atg act gtt gct cag cca tcc acc cca<br>Leu Cys Ala Glu Gly Ser Met Thr Val Ala Gln Pro Ser Thr Pro<br>1065                       1070                     1075 | 3673 |
| gca aac cac ttc cac ctg ctg cgt cgt cac gct ctg tcc gac ctg<br>Ala Asn His Phe His Leu Leu Arg Arg His Ala Leu Ser Asp Leu<br>1080                     1085                     1090 | 3718 |
| aag cgt cca ctg gtt atc ttc acc ccg aag tcc atg ctg cgt aac<br>Lys Arg Pro Leu Val Ile Phe Thr Pro Lys Ser Met Leu Arg Asn<br>1095                     1100                     1105 | 3763 |
| aag gct gct gcc tcc gca cca gaa gac ttc act gag gtc acc aag<br>Lys Ala Ala Ala Ser Ala Pro Glu Asp Phe Thr Glu Val Thr Lys<br>1110                     1115                     1120 | 3808 |
| ttc caa tcc gtg atc gac gat cca aac gtt gca gat gca gcc aag<br>Phe Gln Ser Val Ile Asp Asp Pro Asn Val Ala Asp Ala Ala Lys<br>1125                     1130                     1135 | 3853 |
| gtg aag aag gtc atg ctg gtc tcc ggc aag ctg tac tac gaa ttg<br>Val Lys Lys Val Met Leu Val Ser Gly Lys Leu Tyr Tyr Glu Leu<br>1140                     1145                     1150 | 3898 |
| gca aag cgc aag gag aag gac gga cgc gac gac atc gcg atc gtt<br>Ala Lys Arg Lys Glu Lys Asp Gly Arg Asp Asp Ile Ala Ile Val<br>1155                     1160                     1165 | 3943 |
| cgt atc gaa atg ctc cac cca att ccg ttc aac cgc atc tcc gag<br>Arg Ile Glu Met Leu His Pro Ile Pro Phe Asn Arg Ile Ser Glu<br>1170                     1175                     1180 | 3988 |
| gct ctt gcc ggc tac cct aac gct gag gaa gtc ctc ttc gtt cag<br>Ala Leu Ala Gly Tyr Pro Asn Ala Glu Glu Val Leu Phe Val Gln<br>1185                     1190                     1195 | 4033 |
| gat gag cca gca aac cag ggc cca tgg ccg ttc tac cag gag cac<br>Asp Glu Pro Ala Asn Gln Gly Pro Trp Pro Phe Tyr Gln Glu His<br>1200                     1205                     1210 | 4078 |
| ctc cca gag ctg atc ccg aac atg cca aag atg cgc cgc gtt tcc<br>Leu Pro Glu Leu Ile Pro Asn Met Pro Lys Met Arg Arg Val Ser<br>1215                     1220                     1225 | 4123 |
| cgc cgc gct cag tcc tcc acc gca act ggt gtt gct aag gtg cac<br>Arg Arg Ala Gln Ser Ser Thr Ala Thr Gly Val Ala Lys Val His<br>1230                     1235                     1240 | 4168 |
| cag ctg gag gag aag cag ctt atc gac gag gct ttc gag gct<br>Gln Leu Glu Glu Lys Gln Leu Ile Asp Glu Ala Phe Glu Ala<br>1245                     1250                     1255 | 4210 |
| taagtcttta tagtcctgca ctagcctaga gggccttatg cagtgtgaat cacacagcat | 4270 |
| aaggcccttt tgctgccgt ggttgcctaa ggtggaaggc atgaaacgaa tctgtgcggt | 4330 |
| cacgatctct tcagtacttt tgctaagtgg ctgctcctcc acttccacca cgcagctcga | 4390 |
| g | 4391 |

<210> SEQ ID NO 45
<211> LENGTH: 1256
<212> TYPE: PRT
<213> ORGANISM: Corynebacterium glutamicum

<400> SEQUENCE: 45

Met Leu Gln Leu Gly Leu Arg His Asn Gln Pro Thr Thr Asn Val Thr
1               5                 10                 15

Val Asp Lys Ile Lys Leu Asn Lys Pro Ser Arg Ser Lys Glu Lys Arg
               20                 25                 30

Arg Val Pro Ala Val Ser Ser Ala Ser Thr Phe Gly Gln Asn Ala Trp
           35                 40                 45

Leu Val Asp Glu Met Phe Gln Gln Phe Gln Lys Asp Pro Lys Ser Val

-continued

```
                 50                  55                  60
Asp Lys Glu Trp Arg Glu Leu Phe Glu Ala Gln Gly Gly Pro Asn Ala
 65                  70                  75                  80

Thr Pro Ala Thr Thr Glu Ala Gln Pro Ser Ala Pro Lys Glu Ser Ala
                 85                  90                  95

Lys Pro Ala Pro Lys Ala Ala Pro Ala Ala Lys Ala Ala Pro Arg Val
                100                 105                 110

Glu Thr Lys Pro Ala Ala Lys Thr Ala Pro Lys Ala Lys Glu Ser Ser
                115                 120                 125

Val Pro Gln Gln Pro Lys Leu Pro Glu Pro Gly Gln Thr Pro Ile Arg
130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
                180                 185                 190

Ile Ser Phe Thr His Ile Ile Gly Tyr Ala Met Val Lys Ala Val Met
                195                 200                 205

Ala His Pro Asp Met Asn Asn Ser Tyr Asp Val Ile Asp Gly Lys Pro
                210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
                260                 265                 270

Val Thr Arg Ser Arg Lys Gly Lys Leu Thr Met Asp Asp Tyr Gln Gly
                275                 280                 285

Val Thr Val Ser Leu Thr Asn Pro Gly Gly Ile Gly Thr Arg His Ser
                290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
                340                 345                 350

Arg Val Ile Gln Gly Ala Val Ser Gly Glu Phe Leu Arg Thr Met Ser
                355                 360                 365

Arg Leu Leu Thr Asp Asp Ser Phe Trp Asp Glu Ile Phe Asp Ala Met
                370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
                420                 425                 430

Pro Gly Met Pro Val Pro Asp His Arg Asp Leu Asp Ile Glu Thr His
                435                 440                 445

Ser Leu Thr Ile Trp Asp Leu Asp Arg Thr Phe Ser Val Gly Gly Phe
                450                 455                 460

Gly Gly Lys Glu Thr Met Thr Leu Arg Glu Val Leu Ser Arg Leu Arg
465                 470                 475                 480
```

```
Ala Ala Tyr Thr Leu Lys Val Gly Ser Glu Tyr Thr His Ile Leu Asp
            485                 490                 495
Arg Asp Glu Arg Thr Trp Leu Gln Asp Arg Leu Glu Ala Gly Met Pro
        500                 505                 510
Lys Pro Thr Gln Ala Glu Gln Lys Tyr Ile Leu Gln Lys Leu Asn Ala
        515                 520                 525
Ala Glu Ala Phe Glu Asn Phe Leu Gln Thr Lys Tyr Val Gly Gln Lys
        530                 535                 540
Arg Phe Ser Leu Glu Gly Ala Glu Ala Leu Ile Pro Leu Met Asp Ser
545                 550                 555                 560
Ala Ile Asp Thr Ala Ala Gly Gln Gly Leu Asp Glu Val Val Ile Gly
            565                 570                 575
Met Pro His Arg Gly Arg Leu Asn Val Leu Phe Asn Ile Val Gly Lys
            580                 585                 590
Pro Leu Ala Ser Ile Phe Asn Glu Phe Glu Gly Gln Met Glu Gln Gly
            595                 600                 605
Gln Ile Gly Gly Ser Gly Asp Val Lys Tyr His Leu Gly Ser Glu Gly
        610                 615                 620
Gln His Leu Gln Met Phe Gly Asp Gly Glu Ile Lys Val Ser Leu Thr
625                 630                 635                 640
Ala Asn Pro Ser His Leu Glu Ala Val Asn Pro Val Met Glu Gly Ile
            645                 650                 655
Val Arg Ala Lys Gln Asp Tyr Leu Asp Lys Gly Val Asp Gly Lys Thr
            660                 665                 670
Val Val Pro Leu Leu Leu His Gly Asp Ala Ala Phe Ala Gly Leu Gly
            675                 680                 685
Ile Val Pro Glu Thr Ile Asn Leu Ala Lys Leu Arg Leu Asp Val Gly
            690                 695                 700
Gly Thr Ile His Ile Val Val Asn Asn Gln Ile Gly Phe Thr Thr Thr
705                 710                 715                 720
Pro Asp Ser Ser Arg Ser Met His Tyr Ala Thr Asp Tyr Ala Lys Ala
                725                 730                 735
Phe Gly Cys Pro Val Phe His Val Asn Gly Asp Asp Pro Glu Ala Val
            740                 745                 750
Val Trp Val Gly Gln Leu Ala Thr Glu Tyr Arg Arg Phe Gly Lys
            755                 760                 765
Asp Val Phe Ile Asp Leu Val Cys Tyr Arg Leu Arg Gly His Asn Glu
    770                 775                 780
Ala Asp Asp Pro Ser Met Thr Gln Pro Lys Met Tyr Glu Leu Ile Thr
785                 790                 795                 800
Gly Arg Glu Thr Val Arg Ala Gln Tyr Thr Glu Asp Leu Leu Gly Arg
                805                 810                 815
Gly Asp Leu Ser Asn Glu Asp Ala Glu Ala Val Val Arg Asp Phe His
            820                 825                 830
Asp Gln Met Glu Ser Val Phe Asn Glu Val Lys Glu Gly Gly Lys Lys
            835                 840                 845
Gln Ala Glu Ala Gln Thr Gly Ile Thr Gly Ser Gln Lys Leu Pro His
        850                 855                 860
Gly Leu Glu Thr Asn Ile Ser Arg Glu Glu Leu Leu Glu Leu Gly Gln
865                 870                 875                 880
Ala Phe Ala Asn Thr Pro Glu Gly Phe Asn Tyr His Pro Arg Val Ala
                885                 890                 895
```

```
Pro Val Ala Lys Lys Arg Val Ser Ser Val Thr Glu Gly Gly Ile Asp
            900                 905                 910

Trp Ala Trp Gly Glu Leu Leu Ala Phe Gly Ser Leu Ala Asn Ser Gly
        915                 920                 925

Arg Leu Val Arg Leu Ala Gly Glu Asp Ser Arg Gly Thr Phe Thr
    930                 935                 940

Gln Arg His Ala Val Ala Ile Asp Pro Ala Thr Ala Glu Glu Phe Asn
945                 950                 955                 960

Pro Leu His Glu Leu Ala Gln Ser Lys Gly Asn Asn Gly Lys Phe Leu
                965                 970                 975

Val Tyr Asn Ser Ala Leu Thr Glu Tyr Ala Gly Met Gly Phe Glu Tyr
                980                 985                 990

Gly Tyr Ser Val Gly Asn Glu Asp Ser Val Val Ala Trp Glu Ala Gln
            995                 1000                1005

Phe Gly Asp Phe Ala Asn Gly Ala Gln Thr Ile Ile Asp Glu Tyr
    1010                1015                1020

Val Ser Ser Gly Glu Ala Lys Trp Gly Gln Thr Ser Lys Leu Ile
    1025                1030                1035

Leu Leu Leu Pro His Gly Tyr Glu Gly Gln Gly Pro Asp His Ser
    1040                1045                1050

Ser Ala Arg Ile Glu Arg Phe Leu Gln Leu Cys Ala Glu Gly Ser
    1055                1060                1065

Met Thr Val Ala Gln Pro Ser Thr Pro Ala Asn His Phe His Leu
    1070                1075                1080

Leu Arg Arg His Ala Leu Ser Asp Leu Lys Arg Pro Leu Val Ile
    1085                1090                1095

Phe Thr Pro Lys Ser Met Leu Arg Asn Lys Ala Ala Ala Ser Ala
    1100                1105                1110

Pro Glu Asp Phe Thr Glu Val Thr Lys Phe Gln Ser Val Ile Asp
    1115                1120                1125

Asp Pro Asn Val Ala Asp Ala Ala Lys Val Lys Lys Val Met Leu
    1130                1135                1140

Val Ser Gly Lys Leu Tyr Tyr Glu Leu Ala Lys Arg Lys Glu Lys
    1145                1150                1155

Asp Gly Arg Asp Asp Ile Ala Ile Val Arg Ile Glu Met Leu His
    1160                1165                1170

Pro Ile Pro Phe Asn Arg Ile Ser Glu Ala Leu Ala Gly Tyr Pro
    1175                1180                1185

Asn Ala Glu Glu Val Leu Phe Val Gln Asp Glu Pro Ala Asn Gln
    1190                1195                1200

Gly Pro Trp Pro Phe Tyr Gln Glu His Leu Pro Glu Leu Ile Pro
    1205                1210                1215

Asn Met Pro Lys Met Arg Arg Val Ser Arg Arg Ala Gln Ser Ser
    1220                1225                1230

Thr Ala Thr Gly Val Ala Lys Val His Gln Leu Glu Glu Lys Gln
    1235                1240                1245

Leu Ile Asp Glu Ala Phe Glu Ala
    1250                1255

<210> SEQ ID NO 46
<211> LENGTH: 4391
<212> TYPE: DNA
<213> ORGANISM: Corynebacterium glutamicum
<220> FEATURE:
<221> NAME/KEY: CDS
```

-continued

<222> LOCATION: (443)..(4210)
<223> OTHER INFORMATION: sucA805

<400> SEQUENCE: 46

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag       472
                         Met Leu Gln Leu Gly Leu Arg His Asn Gln
                           1               5                  10
```

```
cca acg acc aac gtt aca gtg gat aaa ata aag ctc aat aaa ccc tca       520
Pro Thr Thr Asn Val Thr Val Asp Lys Ile Lys Leu Asn Lys Pro Ser
                 15                  20                  25
```

```
aga agc aag gaa aag agg cga gta cct gcc gtg agc agc gct agt act       568
Arg Ser Lys Glu Lys Arg Arg Val Pro Ala Val Ser Ser Ala Ser Thr
         30                  35                  40
```

```
ttc ggc cag aat gcg tgg ctg gta gac gag atg ttc cag cag ttc cag       616
Phe Gly Gln Asn Ala Trp Leu Val Asp Glu Met Phe Gln Gln Phe Gln
 45                  50                  55
```

```
aag gac ccc aag tcc gtg gac aag gaa tgg aga gaa ctc ttt gag gcg       664
Lys Asp Pro Lys Ser Val Asp Lys Glu Trp Arg Glu Leu Phe Glu Ala
 60                  65                  70
```

```
cag ggg gga cca aat gct acc ccc gct aca aca gaa gca cag cct tca       712
Gln Gly Gly Pro Asn Ala Thr Pro Ala Thr Thr Glu Ala Gln Pro Ser
 75                  80                  85                  90
```

```
gcg ccc aag gag tct gcg aaa cca gca cca aag gct gcc cct gca gcc       760
Ala Pro Lys Glu Ser Ala Lys Pro Ala Pro Lys Ala Ala Pro Ala Ala
                 95                 100                 105
```

```
aag gca gca ccg cgc gta gaa acc aag ccg gcc gcc aag acc gcc cct       808
Lys Ala Ala Pro Arg Val Glu Thr Lys Pro Ala Ala Lys Thr Ala Pro
        110                 115                 120
```

```
aag gcc aag gag tcc tca gtg cca cag caa cct aag ctt ccg gag cca       856
Lys Ala Lys Glu Ser Ser Val Pro Gln Gln Pro Lys Leu Pro Glu Pro
125                 130                 135
```

```
gga caa acc cca atc agg ggt att ttc aag tcc atc gcg aag aac atg       904
Gly Gln Thr Pro Ile Arg Gly Ile Phe Lys Ser Ile Ala Lys Asn Met
        140                 145                 150
```

```
gat atc tcc ctg gaa atc cca acc gca acc tcg gtt cgc gat atg cca       952
Asp Ile Ser Leu Glu Ile Pro Thr Ala Thr Ser Val Arg Asp Met Pro
155                 160                 165                 170
```

```
gct cgc ctc atg ttc gaa aac cgc gcg atg gtc aac gat cag ctc aag      1000
Ala Arg Leu Met Phe Glu Asn Arg Ala Met Val Asn Asp Gln Leu Lys
                175                 180                 185
```

```
cgc acc cgc ggt ggc aag atc tcc ttc acc cac atc att ggc tac gcc      1048
Arg Thr Arg Gly Gly Lys Ile Ser Phe Thr His Ile Ile Gly Tyr Ala
        190                 195                 200
```

```
atg gtg aag gca gtc atg gct cac ccg gac atg aac aac tcc tac gac      1096
Met Val Lys Ala Val Met Ala His Pro Asp Met Asn Asn Ser Tyr Asp
205                 210                 215
```

```
gtc atc gac ggc aag cca acc ctg atc gtg cct gag cac atc aac ctg      1144
Val Ile Asp Gly Lys Pro Thr Leu Ile Val Pro Glu His Ile Asn Leu
220                 225                 230
```

```
ggc ctt gcc atc gac ctt cct cag aag gac ggc tcc cgc gca ctt gtc      1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc      1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc      1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
    300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat      1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
    380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac      1768
Pro Leu Ser Trp Val Gln Pro Gly Met Pro Val Pro Asp His Arg Asp
            430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
        445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
    460                 465                 470 gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc      1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc      2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc      2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gct ctc      2104
Lys Tyr Val Gly Gln Lys Arg Phe Ser Leu Glu Gly Ala Glu Ala Leu
    540                 545                 550
```

-continued

```
atc cca ctg atg gac tcc gcc atc gac acc gcc gca ggc cag ggc ctc      2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg      2200
Asp Glu Val Val Ile Gly Met Pro His Arg Gly Arg Leu Asn Val Leu
            575                 580                 585 ttc aac atc gtg ggc aag cca ctg gca tcc atc ttc aac gag ttt gaa      2248
Phe Asn Ile Val Gly Lys Pro Leu Ala Ser Ile Phe Asn Glu Phe Glu
        590                 595                 600 ggc caa atg gag cag ggc cag atc ggt ggc tcc ggt gac gtg aag tac      2296
Gly Gln Met Glu Gln Gly Gln Ile Gly Gly Ser Gly Asp Val Lys Tyr
    605                 610                 615 cac ctc ggt tcc gaa ggc cag cac ctg cag atg ttc ggc gac ggc gag      2344
His Leu Gly Ser Glu Gly Gln His Leu Gln Met Phe Gly Asp Gly Glu
620                 625                 630 atc aag gtc tcc ctg act gct aac ccg tcc cac ctg gaa gct gtt aac      2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag      2440
Pro Val Met Glu Gly Ile Val Arg Ala Lys Gln Asp Tyr Leu Asp Lys
            655                 660                 665 ggc gta gac ggc aag act gtt gtg cca ctg ctc ctc cac ggt gac gct      2488
Gly Val Asp Gly Lys Thr Val Val Pro Leu Leu Leu His Gly Asp Ala
        670                 675                 680 gca ttc gca ggc ctg ggc atc gtg cca gaa acc atc aac ctg gct aaa      2536
Ala Phe Ala Gly Leu Gly Ile Val Pro Glu Thr Ile Asn Leu Ala Lys
    685                 690                 695 agc tgc gtc gac gtc gga ggc acc atc cac atc gtg gtg aac aac cag      2584
Ser Cys Val Asp Val Gly Gly Thr Ile His Ile Val Val Asn Asn Gln
700                 705                 710 atc ggc ttc acc acc acc cca gac tcc agc cgc tcc atg cac tac gca      2632
Ile Gly Phe Thr Thr Thr Pro Asp Ser Ser Arg Ser Met His Tyr Ala
715                 720                 725                 730 acc gac tac gcc aag gca ttc ggc tgc cca gtc ttc cac gtc aat ggt      2680
Thr Asp Tyr Ala Lys Ala Phe Gly Cys Pro Val Phe His Val Asn Gly
            735                 740                 745 gat gac cca gag gca gtt gtc tgg gtt ggc cag ctg gca acc gag tac      2728
Asp Asp Pro Glu Ala Val Val Trp Val Gly Gln Leu Ala Thr Glu Tyr
        750                 755                 760 cgt cgt cgc ttc ggc aag gac gtc ttc atc gac ctc gtt tgc tac cgc      2776
Arg Arg Arg Phe Gly Lys Asp Val Phe Ile Asp Leu Val Cys Tyr Arg
    765                 770                 775 ctc cgc ggc cac aac gaa gct gat gat cct tcc atg acc cag cca aag      2824
Leu Arg Gly His Asn Glu Ala Asp Asp Pro Ser Met Thr Gln Pro Lys
780                 785                 790 atg tat gag ctc atc acc ggc cgc gag acc gtt cgt gct cag tac acc      2872
Met Tyr Glu Leu Ile Thr Gly Arg Glu Thr Val Arg Ala Gln Tyr Thr
795                 800                 805                 810 gaa gac ctg ctc gga cgt gga gac ctc tcc aac gaa gat gca gaa gca      2920
Glu Asp Leu Leu Gly Arg Gly Asp Leu Ser Asn Glu Asp Ala Glu Ala
            815                 820                 825 gtc gtc cgc gac ttc cac gac cag atg gaa tct gtg ttc aac gaa gtc      2968
Val Val Arg Asp Phe His Asp Gln Met Glu Ser Val Phe Asn Glu Val
        830                 835                 840 aag gaa ggc ggc aag aag cag gct gag gca cag acc ggc atc acc ggc      3016
Lys Glu Gly Gly Lys Lys Gln Ala Glu Ala Gln Thr Gly Ile Thr Gly
    845                 850                 855 tcc cag aag ctt cca cac ggc ctt gag acc aac atc tcc cgt gaa gag      3064
Ser Gln Lys Leu Pro His Gly Leu Glu Thr Asn Ile Ser Arg Glu Glu
```

-continued

```
            860                 865                 870
ctc ctg gaa ctg gga cag gct ttc gcc aac acc cca gaa ggc ttc aac    3112
Leu Leu Glu Leu Gly Gln Ala Phe Ala Asn Thr Pro Glu Gly Phe Asn
875                 880                 885                 890 tac cac cca cgt gtg gct cca gtt gct aag aag cgc gtc tcc tct gtc    3160
Tyr His Pro Arg Val Ala Pro Val Ala Lys Lys Arg Val Ser Ser Val
                895                 900                 905 acc gaa ggt ggc atc gac tgg gca tgg ggc gag ctc ctc gcc ttc ggt    3208
Thr Glu Gly Gly Ile Asp Trp Ala Trp Gly Glu Leu Leu Ala Phe Gly
            910                 915                 920 tcc ctg gct aac tcc ggc cgc ttg gtt cgc ctt gca ggt gaa gat tcc    3256
Ser Leu Ala Asn Ser Gly Arg Leu Val Arg Leu Ala Gly Glu Asp Ser
                925                 930                 935 cgc cgc ggt acc ttc acc cag cgc cac gca gtt gcc atc gac cca gcg    3304
Arg Arg Gly Thr Phe Thr Gln Arg His Ala Val Ala Ile Asp Pro Ala
            940                 945                 950 acc gct gaa gag ttc aac cca ctc cac gag ctt gca cag tcc aag ggc    3352
Thr Ala Glu Glu Phe Asn Pro Leu His Glu Leu Ala Gln Ser Lys Gly
955                 960                 965                 970 aac aac ggt aag ttc ctg gtc tac aac tcc gca ctg acc gag tac gca    3400
Asn Asn Gly Lys Phe Leu Val Tyr Asn Ser Ala Leu Thr Glu Tyr Ala
                975                 980                 985 ggc atg ggc ttc gag tac ggc tac tcc gta gga aac gaa gac tcc gtc    3448
Gly Met Gly Phe Glu Tyr Gly Tyr Ser Val Gly Asn Glu Asp Ser Val
            990                 995                 1000 gtt gca tgg gaa gca cag ttc ggc gac ttc gcc aac ggc gct cag        3493
Val Ala Trp Glu Ala Gln Phe Gly Asp Phe Ala Asn Gly Ala Gln
                1005                1010                1015 acc atc atc gat gag tac gtc tcc tca ggc gaa gct aag tgg ggc        3538
Thr Ile Ile Asp Glu Tyr Val Ser Ser Gly Glu Ala Lys Trp Gly
        1020                1025                1030 cag acc tcc aag ctg atc ctt ctg ctg cct cac ggc tac gaa ggc        3583
Gln Thr Ser Lys Leu Ile Leu Leu Leu Pro His Gly Tyr Glu Gly
    1035                1040                1045 cag ggc cca gac cac tct tcc gca cgt atc gag cgc ttc ctg cag        3628
Gln Gly Pro Asp His Ser Ser Ala Arg Ile Glu Arg Phe Leu Gln
    1050                1055                1060 ctg tgc gct gag ggt tcc atg act gtt gct cag cca tcc acc cca        3673
Leu Cys Ala Glu Gly Ser Met Thr Val Ala Gln Pro Ser Thr Pro
    1065                1070                1075 gca aac cac ttc cac ctg ctg cgt cgt cac gct ctg tcc gac ctg        3718
Ala Asn His Phe His Leu Leu Arg Arg His Ala Leu Ser Asp Leu
    1080                1085                1090 aag cgt cca ctg gtt atc ttc acc ccg aag tcc atg ctg cgt aac        3763
Lys Arg Pro Leu Val Ile Phe Thr Pro Lys Ser Met Leu Arg Asn
    1095                1100                1105 aag gct gct gcc tcc gca cca gaa gac ttc act gag gtc acc aag        3808
Lys Ala Ala Ala Ser Ala Pro Glu Asp Phe Thr Glu Val Thr Lys
    1110                1115                1120 ttc caa tcc gtg atc gac gat cca aac gtt gca gat gca gcc aag        3853
Phe Gln Ser Val Ile Asp Asp Pro Asn Val Ala Asp Ala Ala Lys
    1125                1130                1135 gtg aag aag gtc atg ctg gtc tcc ggc aag ctg tac tac gaa ttg        3898
Val Lys Lys Val Met Leu Val Ser Gly Lys Leu Tyr Tyr Glu Leu
    1140                1145                1150 gca aag cgc aag gag aag gac gga cgc gac gac atc gcg atc gtt        3943
Ala Lys Arg Lys Glu Lys Asp Gly Arg Asp Asp Ile Ala Ile Val
    1155                1160                1165 cgt atc gaa atg ctc cac cca att ccg ttc aac cgc atc tcc gag        3988
```

```
Arg Ile Glu Met Leu His Pro Ile Pro Phe Asn Arg Ile Ser Glu
        1170                1175                1180 gct ctt gcc ggc tac cct aac gct gag gaa gtc ctc ttc gtt cag      4033
Ala Leu Ala Gly Tyr Pro Asn Ala Glu Glu Val Leu Phe Val Gln
        1185                1190                1195 gat gag cca gca aac cag ggc cca tgg ccg ttc tac cag gag cac      4078
Asp Glu Pro Ala Asn Gln Gly Pro Trp Pro Phe Tyr Gln Glu His
        1200                1205                1210 ctc cca gag ctg atc ccg aac atg cca aag atg cgc cgc gtt tcc      4123
Leu Pro Glu Leu Ile Pro Asn Met Pro Lys Met Arg Arg Val Ser
        1215                1220                1225 cgc cgc gct cag tcc tcc acc gca act ggt gtt gct aag gtg cac      4168
Arg Arg Ala Gln Ser Ser Thr Ala Thr Gly Val Ala Lys Val His
        1230                1235                1240 cag ctg gag gag aag cag ctt atc gac gag gct ttc gag gct          4210
Gln Leu Glu Glu Lys Gln Leu Ile Asp Glu Ala Phe Glu Ala
        1245                1250                1255 taagtcttta tagtcctgca ctagcctaga gggccttatg cagtgtgaat cacacagcat      4270
aaggcccttt tgctgccgt ggttgcctaa ggtggaaggc atgaaacgaa tctgtgcggt      4330
cacgatctct tcagtacttt tgctaagtgg ctgctcctcc acttccacca cgcagctcga      4390
g                                                                      4391

<210> SEQ ID NO 47
<211> LENGTH: 1256
<212> TYPE: PRT
<213> ORGANISM: Corynebacterium glutamicum

<400> SEQUENCE: 47

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
```

```
                   210                 215                 220
Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
                260                 265                 270

Val Thr Arg Ser Arg Lys Gly Lys Leu Thr Met Asp Asp Tyr Gln Gly
            275                 280                 285

Val Thr Val Ser Leu Thr Asn Pro Gly Gly Ile Gly Thr Arg His Ser
            290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
                340                 345                 350

Arg Val Ile Gln Gly Ala Val Ser Gly Glu Phe Leu Arg Thr Met Ser
            355                 360                 365

Arg Leu Leu Thr Asp Asp Ser Phe Trp Asp Glu Ile Phe Asp Ala Met
            370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
                420                 425                 430

Pro Gly Met Pro Val Pro Asp His Arg Asp Leu Asp Ile Glu Thr His
            435                 440                 445

Ser Leu Thr Ile Trp Asp Leu Asp Arg Thr Phe Ser Val Gly Gly Phe
            450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
                500                 505                 510

Lys Pro Thr Gln Ala Glu Gln Lys Tyr Ile Leu Gln Lys Leu Asn Ala
            515                 520                 525

Ala Glu Ala Phe Glu Asn Phe Leu Gln Thr Lys Tyr Val Gly Gln Lys
            530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
                580                 585                 590

Pro Leu Ala Ser Ile Phe Asn Glu Phe Glu Gly Gln Met Glu Gln Gly
            595                 600                 605

Gln Ile Gly Gly Ser Gly Asp Val Lys Tyr His Leu Gly Ser Glu Gly
            610                 615                 620

Gln His Leu Gln Met Phe Gly Asp Gly Glu Ile Lys Val Ser Leu Thr
625                 630                 635                 640
```

-continued

```
Ala Asn Pro Ser His Leu Glu Ala Val Asn Pro Val Met Glu Gly Ile
            645                 650                 655
Val Arg Ala Lys Gln Asp Tyr Leu Asp Lys Gly Val Asp Gly Lys Thr
        660                 665                 670
Val Val Pro Leu Leu His Gly Asp Ala Ala Phe Ala Gly Leu Gly
    675                 680                 685
Ile Val Pro Glu Thr Ile Asn Leu Ala Lys Ser Cys Val Asp Val Gly
690                 695                 700
Gly Thr Ile His Ile Val Val Asn Asn Gln Ile Gly Phe Thr Thr Thr
705                 710                 715                 720
Pro Asp Ser Ser Arg Ser Met His Tyr Ala Thr Asp Tyr Ala Lys Ala
                725                 730                 735
Phe Gly Cys Pro Val Phe His Val Asn Gly Asp Asp Pro Glu Ala Val
            740                 745                 750
Val Trp Val Gly Gln Leu Ala Thr Glu Tyr Arg Arg Arg Phe Gly Lys
        755                 760                 765
Asp Val Phe Ile Asp Leu Val Cys Tyr Arg Leu Arg Gly His Asn Glu
770                 775                 780
Ala Asp Asp Pro Ser Met Thr Gln Pro Lys Met Tyr Glu Leu Ile Thr
785                 790                 795                 800
Gly Arg Glu Thr Val Arg Ala Gln Tyr Thr Glu Asp Leu Leu Gly Arg
                805                 810                 815
Gly Asp Leu Ser Asn Glu Asp Ala Glu Ala Val Val Arg Asp Phe His
            820                 825                 830
Asp Gln Met Glu Ser Val Phe Asn Glu Val Lys Glu Gly Gly Lys Lys
        835                 840                 845
Gln Ala Glu Ala Gln Thr Gly Ile Thr Gly Ser Gln Lys Leu Pro His
    850                 855                 860
Gly Leu Glu Thr Asn Ile Ser Arg Glu Glu Leu Leu Glu Leu Gly Gln
865                 870                 875                 880
Ala Phe Ala Asn Thr Pro Glu Gly Phe Asn Tyr His Pro Arg Val Ala
                885                 890                 895
Pro Val Ala Lys Lys Arg Val Ser Ser Val Thr Glu Gly Gly Ile Asp
            900                 905                 910
Trp Ala Trp Gly Glu Leu Leu Ala Phe Gly Ser Leu Ala Asn Ser Gly
        915                 920                 925
Arg Leu Val Arg Leu Ala Gly Glu Asp Ser Arg Arg Gly Thr Phe Thr
    930                 935                 940
Gln Arg His Ala Val Ala Ile Asp Pro Ala Thr Ala Glu Glu Phe Asn
945                 950                 955                 960
Pro Leu His Glu Leu Ala Gln Ser Lys Gly Asn Asn Gly Lys Phe Leu
                965                 970                 975
Val Tyr Asn Ser Ala Leu Thr Glu Tyr Ala Gly Met Gly Phe Glu Tyr
            980                 985                 990
Gly Tyr Ser Val Gly Asn Glu Asp  Ser Val Val Ala Trp Glu Ala Gln
        995                 1000                1005
Phe Gly  Asp Phe Ala Asn Gly  Ala Gln Thr Ile Ile  Asp Glu Tyr
    1010                1015                1020
Val Ser  Ser Gly Glu Ala Lys  Trp Gly Gln Thr Ser  Lys Leu Ile
    1025                1030                1035
Leu Leu  Leu Pro His Gly Tyr  Glu Gly Gln Gly Pro  Asp His Ser
    1040                1045                1050
```

-continued

```
Ser Ala Arg Ile Glu Arg Phe Leu Gln Leu Cys Ala Glu Gly Ser
    1055                1060                1065

Met Thr Val Ala Gln Pro Ser Thr Pro Ala Asn His Phe His Leu
    1070                1075                1080

Leu Arg Arg His Ala Leu Ser Asp Leu Lys Arg Pro Leu Val Ile
    1085                1090                1095

Phe Thr Pro Lys Ser Met Leu Arg Asn Lys Ala Ala Ala Ser Ala
    1100                1105                1110

Pro Glu Asp Phe Thr Glu Val Thr Lys Phe Gln Ser Val Ile Asp
    1115                1120                1125

Asp Pro Asn Val Ala Asp Ala Lys Val Lys Lys Val Met Leu
    1130                1135                1140

Val Ser Gly Lys Leu Tyr Tyr Glu Leu Ala Lys Arg Lys Glu Lys
    1145                1150                1155

Asp Gly Arg Asp Asp Ile Ala Ile Val Arg Ile Glu Met Leu His
    1160                1165                1170

Pro Ile Pro Phe Asn Arg Ile Ser Glu Ala Leu Ala Gly Tyr Pro
    1175                1180                1185

Asn Ala Glu Glu Val Leu Phe Val Gln Asp Glu Pro Ala Asn Gln
    1190                1195                1200

Gly Pro Trp Pro Phe Tyr Gln Glu His Leu Pro Glu Leu Ile Pro
    1205                1210                1215

Asn Met Pro Lys Met Arg Arg Val Ser Arg Arg Ala Gln Ser Ser
    1220                1225                1230

Thr Ala Thr Gly Val Ala Lys Val His Gln Leu Glu Glu Lys Gln
    1235                1240                1245

Leu Ile Asp Glu Ala Phe Glu Ala
    1250                1255
```

<210> SEQ ID NO 48
<211> LENGTH: 4391
<212> TYPE: DNA
<213> ORGANISM: Corynebacterium glutamicum
<220> FEATURE:
<221> NAME/KEY: CDS
<222> LOCATION: (443)..(4210)

<400> SEQUENCE: 48

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag     472
                          Met Leu Gln Leu Gly Leu Arg His Asn Gln
                           1               5                  10 cca acg acc aac gtt aca gtg gat aaa ata aag ctc aat aaa ccc tca     520
Pro Thr Thr Asn Val Thr Val Asp Lys Ile Lys Leu Asn Lys Pro Ser
                15                  20                  25 aga agc aag gaa aag agg cga gta cct gcc gtg agc agc gct agt act     568
Arg Ser Lys Glu Lys Arg Arg Val Pro Ala Val Ser Ser Ala Ser Thr
        30                  35                  40
```

```
ttc ggc cag aat gcg tgg ctg gta gac gag atg ttc cag cag ttc cag      616
Phe Gly Gln Asn Ala Trp Leu Val Asp Glu Met Phe Gln Gln Phe Gln
         45                  50                  55 aag gac ccc aag tcc gtg gac aag gaa tgg aga gaa ctc ttt gag gcg      664
Lys Asp Pro Lys Ser Val Asp Lys Glu Trp Arg Glu Leu Phe Glu Ala
 60                  65                  70 cag ggg gga cca aat gct acc ccc gct aca aca gaa gca cag cct tca      712
Gln Gly Gly Pro Asn Ala Thr Pro Ala Thr Thr Glu Ala Gln Pro Ser
 75                  80                  85                  90 gcg ccc aag gag tct gcg aaa cca gca cca aag gct gcc cct gca gcc      760
Ala Pro Lys Glu Ser Ala Lys Pro Ala Pro Lys Ala Ala Pro Ala Ala
                 95                 100                 105 aag gca gca ccg cgc gta gaa acc aag ccg gcc gcc aag acc gcc cct      808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca      856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
    140                 145                 150 gat atc tcc ctg gaa atc cca acc gca acc tcg gtt cgc gat atg cca      952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag     1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc     1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac     1096
Met Val Lys Ala Val Met Ala His Pro Asp Met Asn Asn Ser Tyr Asp
        205                 210                 215 gtc atc gac ggc aag cca acc ctg atc gtg cct gag cac atc aac ctg     1144
Val Ile Asp Gly Lys Pro Thr Leu Ile Val Pro Glu His Ile Asn Leu
    220                 225                 230 ggc ctt gcc atc gac ctt cct cag aag gac ggc tcc cgc gca ctt gtc     1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc     1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc     1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc     1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc     1384
Ile Gly Thr Arg His Ser Val Pro Arg Leu Thr Lys Gly Gln Gly Thr
    300                 305                 310 atc atc ggt gtc ggt tcc atg gat tac cca gca gag ttc cag ggc gct     1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc     1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa     1528
Thr Ser Thr Tyr Asp His Arg Val Ile Gln Gly Ala Val Ser Gly Glu
            350                 355                 360
```

-continued

| | | |
|---|---|---|
| ttc ctg cgt acc atg tct cgc ctg ctc acc gat gat tcc ttc tgg gat<br>Phe Leu Arg Thr Met Ser Arg Leu Leu Thr Asp Asp Ser Phe Trp Asp<br>365                                 370                         375 | 1576 |
| gag atc ttc gac gca atg aac gtt cct tac acc cca atg cgt tgg gca<br>Glu Ile Phe Asp Ala Met Asn Val Pro Tyr Thr Pro Met Arg Trp Ala<br>380                               385                           390 | 1624 |
| cag gac gtt cca aac acc ggt gtt gat aag aac acc cgc gtc atg cag<br>Gln Asp Val Pro Asn Thr Gly Val Asp Lys Asn Thr Arg Val Met Gln<br>395                           400                         405                      410 | 1672 |
| ctc att gag gca tac cgc tcc cgt gga cac ctc atc gct gac acc aac<br>Leu Ile Glu Ala Tyr Arg Ser Arg Gly His Leu Ile Ala Asp Thr Asn<br>                       415                         420                         425 | 1720 |
| cca ctt tca tgg gtt cag cct ggc atg cca gtt cca gac cac cgc gac<br>Pro Leu Ser Trp Val Gln Pro Gly Met Pro Val Pro Asp His Arg Asp<br>                  430                         435                         440 | 1768 |
| ctc gac atc gag acc cac agc ctg acc atc tgg gat ctg gac cgt acc<br>Leu Asp Ile Glu Thr His Ser Leu Thr Ile Trp Asp Leu Asp Arg Thr<br>                       445                         450                         455 | 1816 |
| ttc agc gtc ggt ggc ttc ggc ggc aag gag acc atg acc ctg cgc gag<br>Phe Ser Val Gly Gly Phe Gly Gly Lys Glu Thr Met Thr Leu Arg Glu<br>460                               465                         470 | 1864 |
| gta ctg tcc cgc ctg cgc gct gcc tac acc ttg aag gtc ggc tcc gaa<br>Val Leu Ser Arg Leu Arg Ala Ala Tyr Thr Leu Lys Val Gly Ser Glu<br>475                             480                         485                      490 | 1912 |
| tac acc cac atc ctg gac cgc gac gag cgc acc tgg ctg cag gac cgc<br>Tyr Thr His Ile Leu Asp Arg Asp Glu Arg Thr Trp Leu Gln Asp Arg<br>                       495                         500                         505 | 1960 |
| ctc gaa gcc gga atg cca aag cca acc cag gca gag cag aag tac atc<br>Leu Glu Ala Gly Met Pro Lys Pro Thr Gln Ala Glu Gln Lys Tyr Ile<br>                  510                         515                         520 | 2008 |
| ctg cag aag ctg aac gcc gca gag gct ttc gag aac ttc ctg cag acc<br>Leu Gln Lys Leu Asn Ala Ala Glu Ala Phe Glu Asn Phe Leu Gln Thr<br>525                               530                         535 | 2056 |
| aag tac gtc ggc cag aag cgc ttc tcc ctc gaa ggt gca gaa gct ctc<br>Lys Tyr Val Gly Gln Lys Arg Phe Ser Leu Glu Gly Ala Glu Ala Leu<br>540                               545                         550 | 2104 |
| atc cca ctg atg gac tcc gcc atc gac acc gcc gca ggc cag ggc ctc<br>Ile Pro Leu Met Asp Ser Ala Ile Asp Thr Ala Ala Gly Gln Gly Leu<br>555                           560                         565                      570 | 2152 |
| gac gaa gtt gtc atc ggt atg cca cac cgt ggt cgc ctc aac gtg ctg<br>Asp Glu Val Val Ile Gly Met Pro His Arg Gly Arg Leu Asn Val Leu<br>                       575                         580                         585 | 2200 |
| ttc aac atc gtg ggc aag cca ctg gca tcc atc ttc aac gag ttt gaa<br>Phe Asn Ile Val Gly Lys Pro Leu Ala Ser Ile Phe Asn Glu Phe Glu<br>                  590                         595                         600 | 2248 |
| ggc caa atg gag cag ggc cag atc ggt ggc tcc ggt gac gtg aag tac<br>Gly Gln Met Glu Gln Gly Gln Ile Gly Gly Ser Gly Asp Val Lys Tyr<br>                       605                         610                         615 | 2296 |
| cac ctc ggt tcc gaa ggc cag cac ctg cag atg ttc ggc gac ggc gag<br>His Leu Gly Ser Glu Gly Gln His Leu Gln Met Phe Gly Asp Gly Glu<br>620                             625                         630 | 2344 |
| atc aag gtc tcc ctg act gct aac ccg tcc cac ctg gaa gct gtt aac<br>Ile Lys Val Ser Leu Thr Ala Asn Pro Ser His Leu Glu Ala Val Asn<br>635                             640                         645                      650 | 2392 |
| cca gtg atg gaa ggt atc gtc cgc gca aag cag gac tac ctg gac aag<br>Pro Val Met Glu Gly Ile Val Arg Ala Lys Gln Asp Tyr Leu Asp Lys<br>                       655                         660                         665 | 2440 |
| ggc gta gac ggc aag act gtt gtg cca ctg ctc ctc cac ggt gac gct<br>Gly Val Asp Gly Lys Thr Val Val Pro Leu Leu Leu His Gly Asp Ala | 2488 |

-continued

| | | |
|---|---|---|
| gca ttc gca ggc ctg ggc atc gtg cca gaa acc atc aac ctg gct ata<br>Ala Phe Ala Gly Leu Gly Ile Val Pro Glu Thr Ile Asn Leu Ala Ile<br>685                                          690                                695 | 2536 |
| agc tgc gtc gac gtc gga ggc acc atc cac atc gtg gtg aac aac cag<br>Ser Cys Val Asp Val Gly Gly Thr Ile His Ile Val Val Asn Asn Gln<br>700                                          705                                710 | 2584 |
| atc ggc ttc acc acc acc cca gac tcc agc cgc tcc atg cac tac gca<br>Ile Gly Phe Thr Thr Thr Pro Asp Ser Ser Arg Ser Met His Tyr Ala<br>715                                        720                                725                        730 | 2632 |
| acc gac tac gcc aag gca ttc ggc tgc cca gtc ttc cac gtc aat ggt<br>Thr Asp Tyr Ala Lys Ala Phe Gly Cys Pro Val Phe His Val Asn Gly<br>                              735                                740                                745 | 2680 |
| gat gac cca gag gca gtt gtc tgg gtt ggc cag ctg gca acc gag tac<br>Asp Asp Pro Glu Ala Val Val Trp Val Gly Gln Leu Ala Thr Glu Tyr<br>750                                      755                                760 | 2728 |
| cgt cgt cgc ttc ggc aag gac gtc ttc atc gac ctc gtt tgc tac cgc<br>Arg Arg Arg Phe Gly Lys Asp Val Phe Ile Asp Leu Val Cys Tyr Arg<br>                              765                                770                                775 | 2776 |
| ctc cgc ggc cac aac gaa gct gat gat cct tcc atg acc cag cca aag<br>Leu Arg Gly His Asn Glu Ala Asp Asp Pro Ser Met Thr Gln Pro Lys<br>780                                      785                                790 | 2824 |
| atg tat gag ctc atc acc ggc cgc gag acc gtt cgt gct cag tac acc<br>Met Tyr Glu Leu Ile Thr Gly Arg Glu Thr Val Arg Ala Gln Tyr Thr<br>795                                  800                                805                        810 | 2872 |
| gaa gac ctg ctc gga cgt gga gac ctc tcc aac gaa gat gca gaa gca<br>Glu Asp Leu Leu Gly Arg Gly Asp Leu Ser Asn Glu Asp Ala Glu Ala<br>                              815                                820                                825 | 2920 |
| gtc gtc cgc gac ttc cac gac cag atg gaa tct gtg ttc aac gaa gtc<br>Val Val Arg Asp Phe His Asp Gln Met Glu Ser Val Phe Asn Glu Val<br>                              830                                835                                840 | 2968 |
| aag gaa ggc ggc aag aag cag gct gag gca cag acc ggc atc acc ggc<br>Lys Glu Gly Gly Lys Lys Gln Ala Glu Ala Gln Thr Gly Ile Thr Gly<br>                              845                                850                                855 | 3016 |
| tcc cag aag ctt cca cac ggc ctt gag acc aac atc tcc cgt gaa gag<br>Ser Gln Lys Leu Pro His Gly Leu Glu Thr Asn Ile Ser Arg Glu Glu<br>860                                      865                                870 | 3064 |
| ctc ctg gaa ctg gga cag gct ttc gcc aac acc cca gaa ggc ttc aac<br>Leu Leu Glu Leu Gly Gln Ala Phe Ala Asn Thr Pro Glu Gly Phe Asn<br>875                                      880                                885                        890 | 3112 |
| tac cac cca cgt gtg gct cca gtt gct aag aag cgc gtc tcc tct gtc<br>Tyr His Pro Arg Val Ala Pro Val Ala Lys Lys Arg Val Ser Ser Val<br>                              895                                900                                905 | 3160 |
| acc gaa ggt ggc atc gac tgg gca tgg ggc gag ctc ctc gcc ttc ggt<br>Thr Glu Gly Gly Ile Asp Trp Ala Trp Gly Glu Leu Leu Ala Phe Gly<br>                              910                                915                                920 | 3208 |
| tcc ctg gct aac tcc ggc cgc ttg gtt cgc ctt gca ggt gaa gat tcc<br>Ser Leu Ala Asn Ser Gly Arg Leu Val Arg Leu Ala Gly Glu Asp Ser<br>                              925                                930                                935 | 3256 |
| cgc cgc ggt acc ttc acc cag cgc cac gca gtt gcc atc gac cca gcg<br>Arg Arg Gly Thr Phe Thr Gln Arg His Ala Val Ala Ile Asp Pro Ala<br>940                                      945                                950 | 3304 |
| acc gct gaa gag ttc aac cca ctc cac gag ctt gca cag tcc aag ggc<br>Thr Ala Glu Glu Phe Asn Pro Leu His Glu Leu Ala Gln Ser Lys Gly<br>955                                      960                                965                        970 | 3352 |
| aac aac ggt aag ttc ctg gtc tac aac tcc gca ctg acc gag tac gca<br>Asn Asn Gly Lys Phe Leu Val Tyr Asn Ser Ala Leu Thr Glu Tyr Ala<br>                              975                                980                                985 | 3400 |
| ggc atg ggc ttc gag tac ggc tac tcc gta gga aac gaa gac tcc gtc | 3448 |

```
                                                              -continued

Gly Met Gly Phe Glu Tyr Gly Tyr Ser Val Gly Asn Glu Asp  Ser Val
            990             995             1000 gtt gca tgg gaa gca cag ttc ggc gac ttc gcc aac ggc gct cag          3493
Val Ala Trp Glu Ala Gln Phe Gly Asp Phe Ala Asn Gly Ala Gln
        1005            1010            1015 acc atc atc gat gag tac gtc tcc tca ggc gaa gct aag tgg ggc          3538
Thr Ile Ile Asp Glu Tyr Val Ser Ser Gly Glu Ala Lys Trp Gly
        1020            1025            1030 cag acc tcc aag ctg atc ctt ctg ctg cct cac ggc tac gaa ggc          3583
Gln Thr Ser Lys Leu Ile Leu Leu Leu Pro His Gly Tyr Glu Gly
        1035            1040            1045 cag ggc cca gac cac tct tcc gca cgt atc gag cgc ttc ctg cag          3628
Gln Gly Pro Asp His Ser Ser Ala Arg Ile Glu Arg Phe Leu Gln
        1050            1055            1060 ctg tgc gct gag ggt tcc atg act gtt gct cag cca tcc acc cca          3673
Leu Cys Ala Glu Gly Ser Met Thr Val Ala Gln Pro Ser Thr Pro
        1065            1070            1075 gca aac cac ttc cac ctg ctg cgt cgt cac gct ctg tcc gac ctg          3718
Ala Asn His Phe His Leu Leu Arg Arg His Ala Leu Ser Asp Leu
        1080            1085            1090 aag cgt cca ctg gtt atc ttc acc ccg aag tcc atg ctg cgt aac          3763
Lys Arg Pro Leu Val Ile Phe Thr Pro Lys Ser Met Leu Arg Asn
        1095            1100            1105 aag gct gct gcc tcc gca cca gaa gac ttc act gag gtc acc aag          3808
Lys Ala Ala Ala Ser Ala Pro Glu Asp Phe Thr Glu Val Thr Lys
        1110            1115            1120 ttc caa tcc gtg atc gac gat cca aac gtt gca gat gca gcc aag          3853
Phe Gln Ser Val Ile Asp Asp Pro Asn Val Ala Asp Ala Ala Lys
        1125            1130            1135 gtg aag aag gtc atg ctg gtc tcc ggc aag ctg tac tac gaa ttg          3898
Val Lys Lys Val Met Leu Val Ser Gly Lys Leu Tyr Tyr Glu Leu
        1140            1145            1150 gca aag cgc aag gag aag gac gga cgc gac gac atc gcg atc gtt          3943
Ala Lys Arg Lys Glu Lys Asp Gly Arg Asp Asp Ile Ala Ile Val
        1155            1160            1165 cgt atc gaa atg ctc cac cca att ccg ttc aac cgc atc tcc gag          3988
Arg Ile Glu Met Leu His Pro Ile Pro Phe Asn Arg Ile Ser Glu
        1170            1175            1180 gct ctt gcc ggc tac cct aac gct gag gaa gtc ctc ttc gtt cag          4033
Ala Leu Ala Gly Tyr Pro Asn Ala Glu Glu Val Leu Phe Val Gln
        1185            1190            1195 gat gag cca gca aac cag ggc cca tgg ccg ttc tac cag gag cac          4078
Asp Glu Pro Ala Asn Gln Gly Pro Trp Pro Phe Tyr Gln Glu His
        1200            1205            1210 ctc cca gag ctg atc ccg aac atg cca aag atg cgc cgc gtt tcc          4123
Leu Pro Glu Leu Ile Pro Asn Met Pro Lys Met Arg Arg Val Ser
        1215            1220            1225 cgc cgc gct cag tcc tcc acc gca act ggt gtt gct aag gtg cac          4168
Arg Arg Ala Gln Ser Ser Thr Ala Thr Gly Val Ala Lys Val His
        1230            1235            1240 cag ctg gag gag aag cag ctt atc gac gag gct ttc gag gct              4210
Gln Leu Glu Glu Lys Gln Leu Ile Asp Glu Ala Phe Glu Ala
        1245            1250            1255 taagtctttta tagtcctgca ctagcctaga gggccttatg cagtgtgaat cacacagcat   4270
aaggcccttt ttgctgccgt ggttgcctaa ggtggaaggc atgaaacgaa tctgtgcggt    4330
cacgatctct tcagtacttt tgctaagtgg ctgctcctcc acttccacca cgcagctcga   4390
g                                                                   4391
```

-continued

```
<210> SEQ ID NO 49
<211> LENGTH: 1256
<212> TYPE: PRT
<213> ORGANISM: Corynebacterium glutamicum

<400> SEQUENCE: 49

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
    370                 375                 380
```

```
Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
                420                 425                 430

Pro Gly Met Pro Val Pro Asp His Arg Asp Leu Asp Ile Glu Thr His
            435                 440                 445

Ser Leu Thr Ile Trp Asp Leu Asp Arg Thr Phe Ser Val Gly Gly Phe
        450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
                500                 505                 510

Lys Pro Thr Gln Ala Glu Gln Lys Tyr Ile Leu Gln Lys Leu Asn Ala
            515                 520                 525

Ala Glu Ala Phe Glu Asn Phe Leu Gln Thr Lys Tyr Val Gly Gln Lys
        530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
            595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu His Gly Asp Ala Ala Phe Ala Gly Leu Gly
            675                 680                 685

Ile Val Pro Glu Thr Ile Asn Leu Ala Ile Ser Cys Val Asp Val Gly
        690                 695                 700

Gly Thr Ile His Ile Val Asn Asn Gln Ile Gly Phe Thr Thr Thr
705                 710                 715                 720

Pro Asp Ser Ser Arg Ser Met His Tyr Ala Thr Asp Tyr Ala Lys Ala
                725                 730                 735

Phe Gly Cys Pro Val Phe His Val Asn Gly Asp Asp Pro Glu Ala Val
            740                 745                 750

Val Trp Val Gly Gln Leu Ala Thr Glu Tyr Arg Arg Phe Gly Lys
        755                 760                 765

Asp Val Phe Ile Asp Leu Val Cys Tyr Arg Leu Arg Gly His Asn Glu
        770                 775                 780

Ala Asp Asp Pro Ser Met Thr Gln Pro Lys Met Tyr Glu Leu Ile Thr
785                 790                 795                 800
```

-continued

```
Gly Arg Glu Thr Val Arg Ala Gln Tyr Thr Glu Asp Leu Leu Gly Arg
                805                 810                 815

Gly Asp Leu Ser Asn Glu Asp Ala Glu Ala Val Val Arg Asp Phe His
            820                 825                 830

Asp Gln Met Glu Ser Val Phe Asn Glu Val Lys Glu Gly Gly Lys Lys
        835                 840                 845

Gln Ala Glu Ala Gln Thr Gly Ile Thr Gly Ser Gln Lys Leu Pro His
    850                 855                 860

Gly Leu Glu Thr Asn Ile Ser Arg Glu Glu Leu Leu Glu Leu Gly Gln
865                 870                 875                 880

Ala Phe Ala Asn Thr Pro Glu Gly Phe Asn Tyr His Pro Arg Val Ala
                885                 890                 895

Pro Val Ala Lys Lys Arg Val Ser Ser Val Thr Glu Gly Gly Ile Asp
            900                 905                 910

Trp Ala Trp Gly Glu Leu Leu Ala Phe Gly Ser Leu Ala Asn Ser Gly
        915                 920                 925

Arg Leu Val Arg Leu Ala Gly Glu Asp Ser Arg Arg Gly Thr Phe Thr
    930                 935                 940

Gln Arg His Ala Val Ala Ile Asp Pro Ala Thr Ala Glu Glu Phe Asn
945                 950                 955                 960

Pro Leu His Glu Leu Ala Gln Ser Lys Gly Asn Asn Gly Lys Phe Leu
                965                 970                 975

Val Tyr Asn Ser Ala Leu Thr Glu Tyr Ala Gly Met Gly Phe Glu Tyr
            980                 985                 990

Gly Tyr Ser Val Gly Asn Glu Asp Ser Val Val Ala Trp Glu Ala Gln
        995                 1000                1005

Phe Gly Asp Phe Ala Asn Gly Ala Gln Thr Ile Ile Asp Glu Tyr
    1010                1015                1020

Val Ser Ser Gly Glu Ala Lys Trp Gly Gln Thr Ser Lys Leu Ile
    1025                1030                1035

Leu Leu Leu Pro His Gly Tyr Glu Gly Gln Gly Pro Asp His Ser
    1040                1045                1050

Ser Ala Arg Ile Glu Arg Phe Leu Gln Leu Cys Ala Glu Gly Ser
    1055                1060                1065

Met Thr Val Ala Gln Pro Ser Thr Pro Ala Asn His Phe His Leu
    1070                1075                1080

Leu Arg Arg His Ala Leu Ser Asp Leu Lys Arg Pro Leu Val Ile
    1085                1090                1095

Phe Thr Pro Lys Ser Met Leu Arg Asn Lys Ala Ala Ala Ser Ala
    1100                1105                1110

Pro Glu Asp Phe Thr Glu Val Thr Lys Phe Gln Ser Val Ile Asp
    1115                1120                1125

Asp Pro Asn Val Ala Asp Ala Ala Lys Val Lys Lys Val Met Leu
    1130                1135                1140

Val Ser Gly Lys Leu Tyr Tyr Glu Leu Ala Lys Arg Lys Glu Lys
    1145                1150                1155

Asp Gly Arg Asp Asp Ile Ala Ile Val Arg Ile Glu Met Leu His
    1160                1165                1170

Pro Ile Pro Phe Asn Arg Ile Ser Glu Ala Leu Ala Gly Tyr Pro
    1175                1180                1185

Asn Ala Glu Glu Val Leu Phe Val Gln Asp Glu Pro Ala Asn Gln
    1190                1195                1200

Gly Pro Trp Pro Phe Tyr Gln Glu His Leu Pro Glu Leu Ile Pro
```

-continued

```
                    1205                  1210                  1215
Asn Met  Pro Lys Met Arg Arg  Val Ser Arg Arg Ala  Gln Ser Ser
         1220                  1225                  1230

Thr Ala  Thr Gly Val Ala Lys  Val His Gln Leu Glu  Glu Lys Gln
         1235                  1240                  1245

Leu Ile  Asp Glu Ala Phe Glu  Ala
         1250                  1255

<210> SEQ ID NO 50
<211> LENGTH: 3774
<212> TYPE: DNA
<213> ORGANISM: Corynebacterium glutamicum
<220> FEATURE:
<221> NAME/KEY: CDS
<222> LOCATION: (1)..(3774)

<400> SEQUENCE: 50 atg cta caa ctg ggg ctt agg cat aat cag cca acg acc aac gtt aca      48
Met Leu Gln Leu Gly Leu Arg His Asn Gln Pro Thr Thr Asn Val Thr
1               5                  10                  15 gtg gat aaa aca aag ctc aat aaa ccc tca aga agc aag gaa aag agg      96
Val Asp Lys Thr Lys Leu Asn Lys Pro Ser Arg Ser Lys Glu Lys Arg
                20                  25                  30 cga gta cct gcc gtg agc agc gct agt act ttc ggc cag aat gcg tgg     144
Arg Val Pro Ala Val Ser Ser Ala Ser Thr Phe Gly Gln Asn Ala Trp
            35                  40                  45 ctg gta gac gag atg ttc cag cag ttc cag aag gac ccc aag tcc gtg     192
Leu Val Asp Glu Met Phe Gln Gln Phe Gln Lys Asp Pro Lys Ser Val
        50                  55                  60 gac aag gaa tgg aga gaa ctc ttt gag gcg cag ggg gga cca aat act     240
Asp Lys Glu Trp Arg Glu Leu Phe Glu Ala Gln Gly Gly Pro Asn Thr
65                  70                  75                  80 acc ccc gct aca aca gaa gca cag cct tca gcg ccc aag gag tct gcg     288
Thr Pro Ala Thr Thr Glu Ala Gln Pro Ser Ala Pro Lys Glu Ser Ala
                85                  90                  95 aaa cca gca cca aag gct gcc cct gca gcc aag gca gca ccg cgc gta     336
Lys Pro Ala Pro Lys Ala Ala Pro Ala Ala Lys Ala Ala Pro Arg Val
            100                 105                 110 gaa acc aag ccg gcc gac aag acc gcc cct aag gcc aag gag tcc tca     384
Glu Thr Lys Pro Ala Asp Lys Thr Ala Pro Lys Ala Lys Glu Ser Ser
        115                 120                 125 gtg cca cag caa cct aag ctt ccg gag cca gga caa acc cca atc agg     432
Val Pro Gln Gln Pro Lys Leu Pro Glu Pro Gly Gln Thr Pro Ile Arg
130                 135                 140 ggt att ttc aag tcc atc gcg aag aac atg gat atc tcc ctg gaa atc     480
Gly Ile Phe Lys Ser Ile Ala Lys Asn Met Asp Ile Ser Leu Glu Ile
145                 150                 155                 160 cca acc gca acc tcg gtt cgc gat atg cca gct cgc ctc atg ttc gaa     528
Pro Thr Ala Thr Ser Val Arg Asp Met Pro Ala Arg Leu Met Phe Glu
                165                 170                 175 aac cgc gcg atg gtc aac gat cag ctc aag cgc acc cgc ggt ggc aag     576
Asn Arg Ala Met Val Asn Asp Gln Leu Lys Arg Thr Arg Gly Gly Lys
            180                 185                 190 atc tcc ttc acc cac atc att ggc tac gcc atg gtg aag gca gtc atg     624
Ile Ser Phe Thr His Ile Ile Gly Tyr Ala Met Val Lys Ala Val Met
        195                 200                 205 gct cac ccg gac atg aac aac tcc tac gac gtc atc gac ggc aag cca     672
Ala His Pro Asp Met Asn Asn Ser Tyr Asp Val Ile Asp Gly Lys Pro
210                 215                 220 acc ctg atc gtg cct gag cac atc aac ctg ggc ctt gct atc gac ctt     720
```

```
                                                     -continued
Thr Leu Ile Val Pro Glu His Ile Asn Leu Gly Leu Ala Ile Asp Leu
225                 230                 235                 240 cct cag aag gac ggc tcc cgc gca ctt gtc gta gca gcc atc aag gaa      768
Pro Gln Lys Asp Gly Ser Arg Ala Leu Val Val Ala Ala Ile Lys Glu
                245                 250                 255 acc gag aag atg aac ttc tcc gag ttc ctc gca gcc tac gaa gac atc      816
Thr Glu Lys Met Asn Phe Ser Glu Phe Leu Ala Ala Tyr Glu Asp Ile
            260                 265                 270 gtg gca cgc tcc cgc aag ggc aag ctc acc atg gat gac tac cag ggc      864
Val Ala Arg Ser Arg Lys Gly Lys Leu Thr Met Asp Asp Tyr Gln Gly
        275                 280                 285 gtt acc gtt tcc ttg acc aac cca ggt ggc atc ggt acc cgc cac tct      912
Val Thr Val Ser Leu Thr Asn Pro Gly Gly Ile Gly Thr Arg His Ser
    290                 295                 300 gtt cca cgt cta acc aag ggc cag ggc acc atc atc ggt gtc ggt tcc      960
Val Pro Arg Leu Thr Lys Gly Gln Gly Thr Ile Ile Gly Val Gly Ser
305                 310                 315                 320 atg gat tac cca gca gag ttc cag ggc gct tca gaa gac cgc ctt gca     1008
Met Asp Tyr Pro Ala Glu Phe Gln Gly Ala Ser Glu Asp Arg Leu Ala
                325                 330                 335 gag ctc ggc gtt ggc aaa ctt gtc acc atc acc tcc acc tac gat cac     1056
Glu Leu Gly Val Gly Lys Leu Val Thr Ile Thr Ser Thr Tyr Asp His
            340                 345                 350 cgc gtg atc cag ggt gct gtg tcc ggt gaa ttc ctg cgc acc atg tct     1104
Arg Val Ile Gln Gly Ala Val Ser Gly Glu Phe Leu Arg Thr Met Ser
        355                 360                 365 cgc ctg ctc acc gat gat tcc ttc tgg gat gag atc ttc gac gca atg     1152
Arg Leu Leu Thr Asp Asp Ser Phe Trp Asp Glu Ile Phe Asp Ala Met
370                 375                 380 aac gtt cct tac acc cca atg cgt tgg gca cag gac gtt cca aac acc     1200
Asn Val Pro Tyr Thr Pro Met Arg Trp Ala Gln Asp Val Pro Asn Thr
385                 390                 395                 400 ggt gtt gat aag aac acc cgc gtc atg cag ctc att gag gca tac cgc     1248
Gly Val Asp Lys Asn Thr Arg Val Met Gln Leu Ile Glu Ala Tyr Arg
                405                 410                 415 tcc cgt gga cac ctc atc gct gac acc aac cca ctt tca tgg gtt cag     1296
Ser Arg Gly His Leu Ile Ala Asp Thr Asn Pro Leu Ser Trp Val Gln
            420                 425                 430 cct ggc atg cca gtt cca gac cac cgc gac ctc gac atc gag acc cac     1344
Pro Gly Met Pro Val Pro Asp His Arg Asp Leu Asp Ile Glu Thr His
        435                 440                 445 aac ctg acc atc tgg gat ctg gac cgt acc ttc aac gtc ggt ggc ttc     1392
Asn Leu Thr Ile Trp Asp Leu Asp Arg Thr Phe Asn Val Gly Gly Phe
450                 455                 460 ggc ggc aag gag acc atg acc ctg cgc gag gta ctg tcc cgc ctc cgc     1440
Gly Gly Lys Glu Thr Met Thr Leu Arg Glu Val Leu Ser Arg Leu Arg
465                 470                 475                 480 gct gcg tac acc ctc aag gtc ggc tcc gaa tac acc cac atc ctg gac     1488
Ala Ala Tyr Thr Leu Lys Val Gly Ser Glu Tyr Thr His Ile Leu Asp
                485                 490                 495 cgc gac gag cgc acc tgg ctg cag gac cgc ctc gag gcc gga atg cca     1536
Arg Asp Glu Arg Thr Trp Leu Gln Asp Arg Leu Glu Ala Gly Met Pro
            500                 505                 510 aag cca acc cag gca gag cag aag tac atc ctg cag aag ctg aac gcc     1584
Lys Pro Thr Gln Ala Glu Gln Lys Tyr Ile Leu Gln Lys Leu Asn Ala
        515                 520                 525 gcg gag gct ttc gag aac ttc ctg cag acc aag tac gtc ggc cag aag     1632
Ala Glu Ala Phe Glu Asn Phe Leu Gln Thr Lys Tyr Val Gly Gln Lys
530                 535                 540
```

```
cgc ttc tcc ctc gaa ggt gca gaa gca ctt atc cca ctg atg gac tcc      1680
Arg Phe Ser Leu Glu Gly Ala Glu Ala Leu Ile Pro Leu Met Asp Ser
545                 550                 555                 560 gcc atc gac acc gcc gca ggc caa ggc ctc gac gaa gtt gtc atc ggt      1728
Ala Ile Asp Thr Ala Ala Gly Gln Gly Leu Asp Glu Val Val Ile Gly
                565                 570                 575 atg cca cac cgt ggt cgc ctc aac gtg ctg ttc aac atc gtg ggc aag      1776
Met Pro His Arg Gly Arg Leu Asn Val Leu Phe Asn Ile Val Gly Lys
580                 585                 590 cca ctg gca tcc atc ttc aac gag ttt gaa ggc caa atg gag cag ggc      1824
Pro Leu Ala Ser Ile Phe Asn Glu Phe Glu Gly Gln Met Glu Gln Gly
                595                 600                 605 cag atc ggt ggc tcc ggt gac gtg aag tac cac ctc ggt tcc gaa ggc      1872
Gln Ile Gly Gly Ser Gly Asp Val Lys Tyr His Leu Gly Ser Glu Gly
610                 615                 620 cag cac ctg cag atg ttc ggc gac ggc gag atc aag gtc tcc ctg act      1920
Gln His Leu Gln Met Phe Gly Asp Gly Glu Ile Lys Val Ser Leu Thr
625                 630                 635                 640 gct aac ccg tcc cac ctg gaa gct gtt aac cca gtg atg gaa ggt atc      1968
Ala Asn Pro Ser His Leu Glu Ala Val Asn Pro Val Met Glu Gly Ile
                645                 650                 655 gtc cgc gca aag cag gac tac ctg gac aag ggc gta gac ggc aag act      2016
Val Arg Ala Lys Gln Asp Tyr Leu Asp Lys Gly Val Asp Gly Lys Thr
                660                 665                 670 gtt gtg cca ctg ctg ctc cac ggt gac gct gca ttc gca ggc ctg ggc      2064
Val Val Pro Leu Leu Leu His Gly Asp Ala Ala Phe Ala Gly Leu Gly
                675                 680                 685 atc gtg cca gaa acc atc aac ctg gct aag ctg cgt ggc tac gac gtc      2112
Ile Val Pro Glu Thr Ile Asn Leu Ala Lys Leu Arg Gly Tyr Asp Val
690                 695                 700 ggc ggc acc atc cac atc gtg gtg aac aac cag atc ggc ttc acc acc      2160
Gly Gly Thr Ile His Ile Val Val Asn Asn Gln Ile Gly Phe Thr Thr
705                 710                 715                 720 acc cca gac tcc agc cgc tcc atg cac tac gca acc gac tac gcc aag      2208
Thr Pro Asp Ser Ser Arg Ser Met His Tyr Ala Thr Asp Tyr Ala Lys
                725                 730                 735 gca ttc ggc tgc cca gtc ttc cac gtc aac ggc gac gac cca gag gca      2256
Ala Phe Gly Cys Pro Val Phe His Val Asn Gly Asp Asp Pro Glu Ala
                740                 745                 750 gtt gtc tgg gtt ggc cag ctg gcc acc gag tac cgt cgt cgc ttc ggc      2304
Val Val Trp Val Gly Gln Leu Ala Thr Glu Tyr Arg Arg Arg Phe Gly
                755                 760                 765 aag gac gtc ttc atc gac ctc gtc tgc tac cgc ctc cgc ggc cac aac      2352
Lys Asp Val Phe Ile Asp Leu Val Cys Tyr Arg Leu Arg Gly His Asn
770                 775                 780 gaa gct gat gat cct tcc atg acc cag cca aag atg tat gag ctc atc      2400
Glu Ala Asp Asp Pro Ser Met Thr Gln Pro Lys Met Tyr Glu Leu Ile
785                 790                 795                 800 acc ggc cgc gag acc gtt cgt gct cag tac acc gaa gac ctg ctc gga      2448
Thr Gly Arg Glu Thr Val Arg Ala Gln Tyr Thr Glu Asp Leu Leu Gly
                805                 810                 815 cgt gga gac ctc tcc aac gaa gat gca gaa gca gtc gtc cgc gac ttc      2496
Arg Gly Asp Leu Ser Asn Glu Asp Ala Glu Ala Val Val Arg Asp Phe
                820                 825                 830 cac gac cag atg gaa tct gtg ttc aac gaa gtc aag gaa ggc ggc aag      2544
His Asp Gln Met Glu Ser Val Phe Asn Glu Val Lys Glu Gly Gly Lys
                835                 840                 845 aag cag gct gag gca cag acc ggc atc acc ggc tcc cag aag ctt cca      2592
Lys Gln Ala Glu Ala Gln Thr Gly Ile Thr Gly Ser Gln Lys Leu Pro
850                 855                 860
```

-continued

| | |
|---|---|
| cac ggc ctt gag acc aac atc tcc cgt gaa gag ctc ctg gaa ctg gga<br>His Gly Leu Glu Thr Asn Ile Ser Arg Glu Glu Leu Leu Glu Leu Gly<br>865                870                875              880 | 2640 |
| cag gct ttc gcc aac acc cca gaa ggc ttc aac tac cac cca cgt gtg<br>Gln Ala Phe Ala Asn Thr Pro Glu Gly Phe Asn Tyr His Pro Arg Val<br>                885                890              895 | 2688 |
| gct ccc gtt gct aag aag cgc gtc tcc tct gtc acc gaa ggt ggc atc<br>Ala Pro Val Ala Lys Lys Arg Val Ser Ser Val Thr Glu Gly Gly Ile<br>900                905                910 | 2736 |
| gac tgg gca tgg ggc gag ctc ctc gcc ttc ggt tcc ctg gct aac tcc<br>Asp Trp Ala Trp Gly Glu Leu Leu Ala Phe Gly Ser Leu Ala Asn Ser<br>     915             920                925 | 2784 |
| ggc cgc ttg gtt cgc ctt gca ggt gaa gat tcc cgc cgc ggt acc ttc<br>Gly Arg Leu Val Arg Leu Ala Gly Glu Asp Ser Arg Arg Gly Thr Phe<br>930                935                940 | 2832 |
| acc cag cgc cac gca gtt gcc atc gac cca gcg acc gct gaa gag ttc<br>Thr Gln Arg His Ala Val Ala Ile Asp Pro Ala Thr Ala Glu Glu Phe<br>945                950                955              960 | 2880 |
| aac cca ctc cac gag ctt gca cag tcc aag ggc aac aac ggt aag ttc<br>Asn Pro Leu His Glu Leu Ala Gln Ser Lys Gly Asn Asn Gly Lys Phe<br>                965                970              975 | 2928 |
| ctg gtc tac aac tcc gca ctg acc gag tac gca ggc atg ggc ttc gag<br>Leu Val Tyr Asn Ser Ala Leu Thr Glu Tyr Ala Gly Met Gly Phe Glu<br>980                985                990 | 2976 |
| tac ggc tac tcc gta gga aac gaa gac tcc atc gtt gca tgg gaa gca<br>Tyr Gly Tyr Ser Val Gly Asn Glu Asp Ser Ile Val Ala Trp Glu Ala<br>     995             1000             1005 | 3024 |
| cag ttc ggc gac ttc gcc aac ggc gct cag acc atc atc gat gag<br>Gln Phe Gly Asp Phe Ala Asn Gly Ala Gln Thr Ile Ile Asp Glu<br>1010               1015             1020 | 3069 |
| tac gtc tcc tca ggc gaa gct aag tgg ggc cag acc tcc aag ctg<br>Tyr Val Ser Ser Gly Glu Ala Lys Trp Gly Gln Thr Ser Lys Leu<br>1025               1030             1035 | 3114 |
| atc ctt ctg ctg cct cac ggc tac gaa ggc cag ggc cca gac cac<br>Ile Leu Leu Leu Pro His Gly Tyr Glu Gly Gln Gly Pro Asp His<br>1040               1045             1050 | 3159 |
| tct tcc gca cgt atc gag cgc ttc ctg cag ctg tgc gct gag ggt<br>Ser Ser Ala Arg Ile Glu Arg Phe Leu Gln Leu Cys Ala Glu Gly<br>1055               1060             1065 | 3204 |
| tcc atg act gtt gct cag cca tcc acc cca gca aac cac ttc cac<br>Ser Met Thr Val Ala Gln Pro Ser Thr Pro Ala Asn His Phe His<br>1070               1075             1080 | 3249 |
| cta ctg cgt cgt cac gct ctg tcc gac ctg aag cgt cca ctg gtt<br>Leu Leu Arg Arg His Ala Leu Ser Asp Leu Lys Arg Pro Leu Val<br>1085               1090             1095 | 3294 |
| atc ttc acc ccg aag tcc atg ctg cgt aac aag gct gct gcc tcc<br>Ile Phe Thr Pro Lys Ser Met Leu Arg Asn Lys Ala Ala Ala Ser<br>1100               1105             1110 | 3339 |
| gca cca gaa gac ttc act gag gtc acc aag ttc cag tcc gtg atc<br>Ala Pro Glu Asp Phe Thr Glu Val Thr Lys Phe Gln Ser Val Ile<br>1115               1120             1125 | 3384 |
| aac gat cca aac gtt gca gat gca gcc aag gtg aag aag gtc atg<br>Asn Asp Pro Asn Val Ala Asp Ala Ala Lys Val Lys Lys Val Met<br>1130               1135             1140 | 3429 |
| ctg gtc tcc ggc aag ctg tac tac gaa ttg gca aag cgc aag gag<br>Leu Val Ser Gly Lys Leu Tyr Tyr Glu Leu Ala Lys Arg Lys Glu<br>1145               1150             1155 | 3474 |
| aag gac gga cgc gac gac atc gcg atc gtt cgt atc gaa atg ctc<br>Lys Asp Gly Arg Asp Asp Ile Ala Ile Val Arg Ile Glu Met Leu | 3519 |

```
                 1160              1165             1170
cac cca att ccg ttc aac cgc atc tcc gag gct ctt gcc ggc tac    3564
His Pro Ile Pro Phe Asn Arg Ile Ser Glu Ala Leu Ala Gly Tyr
    1175            1180             1185 cct aac gct gag gaa gtc ctc ttc gtt cag gat gag cca gca aac    3609
Pro Asn Ala Glu Glu Val Leu Phe Val Gln Asp Glu Pro Ala Asn
    1190            1195             1200 cag ggc cca tgg ccg ttc tac cag gag cac ctc cca gag ctg atc    3654
Gln Gly Pro Trp Pro Phe Tyr Gln Glu His Leu Pro Glu Leu Ile
    1205            1210             1215 ccg aac atg cca aag atg cgc cgc gtt tcc cgc cgc gct cag tcc    3699
Pro Asn Met Pro Lys Met Arg Arg Val Ser Arg Arg Ala Gln Ser
    1220            1225             1230 tcc acc gca act ggt gtt gcc aag gtg cac cag ctg gag gag aag    3744
Ser Thr Ala Thr Gly Val Ala Lys Val His Gln Leu Glu Glu Lys
    1235            1240             1245 cag ctt atc gac gag gct ttc gag gct taa                        3774
Gln Leu Ile Asp Glu Ala Phe Glu Ala
    1250            1255

<210> SEQ ID NO 51
<211> LENGTH: 1257
<212> TYPE: PRT
<213> ORGANISM: Corynebacterium glutamicum

<400> SEQUENCE: 51

Met Leu Gln Leu Gly Leu Arg His Asn Gln Pro Thr Thr Asn Val Thr
1               5                   10                  15

Val Asp Lys Thr Lys Leu Asn Lys Pro Ser Arg Ser Lys Glu Lys Arg
                20                  25                  30

Arg Val Pro Ala Val Ser Ser Ala Ser Thr Phe Gly Gln Asn Ala Trp
            35                  40                  45

Leu Val Asp Glu Met Phe Gln Gln Phe Gln Lys Asp Pro Lys Ser Val
        50                  55                  60

Asp Lys Glu Trp Arg Glu Leu Phe Glu Ala Gln Gly Gly Pro Asn Thr
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Asp Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240
```

```
Pro Gln Lys Asp Gly Ser Arg Ala Leu Val Ala Ala Ile Lys Glu
            245                 250                 255

Thr Glu Lys Met Asn Phe Ser Glu Phe Leu Ala Ala Tyr Glu Asp Ile
                260                 265                 270

Val Ala Arg Ser Arg Lys Gly Lys Leu Thr Met Asp Asp Tyr Gln Gly
            275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
    370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Asn Leu Thr Ile Trp Asp Leu Asp Arg Thr Phe Asn Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
    530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
```

-continued

```
                660                 665                 670
Val Val Pro Leu Leu His Gly Asp Ala Ala Phe Ala Gly Leu Gly
        675                 680                 685
Ile Val Pro Glu Thr Ile Asn Leu Ala Lys Leu Arg Gly Tyr Asp Val
        690                 695                 700
Gly Gly Thr Ile His Ile Val Asn Asn Gln Ile Gly Phe Thr Thr
705                 710                 715                 720
Thr Pro Asp Ser Ser Arg Ser Met His Tyr Ala Thr Asp Tyr Ala Lys
                725                 730                 735
Ala Phe Gly Cys Pro Val Phe His Val Asn Gly Asp Asp Pro Glu Ala
                740                 745                 750
Val Val Trp Val Gly Gln Leu Ala Thr Glu Tyr Arg Arg Phe Gly
        755                 760                 765
Lys Asp Val Phe Ile Asp Leu Val Cys Tyr Arg Leu Arg Gly His Asn
        770                 775                 780
Glu Ala Asp Asp Pro Ser Met Thr Gln Pro Lys Met Tyr Glu Leu Ile
785                 790                 795                 800
Thr Gly Arg Glu Thr Val Arg Ala Gln Tyr Thr Glu Asp Leu Leu Gly
                805                 810                 815
Arg Gly Asp Leu Ser Asn Glu Asp Ala Glu Ala Val Val Arg Asp Phe
                820                 825                 830
His Asp Gln Met Glu Ser Val Phe Asn Glu Val Lys Glu Gly Gly Lys
        835                 840                 845
Lys Gln Ala Glu Ala Gln Thr Gly Ile Thr Gly Ser Gln Lys Leu Pro
        850                 855                 860
His Gly Leu Glu Thr Asn Ile Ser Arg Glu Glu Leu Leu Glu Leu Gly
865                 870                 875                 880
Gln Ala Phe Ala Asn Thr Pro Glu Gly Phe Asn Tyr His Pro Arg Val
                885                 890                 895
Ala Pro Val Ala Lys Lys Arg Val Ser Ser Val Thr Glu Gly Gly Ile
                900                 905                 910
Asp Trp Ala Trp Gly Glu Leu Leu Ala Phe Gly Ser Leu Ala Asn Ser
        915                 920                 925
Gly Arg Leu Val Arg Leu Ala Gly Glu Asp Ser Arg Arg Gly Thr Phe
930                 935                 940
Thr Gln Arg His Ala Val Ala Ile Asp Pro Ala Thr Ala Glu Glu Phe
945                 950                 955                 960
Asn Pro Leu His Glu Leu Ala Gln Ser Lys Gly Asn Asn Gly Lys Phe
                965                 970                 975
Leu Val Tyr Asn Ser Ala Leu Thr Glu Tyr Ala Gly Met Gly Phe Glu
                980                 985                 990
Tyr Gly Tyr Ser Val Gly Asn Glu  Asp Ser Ile Val Ala  Trp Glu Ala
        995                 1000                1005
Gln Phe  Gly Asp Phe Ala Asn  Gly Ala Gln Thr Ile  Ile Asp Glu
        1010                1015                1020
Tyr Val  Ser Ser Gly Glu Ala  Lys Trp Gly Gln Thr  Ser Lys Leu
        1025                1030                1035
Ile Leu  Leu Leu Pro His Gly  Tyr Glu Gly Gln Gly  Pro Asp His
        1040                1045                1050
Ser Ser  Ala Arg Ile Glu Arg  Phe Leu Gln Leu Cys  Ala Glu Gly
        1055                1060                1065
Ser Met  Thr Val Ala Gln Pro  Ser Thr Pro Ala Asn  His Phe His
        1070                1075                1080
```

-continued

```
Leu Leu Arg Arg His Ala Leu Ser Asp Leu Lys Arg Pro Leu Val
    1085            1090                1095

Ile Phe Thr Pro Lys Ser Met Leu Arg Asn Lys Ala Ala Ala Ser
    1100            1105                1110

Ala Pro Glu Asp Phe Thr Glu Val Thr Lys Phe Gln Ser Val Ile
    1115            1120                1125

Asn Asp Pro Asn Val Ala Asp Ala Ala Lys Val Lys Lys Val Met
    1130            1135                1140

Leu Val Ser Gly Lys Leu Tyr Tyr Glu Leu Ala Lys Arg Lys Glu
    1145            1150                1155

Lys Asp Gly Arg Asp Asp Ile Ala Ile Val Arg Ile Glu Met Leu
    1160            1165                1170

His Pro Ile Pro Phe Asn Arg Ile Ser Glu Ala Leu Ala Gly Tyr
    1175            1180                1185

Pro Asn Ala Glu Glu Val Leu Phe Val Gln Asp Glu Pro Ala Asn
    1190            1195                1200

Gln Gly Pro Trp Pro Phe Tyr Gln Glu His Leu Pro Glu Leu Ile
    1205            1210                1215

Pro Asn Met Pro Lys Met Arg Arg Val Ser Arg Arg Ala Gln Ser
    1220            1225                1230

Ser Thr Ala Thr Gly Val Ala Lys Val His Gln Leu Glu Glu Lys
    1235            1240                1245

Gln Leu Ile Asp Glu Ala Phe Glu Ala
    1250            1255
```

L-GLUTAMIC ACID-PRODUCING MICROORGANISM AND A METHOD FOR PRODUCING L-GLUTAMIC ACID

This application claims priority under 35 U.S.C. §119(e) to U.S. provisional application 60/651,229, filed Feb. 10, 2005, the entirety of which is incorporated by reference.

FIELD OF THE INVENTION

The present invention relates to an L-glutamic acid-producing microorganism and a method for producing L-glutamic acid using the microorganism. L-glutamic acid is widely used in food industry, for example, as a raw material for production of seasonings.

BRIEF DESCRIPTION OF THE RELATED ART

L-glutamic acid has been conventionally produced on an industrial scale by fermentative methods using L-glutamic acid-producing coryneform bacteria such as those belonging to the genus *Brevibacterium* and *Corynebacterium*. To improve the L-glutamic acid-producing ability of the coryneform bacteria, strains isolated from nature or artificial mutants of such strains are used as the L-glutamic acid-producing coryneform bacteria.

Various technologies for improving the L-glutamic acid-producing ability by enhancing L-glutamic acid biosynthetic enzyme activity using recombinant DNA techniques have been reported. For example, coryneform bacteria with an amplified citrate synthase gene (JP07-121228B), and coryneform bacteria with an amplified glutamate dehydrogenase gene (EP 955368) have been reported.

In the production of substances by fermentation, it is necessary to maintain sufficient growth of bacterial cells to sufficiently produce a target substance. Accordingly, it is necessary to breed a strain with enhanced biosynthesis of a target substance without causing a decrease in bacterial growth. In the production of L-glutamic acid, it has been reported that it is advantageous to decrease α-ketoglutarate dehydrogenase activity (JP06-237779A, and WO95/34672). However, there have been no reports of decreasing the α-ketoglutarate dehydrogenase activity while maintaining a sufficient level of L-glutamic acid production.

SUMMARY OF THE INVENTION

An object of the present invention is to provide a technology to improve the L-glutamic acid-producing ability of coryneform bacteria for fermentative production of L-glutamic acid. When the α-ketoglutarate dehydrogenase gene is disrupted, energy generated through the TCA cycle is decreased, leading to retardation of the bacterial growth. As a result, sufficient yield of L-glutamic acid may not be obtained.

Therefore, a mutant strain having a decreased ability to degrade L-glutamic acid while maintaining an ordinary growth rate would be useful for efficient production of L-glutamic acid. Mutant strains were obtained that have a decreased α-ketoglutarate dehydrogenase activity and maintain almost the same growth rate as a wild-type strain, by introducing mutations into a chromosomal odhA gene that encodes the E1o subunits of the α-ketoglutarate dehydrogenase complex of coryneform bacterium. L-glutamic acid was found to be efficiently produced by using such mutant strains.

It is an object of the present invention to provide an L-glutamic acid-producing coryneform bacterium, comprising
  a) intracellular α-ketoglutarate dehydrogenase activity which is less than half that of a non-mutated or wild-type strain, and
  b) a mutation in a coding region or an expression control region of a chromosomal odhA gene encoding the E1o subunit of the α-ketoglutarate dehydrogenase complex, wherein said bacterium grows at a rate which is at least about 80% of the growth rate of a non-mutated or wild-type strain.

It is a further object of the present invention to provide the coryneform bacterium as described above, wherein said odhA gene encodes a protein selected from the group consisting of:
  (A) a protein comprising an amino acid sequence of SEQ ID NO: 10,
  (B) a protein comprising an amino acid sequence of SEQ ID NO: 10, whereby one or several amino acids in said protein are substituted, deleted, inserted, or added, and wherein said protein has an activity of the E1o subunit of the α-ketoglutarate dehydrogenase complex.
  (C) a protein comprising amino acids 37 to 1257 of SEQ ID NO: 10, and
  (D) a protein comprising amino acids 37 to 1257 of SEQ ID NO: 10, whereby one or several amino acids in said protein are substituted, deleted, inserted, or added, and wherein said protein has an activity of the E1o subunit of the α-ketoglutarate dehydrogenase complex.

It is a further object of the present invention to provide the coryneform bacterium as described above, wherein said several amino acids are 2 to 20 amino acids.

It is a further object of the present invention to provide the coryneform bacterium as described above, wherein said odhA gene is selected from the group consisting of:
  (a) a gene comprising nucleotides 443 to 4213 of SEQ ID NO: 9,
  (b) a gene that is able to hybridize under stringent conditions to a polynucleotide comprising nucleotides 443 to 4213 of ID NO: 9 or a probe prepared from a polynucleotide comprising nucleotides 443 to 4213 of SEQ ID NO: 9, and wherein said gene encodes a protein which has the activity of the E1o subunit of the α-ketoglutarate dehydrogenase complex,
  (c) a gene comprising nucleotides 551 to 4213 of SEQ ID NO: 9, and
  (d) a gene that is able to hybridize under stringent conditions to a polynucleotide comprising nucleotides 551 to 4213 of SEQ ID NO: 9 or a probe prepared from a polynucleotide comprising nucleotides 551 to 4213 of SEQ ID NO: 9, and wherein said gene encodes a protein which has the activity of the E1o subunit of the α-ketoglutarate dehydrogenase complex.

It is a further object of the present invention to provide the coryneform bacterium as described above, wherein said mutation is introduced into a region encoding a thiamine pyrophosphate binding region.

It is a further object of the present invention to provide the coryneform bacterium as described above, wherein said mutation comprises deletion of an amino acid selected from the group consisting of Gly at position 686, Leu at position 687, Gly at position 688, Asn at position 713, Asn at position 714, and combinations thereof in the amino acid sequence shown in SEQ ID NO: 10.

It is a further object of the present invention to provide the coryneform bacterium as described above, wherein said mutation is introduced into the region comprising nucleotides 2534 to 2548 of SEQ ID NO: 9.

It is a further object of the present invention to provide the coryneform bacterium as described above, wherein said mutation comprises deletion of one or more amino acids in the region comprising amino acids 698 to 702 of SEQ ID NO: 10.

It is a further object of the present invention to provide the coryneform bacterium as described above, wherein said mutation comprises replacement of an amino acid selected from the group consisting of Lys at position 698, Leu at position 699, Arg at position 700, Tyr at position 702, and combinations thereof in the amino acid sequence shown in SEQ ID NO: 10.

It is a further object of the present invention to provide the coryneform bacterium as described above, wherein said mutation is introduced into the region comprising nucleotides 1094 to 1114 of SEQ ID NO: 9.

It is a further object of the present invention to provide the coryneform bacterium as described above, wherein said mutation comprises deletion of one or more amino acids in the region comprising amino acids 218 to 224 of SEQ ID NO: 10.

It is a further object of the present invention to provide a method for producing L-glutamic acid comprising:

a) culturing the coryneform bacterium according to claim 1 in a culture medium and b) collecting L-glutamic acid from the culture medium and/or the bacterium.

It is a further object of the present invention to provide a gene encoding mutant α-ketoglutarate dehydrogenase selected from the group consisting:

(a) a gene comprising nucleotides 443 to 4213 of a polynucleotide selected from the group consisting of SEQ ID NO: 11, 13, and 15, or a gene comprising nucleotides 443 to 4210 of a polynucleotide selected from the group consisting of SEQ ID NO: 44, 46, and 48, (b) a gene that is able to hybridize under stringent conditions to a polynucleotide comprising nucleotides 443 to 4213 of a polynucleotide selected from the group consisting of SEQ ID NO: 11, 13, and 15, a polynucleotide comprising nucleotides 443 to 4210 of a polynucleotide selected from the group consisting of SEQ ID NO:44, 46, and 48, a probe prepared from nucleotides 443 to 4213 of a polynucleotide selected from the group consisting of SEQ ID NO: 11, 13, and 15, or a probe prepared from nucleotides 443 to 4210 of a polynucleotide selected from the group consisting of SEQ ID NO: 44, 46, and 48, and wherein said gene encodes a protein which has α-ketoglutarate dehydrogenase activity which is less than half that of a wild-type or non-mutated strain by forming a complex with E2o and E3 subunits, (c) a gene comprising nucleotides 551 to 4213 of a polynucleotide selected from the group consisting of SEQ ID NO: 11, 13, and 15, or a gene comprising nucleotides 551 to 4210 of a polynucleotide selected from the group consisting of SEQ ID NO: 44, 46, and 48, and (d) a gene that is able to hybridize under stringent conditions to a polynucleotide comprising nucleotides 551 to 4213 of a polynucleotide selected from the group consisting of SEQ ID NO: 11, 13, and 15, a polynucleotide comprising nucleotides 551 to 4210 of a polynucleotide selected from the group consisting of SEQ ID NO: 44, 46, and 48, or a probe prepared from nucleotides 551 to 4213 of a polynucleotide selected from the group consisting of SEQ ID NO: 11, 13, and 15, or a probe prepared from nucleotides 551 to 4210 of a polynucleotide selected from the group consisting of SEQ ID NO: 44, 46, and 48, and wherein said gene encodes a protein which has α-ketoglutarate dehydrogenase activity which is less than half that of a wild-type or non-mutated strain by forming a complex with E2o and E3 subunits.

It is a further object of the present invention to provide a mutant α-ketoglutarate dehydrogenase selected from the group consisting of:

(a) a protein selected from the group consisting of SEQ ID NO: 12, 14, 16, 45, 47, and 49, (b) a protein selected from the group consisting of SEQ ID NO: 12, 14, 16, 45, 47, and 49, whereby one or several amino acids in said protein are substituted, deleted, or added, and wherein said protein exhibits α-ketoglutarate dehydrogenase activity which is less than half that of a wild-type or non-mutated strain by forming a complex with E2o and E3 subunits, (c) a protein comprising amino acids 37 to 1257 of an amino acid sequence selected from the group consisting of SEQ ID NO: 12, 45, 47, and 49, a protein comprising amino acids 37 to 1255 of an amino acid sequence of SEQ ID NO: 14, or a protein comprising amino acids 37 to 1254 of an amino acid sequence of SEQ ID NO: 16, and (d) a protein comprising amino acids 37 to 1257 of an amino acid sequence selected from the group consisting of SEQ ID NO: 12, 45, 47, and 49, a protein comprising amino acids 37 to 1255 of an amino acid sequence of SEQ ID NO: 14, or a protein comprising amino acids 37 to 1254 of an amino acid sequence of SEQ ID NO: 16, whereby one or several amino acids in said protein are substituted, deleted, or added, and wherein said protein exhibits α-ketoglutarate dehydrogenase activity which is less than half that of a wild-type or non-mutated strain by forming a complex with E2o and E3 subunits.

DESCRIPTION OF THE PREFERRED EMBODIMENTS

Figure 1:
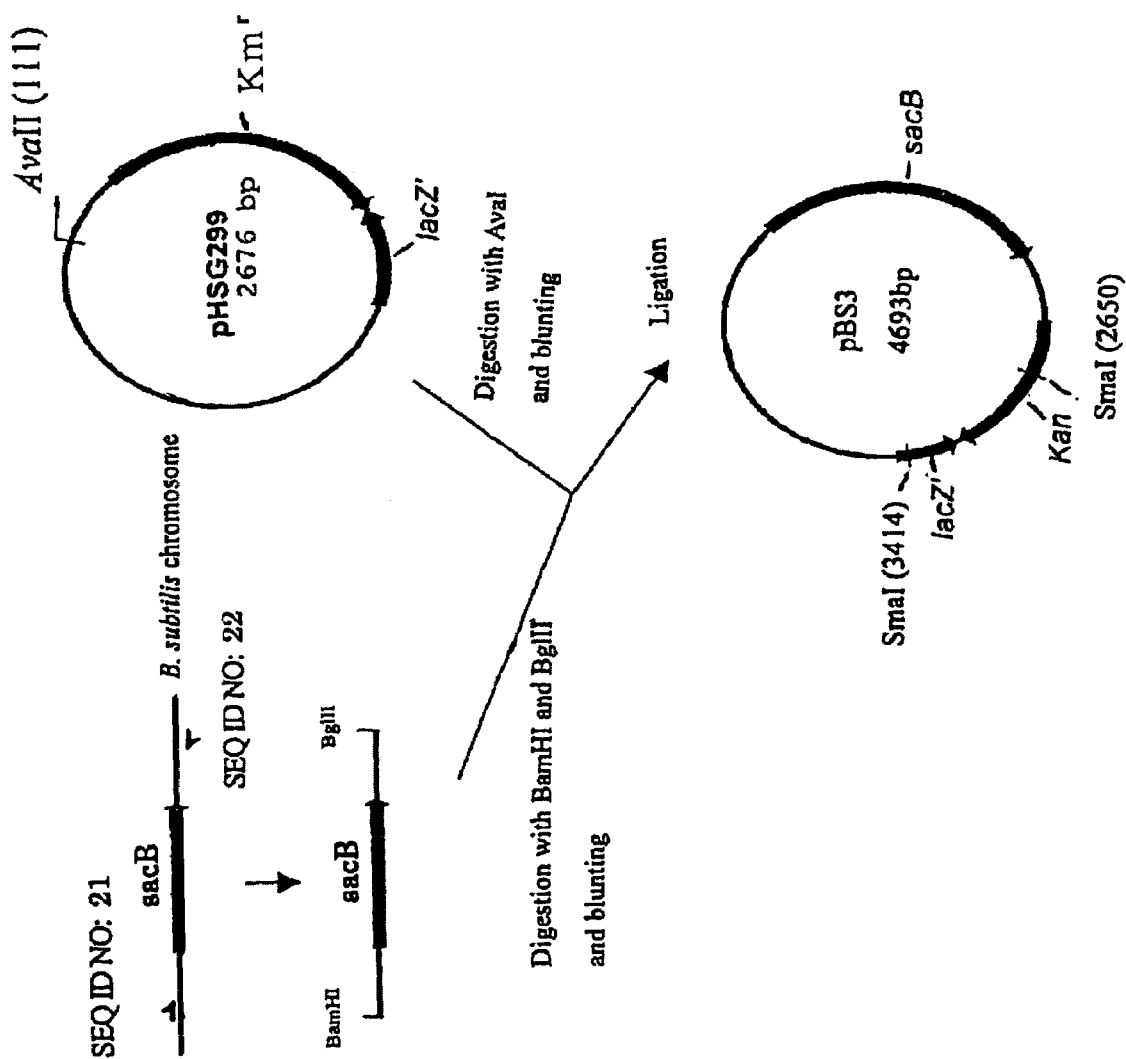
FIG. 1 shows the construction of plasmid pBS3.

Hereinafter, the present invention will be described in detail.

<1> Coryneform Bacterium of the Present Invention

The coryneform bacterium of the present invention has an L-glutamic acid-producing ability, and grows almost at the same growth rate as a non-mutated strain or a wild-type strain. The *corynebacterium* of the present invention has intracellular α-ketoglutarate dehydrogenase (hereinafter, also referred to as "α-KGDH") activity which is less than half that of a non-mutated strain or the wild-type strain, by introduction of mutations into a coding region or an expression control region of the odhA gene, which encodes the E1o subunit of α-KGDH complex.

α-KGDH is also called oxoglutarate dehydrogenase or 2-oxoglutarate dehydrogenase.

In the present invention, examples of coryneform bacterium include conventional coryneform bacterium, and also include bacteria that had been classified into the genus *Brevibacterium* but are currently is classified into the genus *Corynebacterium* (Int. J. Syst. Bacteriol., 41, 255(1991)), as well as the *Brevibacterium* bacteria that are very close to *Corynebacterium* bacteria. Examples of such coryneform bacterium include the following.

Corynebacterium acetoacidophilum
Corynebacterium acetoglutamicum
Corynebacterium alkanolyticum
Corynebacterium callunae
Corynebacterium glutamicum
Corynebacterium lilium
Corynebacterium melassecola
Corynebacterium thermoaminogenes (Corynebacterium efficiens)
Corynebacterium herculis
Brevibacterium divaricatum
Brevibacterium flavum
Brevibacterium immariophilum
Brevibacterium lactofermentum (Corynebacterium glutamicum)
Brevibacterium roseum
Brevibacterium saccharolyticum
Brevibacterium thiogenitalis
Brevibacterium ammoniagenes
Brevibacterium album
Brevibacterium cerinum
Microbacterium ammoniaphilum Specific examples of the coryneform bacteria are as follows.

Corynebacterium acetoacidophilum ATCC 13870
Corynebacterium acetoglutamicum ATCC 15806
Corynebacterium alkanolyticum ATCC21511
Corynebacterium callunae ATCC15991
Corynebacterium glutamicum ATCC 13020, ATCC 13032, ATCC 13060, ATCC 13869
Corynebacterium lilium ATCC 15990
Corynebacterium melassecola ATCC 17965
Corynebacterium thermoaminogenes AJ12340 (FERM BP-1539)
Corynebacterium herculis ATCC13868
Brevibacterium divaricatum ATCC 14020
Brevibacterium flavum ATCC 13826, ATCC 14067, AJ 12418 (FERM BP-2205)
Brevibacterium immariophilum ATCC14068
Brevibacterium lactofermentum (Corynebacterium glutamicum) ATCC 13869
Brevibacterium roseum ATCC13825
Brevibacterium saccharolyticum ATCC 14066
Brevibacterium thiogenitalis ATCC19240
Brevibacterium ammoniagenes ATCC6871, ATCC6872
Brevibacterium album ATCC 15111
Brevibacterium cerinum ATCC 15112
Microbacterium ammoniaphilum ATCC 15354

These strains are available from the American Type Culture Collection (ATCC, Address: P.O. Box 1549, Manassas, Va. 20108, United States of America). That is, each strain is given a unique registration number which is listed in the catalogue of the ATCC. Strains can be ordered using this registration number. The AJ12340 strain was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305–5466, Japan) on Oct. 27, 1989 under the provisions of the Budapest Treaty and given an accession number of FERM BP-1539. The AJ12418 strain was deposited at National Institute of Bioscience and Human Technology, Agency of Industrial Science and Technology, Ministry of International Trade and Industry on Jan. 5, 1989 under the provisions of the Budapest Treaty and given an accession number of FERM BP-2205.

In the present invention, "L-glutamic acid-producing ability" means an ability to cause accumulation of a sufficient amount of L-glutamic acid in a medium when the coryneform bacterium of the present invention is cultured in the medium. The L-glutamic acid-producing ability may be either a property of a parent strain from which the coryneform bacterium of the present invention is bred or a property imparted or enhanced by a mutation, gene recombination, etc. Furthermore, the L-glutamic acid-producing ability may be imparted by introducing a mutation into the odhA gene which encodes the E1o subunit of α-ketoglutarate dehydrogenase complex.

Examples of the methods for imparting the L-glutamic acid-producing ability include enhancing expression of a gene encoding an L-glutamic acid biosynthetic enzyme. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Enhancement of expression of these genes may be achieved by incorporating a DNA fragment containing such a gene into an appropriate plasmid which is able to autonomously replicate in coryneform bacterium, and transforming bacterial cells with the resultant plasmid; integrating such a gene into a chromosome by homologous recombination, conjugation, transposition, etc.; or introducing a mutation into a promoter region of such a gene (WO/0018935).

When the above-mentioned genes are introduced by a plasmid or integrated on a chromosome, a promoter for expression of the genes may be any promoter so long as it is able to function in coryneform bacteria. Examples of such promoters include lac promoter, trp promoter, trc promoter, PS2 promoter, and pL promoter. A native promoter of the gene may also be used.

Examples of microorganisms modified so that expression of citrate synthetase gene, phosphoenolpyruvate carboxylase gene, and/or glutamate dehydrogenase gene is enhanced include those microorganisms disclosed in JP2001-333769A (EP1078989A), JP2000-106869A (EP955368A), JP2000-189169A (EP952221A), and JP2001-333769A (EP1078989A).

The modification for imparting the L-glutamic acid-producing ability includes decreasing or eliminating an activity of an enzyme that catalyzes a reaction for synthesizing a compound other than L-glutamic acid, and branching from an L-glutamic acid biosynthesis pathway. Examples of such enzymes include isocitrate lyase, acetyl phosphate transferase, acetate kinase, acetohydroxy acid synthase, acetolactate synthase, acetyl formate transferase, lactate dehydrogenase, glutamate decarboxylase, and I-pyrophosphate dehydrogenase.

To decrease or eliminate the activity of the enzymes as described above, a mutation or deletion which causes a decrease or loss of the activity of the enzymes may be introduced into the genes of the enzymes on the chromosome. This may be achieved by, for example, disrupting the gene encoding the enzyme on the chromosome, or by modifying an expression control sequence such as a promoter and/or Shine Dargarno (SD) sequence of the gene. In addition, the activities of such enzymes may be decreased or eliminated by introducing a missense mutation which causes an amino acid substitution, a nonsense mutation which generates a stop codon, or a frame shift mutation which adds or deletes one or two nucleotides into a coding region, or by deleting a portion of the gene (Journal of biological Chemistry 272:8611–8617 (1997)). Furthermore, the activities of such enzymes may be decreased or eliminated by constructing a gene encoding a mutant enzyme in which its coding region is deleted and replacing a chromosomal gene with the resulting gene by homologous recombination.

The L-glutamic acid-producing ability may also be imparted by screening a strain resistant to organic acid analogues or respiratory inhibitors, or by screening a strain sensitive to inhibitors of cell wall synthesis. Examples of such methods include imparting resistance to benzopirone or naphtoquinone (JP56-1889A), imparting resistance to HOQNO (JP56-140895A), imparting resistance to α-ketomalonic acid (JP57-2689A), imparting resistance to guanidine (JP56-35981A), and imparting sensitivity to penicillin (JPO4-88994A).

Specific examples of such bacteria include the following strains.

*Brevibacterium flavum* AJ11355 (FERM P-5007; JP56-1889A)

*Corynebacterium glutamicum* AJ11355 (FERM P-5020; JP56-1889A)

*Brevibacterium flavum* AJ11217 (FERM P-4318; JP57-2689A)

*Corynebacterium glutamicum* AJ11218 (FERM P-4319; JP57-2689A)

*Brevibacterium flavum* AJ11564 (FERM P-5472; JP56-140895A)

*Brevibacterium flavum* AJ11439 (FERM P-5136; JP56-35981A)

*Corynebacterium glutamicum* H7684 (FERM BP-3004; JPO4-88994A)

The coryneform bacterium of the present invention can be obtained from coryneform bacterium having the L-glutamic acid-producing ability as described above by introducing a mutation into a chromosomal odhA gene which encodes the E1o subunit of the α-KGDH complex, and selecting those strains that grow almost at the same growth rate as a non-mutated strain or a wild-type strain, and exhibits α-KGDH activity less than half that of the non-mutated strain or wild-type strain. Alternatively, such a mutation may be introduced into the odhA gene first, followed by imparting an L-amino acid-producing ability.

In the present invention, α-KDGH activity means an activity catalyzing a reaction of oxidative decarboxylation of α-ketoglutarate (2-oxoglutarate) to generate succinyl-CoA. The above-mentioned reaction is catalyzed by the α-KDGH complex, which includes three kinds of subunits, i.e., α-ketoglutarate dehydrogenase (E1o, EC1.2.4.2), dihydrolipoamide-S-succinyltransferase (E2o, EC:2.3.1.61), and dihydrolipoamide dehydrogenase (E3, EC:1.8.1.4). That is, these three subunits catalyze each of the following reactions:

E1o subunit:

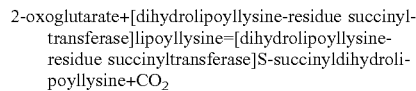

E2o subunit:

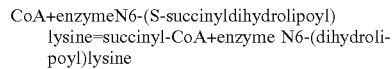

E3 subunit:

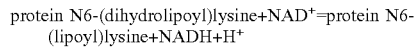

The activity of the "α-KDGH complex" means an activity catalyzing the total reaction of the above three reactions.

In *Escherichia coli*, these three subunits form a complex.

In the case of coryneform bacterium, the E1o subunit is encoded by the odhA gene and the E3 subunit is encoded by the lpd gene (GenBank Accession NO. Y16642; SEQ ID NO: 17). It is controversial whether the E2o subunit is encoded by the odhA gene as a bifunctional protein together with the E1o subunit (Usuda et al., Microbiology 1996 142, 3347–3354), or encoded by a separate gene registered as an accession No. NCg12126 of NC_003450 (SEQ ID NO: 27) in the GenBank database. Thus, the odhA gene may encode the E2o subunit in addition to the E1o subunit.

The coryneform bacteria of the present invention have a mutation in the chromosomal odhA gene. The odhA gene includes, for example, a gene having a nucleotide sequence encoding the amino acid sequence shown in SEQ ID NO: 10. The odhA gene also includes a gene having a nucleotide sequence encoding the amino acid sequence shown in SEQ ID NO: 51. In addition, it is possible that the "gtg" at positions 551 to 553 in the nucleotide sequence of SEQ ID NO: 9 may be translated as Met and translation may be initiated at this codon, even though it is a codon for Val. Therefore, the odhA gene also includes a gene having a nucleotide sequence encoding the amino acid sequence of amino acids 37 to 1257 of SEQ ID NO: 10. Furthermore, the odhA gene may also be a gene encoding a protein that has an amino acid sequence shown in SEQ ID NO: 10 or 51, or amino acid sequence of amino acids 37 to 1257 of SEQ ID NO: 10, including substitution, deletion, insertion or addition of one or several amino acids so long as it exhibits an activity of the E1o subunit of the α-KGDH complex. The activity of the E1o subunit itself can be determined by the method of Massey et al. (Biochim. Biophys. Acta 38,447–460). "Several" as used herein is preferably 2 to 20, more preferably 2 to 10, and particularly preferably 2 to 5.

More specifically, the odhA gene preferably has a nucleotide sequence of nucleotides 443 to 4213 of SEQ ID NO: 9, or a nucleotide sequence of nucleotides 551 to 4213 of SEQ ID NO: 9. The odhA gene may have a nucleotide sequence shown in SEQ ID NO: 50. Furthermore, since the nucleotide sequences of the odhA genes may differ between the species or strains of the coryneform bacteria, the odhA gene may be a gene that hybridizes with a polynucleotide having a nucleotide sequence of nucleotides 443 to 4213 of SEQ ID NO: 9, a polynucleotide having a nucleotide sequence shown in SEQ ID NO: 50, or a nucleotide sequence of nucleotides 551 to 4213 of SEQ ID NO: 9, or a probe prepared from the nucleotide sequences under stringent conditions so long as the gene encodes a protein that exhibits the activity of the E1o subunit of the α-KGDH complex. The "stringent conditions" as used herein are conditions under which a so-called specific hybrid is formed, and a non-specific hybrid is not formed. It is difficult to clearly express this condition by using any numerical value. However, examples of stringent conditions include those under which DNAs hybridize to each other at a salt concentration with washing typical of Southern hybridization, i.e., washing once or preferably 2–3 times under 1×SSC, 0.1% SDS at 60° C., preferably 0.1×SSC, 0.1% SDS at 60° C., more preferably 0.1×SSC, 0.1% SDS at 68° C.

In the present invention, "a mutation is introduced into a chromosomal odhA gene" includes the case where the odhA gene on a chromosome is replaced by a mutant odhA gene to generate substantially the same condition in which a mutation is directly introduced into the chromosomal odhA gene.

The above-mentioned mutation may be introduced not only in the coding region but also in the expression controlling region of the odhA gene. The expression controlling region includes, for example, a promoter, SD sequence, and operator. The expression controlling region of the odhA gene includes a nucleotide sequence of nucleotides 1 to 442 of SEQ ID NO: 9. The expression controlling sequence of the odhA gene may also be identified by genetic analysis software such as GENETYX or by the method disclosed in Goldstein et al. (Prokaryotic promoters in biotechnology. Biotechnol. Annu. Rev., 1995, 1, 105–128).

The "α-KGDH activity less than half that of a non-mutated or wild-type strain" preferably means that the α-KGDH activity per unit cell (per unit weight of protein) of the coryneform bacterium of the present invention cultured for 4 hours is less than half the activity of a non-mutated or wild-type strain of coryneform bacteria cultured under the same conditions. Examples of coryneform bacterium having such decreased α-KGDH activity include a bacterium in which the number of α-KGDH molecules per cell is decreased and a bacterium in which the activity per α-KGDH molecule is decreased. Examples of a wild-type coryneform bacterium used as a control include *Brevibacterium lactofermentum* ATCC13869 strain. The intracellular α-KGDH activity of the coryneform bacterium of the present invention is preferably less than 40%, more preferably less than 30% that of the activity of a non-mutated or wild-type strain. Although α-KGDH activity may be decreased to an undetectable level, it is preferable that the activity is not completely eliminated. The α-KGDH activity (activity of α-KGDH complex) can be measured by the method of Shiio et al. (Isamu Shiio and Kyoko Ujigawa-Takeda, Agric. Biol. Chem., 44(8), 1897–1904, 1980).

As a result of the decrease of intracellular α-KGDH activity, the L-glutamic acid-producing ability of the coryneform bacterium is improved. In the present invention, "L-glutamic acid-producing ability is improved" preferably means that when the strain of coryneform bacterium into which a mutation has been introduced into odhA gene is cultured in a medium, the amount of L-glutamic acid which accumulates in the medium by the mutant coryneform bacterium is larger than that which accumulates by the wild-type or non-mutated strain, or the rate of L-glutamic acid production by the mutant coryneform bacterium is higher than that of the wild-type or non-mutated strain.

The phrase "the bacterium grows almost at the same growth rate compared to a wild-type strain or non-mutated strain" preferably means the bacterium of the present invention grows almost at the same growth rate as a wild-type strain such as *Brevibacterium lactofermentum* ATCC13869. Here, "almost at the same growth rate" means 80% or more, more preferably 90%, or more preferably 95% or more of the growth rate of a wild-type or non-mutated strain. It is not necessary that the coryneform bacterium of the present invention grows almost at the same growth rate as a wild-type or non-mutated strain at any culture temperature. That is, coryneform bacterium which exhibits a sufficient growth rate at low temperatures but exhibits a decreased growth rate at high temperatures such as GN-2-2 strain as shown in the Examples is also included in the coryneform bacterium of the present invention.

The growth rates of the strain of the present invention and the wild-type or non-mutated strain can be compared, for example, by inoculating the same number of cells of each strain in a medium and comparing viable cell numbers after a predetermined time. When a liquid medium is used, the viable cell number can be calculated based on, for example, optical density (OD) at a wavelength of 600 nm or weight of bacterial cells after a predetermined time. When a solid medium such as a plate medium is used, the viable cell numbers can be calculated based on the number of colonies that appeared after a predetermined time.

Examples of the method of introducing a mutation into the odhA gene on the chromosome include using X-rays or ultraviolet rays to irradiate the coryneform bacterium, and treating the coryneform bacterium with a mutagen such as N-methyl-N'-nitro-N-nitrosoguanidine. Mutation may also be introduced into the odhA gene on the chromosome by preparing a mutant odhA gene, and replacing the chromosomal odhA gene with such a mutant odhA gene by a homologous recombination technique. Such a mutant odhA gene may be prepared by error-prone PCR, DNA shuffling, or StEP-PCR (Firth A E, Patrick W M; Bioinformatics. Jun. 2, 2005; Statistics of protein library construction.), or overlap-extension PCR (Urban, A., Neukirchen, S. and Jaeger, K. E., A rapid and efficient method for site-directed mutagenesis using one-step overlap extension PCR. Nucleic Acids Res, 25, 2227–8. (1997)).

Homologous recombination may be performed by a method called "Red-driven integration" in which a linear DNA is used (Datsenko, K. A., PNAS, 97(12), 6640–6645, 2000) or by a method using a plasmid having a temperature-sensitive replication origin (U.S. Pat. No. 6,303,383, and JP05-007491A). Introduction of a mutation into a chromosomal odhA gene may also be performed by using a plasmid which is not replicable in cells of coryneform bacteria or a plasmid capable of transferring to coryneform bacteria by conjugation.

Examples of such a temperature-sensitive plasmid for Coryneform bacteria include p48K and pSFKT2 (JP2000-262288A), pHSC4 (France Patent Laid-open Publication No.2667875, 1992 and JP5-7491A), pBS5T, and so forth. These plasmids can autonomously replicate at least at a temperature of 25° C., but cannot autonomously replicate at a temperature of 37° C. in Coryneform bacteria. The AJ12571 strain harboring pHSC4 was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Aug. 26, 1991 under the provisions of the Budapest Treaty and given an accession number of FERM BP-3524.

A plasmid which is not replicable in the cells of coryneform bacteria is preferably one replicable in cells of *Escherichia* bacteria, and examples thereof include pHSG299 (Takara Bio) and pHSG399 (Takara Bio). Examples of a plasmid capable of transferring to coryneform bacteria by conjugation include pK19mobsacB (J. Bacteriology 174: 5462–65(1992)).

A mutant odhA gene is inserted into a temperature-sensitive plasmid or a plasmid which is not replicable in coryneform bacteria, and the obtained recombinant plasmids are used to transform coryneform bacteria. Transformation can be performed by conventional methods. For example, a method of treating recipient cells with calcium chloride so as to increase the permeability of DNA, which has been reported for *Escherichia coli* (Mandel, M. and Higa, A., J. Mol. Biol., 53, 159 (1970)), and a method of using competent cells prepared from growing cells to introduce a DNA, which has been reported for *Bacillus subtilis* (Duncan, C. H., Wilson, G. A. and Young, F. E., Gene, 1, 153 (1977)) can be employed. In addition to these methods, a method of introducing a recombinant DNA into protoplast- or spheroplast-like recipient cells, which have been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of *Coryneform* bacteria can also be performed by the electric pulse method (Sugimoto et al., JP2-207791A).

In the case of using a plasmid which is not capable in cells of coryneform bacteria, a wild-type odhA gene on a chromosome is replaced with the mutant odhA gene on the plasmid.

In the case of using a temperature-sensitive plasmid, the transformant strain is cultured at a temperature at which the temperature sensitive replication origin does not function (e.g. 25° C.) to obtain a strain into which the plasmid is introduced. Then, the transformant is cultured at a high temperature to eliminate the temperature-sensitive plasmid, and spread over a plate medium containing an antibiotic drug such as kanamycin. Although strains from which the plasmid is eliminated cannot grow on a plate containing such an antibiotic drug, a few strains in which the chromosomal odhA gene is replaced with the mutant odhA gene can grow and appear as colonies.

In such a strain in which the recombinant DNA containing the mutant odhA gene is integrated into the chromosomal DNA as described above, the recombinant DNA causes recombination with the odhA gene that originally exists on the chromosome, and the fusion genes of the chromosomal odhA gene and the mutant odhA gene are inserted into the chromosome so that the other portions of the recombinant DNA (vector segment, temperature sensitive replication origin and drug resistance marker) are present between the fusion genes. Then, in order to leave only the mutant odhA gene on the chromosomal DNA, one copy of the odhA gene is eliminated together with the vector segment (including the temperature sensitive replication origin and the drug resistance marker) from the chromosomal DNA. In this case, the normal odhA gene is left on the chromosomal DNA and the mutant odhA gene is excised from the chromosomal DNA, or to the contrary, the mutant odhA gene is left on the chromosomal DNA and the normal odhA gene is excised from the chromosome DNA. Then, a strain in which only the mutant odhA gene is left on the chromosome can be selected using PCR, Southern hybridization, or the like.

Homologous recombination may be performed using a sacB gene encoding levan sucrase as a marker for recombination. The sacB gene encoding levan sucrase is used to efficiently select strains in which a chromosomal odhA gene is replaced by the mutant odhA gene and a vector portion is cured from a chromosome (Schafer, A. et al., Gene 145 (1994) 69–73). That is, in the case of the coryneform bacteria, when levan sucrase is expressed, levan generated by assimilation of sucrose becomes lethal for the bacteria and hence the bacteria cannot grow. Therefore, by culturing on a sucrose-containing plate, strains in which substitution occurs between the mutant odhA gene in the vector and a chromosomal odhA gene and from which the other portions of the vector are cured can be selected.

Examples of the sacB gene include the followings.
*Bacillus subillus*: sacB GenBank Accession Number X02730 (SEQ ID NO: 19 )
*Bacillus amyloliqufaciens*: sacB GenBank Accession Number X52988
*Zymomonas mobilis*: sacB GenBank Accession Number L33402
*Bacillus stearothermophilus*: surB GenBank Accession Number U34874
*Lactobacillus sanfranciscensis*: frfA GenBank Accession Number AJ508391
*Acetobacter xylinus*: lsxA GenBank Accession Number AB034152
*Gluconacetobacter diazotrophicus*: lsdA GenBank Accession Number L41732

<2> The Mutant odhA Gene of the Present Invention

The mutation to be introduced into the chromosomal odhA gene is not particularly limited so long as it is a mutation which decreases the α-KGDH activity to be less than half of the α-KGDH activity of a non-mutated strain or wild-type strain, but does not cause retardation of the growth of the bacterium. Specific examples of the mutation include the followings.

(1) Mutation in the Thiamine Pyrophosphate Binding Region

This mutation is introduced into the binding region of thiamine pyrophosphate, which is a coenzyme. Thiamine pyrophosphate binding region means a region corresponding to that encoded by nucleotides 2498 to 2584 of the odhA gene (SEQ ID NO: 9). The amino acid sequence of the region is shown as amino acids 686 to 714 in SEQ ID NO: 10. Examples of a mutation in this region include one that causes a deletion of one or more amino acid residues selected from Gly at position 686, Leu at position 687, Gly at position 688, Asn at position 713, and Asn at position 714.

The mutation in the thiamine pyrophosphate binding region may also be introduced in the region of nucleotides 2534 to 2548 of the odhA gene (SEQ ID NO: 9). This mutation is named a GN type mutation. The GN type mutation is preferably a mutation that causes deletion and/or substitution of one or more amino acid residues selected from Lys at position 698, Leu at position 699, Arg at position 700, Gly at position 701, and Tyr at position 702 in SEQ ID NO: 10. An example of such a mutation is that which deletes Gly at position 701 in SEQ ID NO: 10. Examples of the mutant odhA gene having this mutation include a gene having a nucleotide sequence of nucleotides 443 to 4213 of SEQ ID NO: 13, and genes having a nucleotide sequence of nucleotides 443 to 4210 of SEQ ID NOS: 44, 46 or 48, and the mutant α-KGDH proteins encoded by these genes are shown in SEQ ID NOS: 14, 45, 47, and 49. Examples of the mutant odhA gene having this mutation also include a gene having a nucleotide sequence of nucleotides 551 to 4213 of SEQ ID NO: 13, and genes having a nucleotide sequence of nucleotides 551 to 4210 of SEQ ID NOS: 44, 46, or 48, and the mutant α-KGDH proteins encoded by these genes are shown in amino acids 37 to 1255 of SEQ ID NO: 14, and amino acids 37 to 1256 of SEQ ID NOS: 45, 47, and 49. In the nucleotide sequence of SEQ ID NO: 13, a mutation which deletes "t" at position 2538 and "ggcta" at positions 2543 to 2547 of SEQ ID NO: 9 is introduced.

Furthermore, mutant odhA genes having a mutation which results in replacement of one or more amino acid residues selected from Lys at position 698, Leu at position 699, Arg at position 700, and Tyr at position 702 with another amino acid in SEQ ID NO: 10 are also preferable. The "another amino acid" is not particularly limited so long as it is different from the original amino acid, and selected from natural amino acids such as Lys, Glu, Thr, Val, Leu, Ile, Ser, Asp, Asn, Gln, Arg, Cys, Met, Phe, Trp, Tyr, Gly, Ala, Pro, and His. However, it is preferable that Lys at position 698 is replaced by amino acids other than basic amino acids such as Arg and His, Leu at position 699 is replaced by amino acids other than hydrophobic aliphatic amino acids such as Ile and Val, Arg at position 700 is replaced by amino acids other than basic amino acids such as Lys and His, Tyr at position 702 is replaced by amino acids other than hydroxy amino acids such as Ser and Thr. It is particularly preferable that Lys at position 698 is replaced by hydrophobic aliphatic amino acid such as Ile, Leu, or Val, Leu at position 699 is replaced by hydroxyl amino acid such as Ser, Thr or Tyr, Arg at position 700 is replaced by sulfur-containing amino acid such as Cys or Met, Tyr at position 702 is replaced by hydrophobic aliphatic amino acid such as Ile, Leu, or Val.

A GN-type mutation may cause both the deletion of Gly at position 701 and replacement of one or more amino acid residues selected from Lys at position 698, Leu at position 699, Arg at position 700, and Tyr at position 702 in SEQ ID NO: 10. Examples of such mutant odhA gene include genes having a nucleotide sequence of nucleotides 443 to 4210 of SEQ ID NOS: 44, 46, and 48. Amino acid sequences of mutant α-KGDH proteins encoded by these mutant odhA genes are shown in SEQ ID NOS: 45, 47, and 49. Examples of such a mutant odhA gene also include genes having nucleotide sequence of nucleotides 551 to 4210 of SEQ ID NOS: 44, 46, and 48. Amino acid sequences of mutant α-KGDH proteins encoded by these mutant odhA genes are shown in amino acids 37 to 1256 of SEQ ID NOS: 45, 47, and 49. However, the mutant odhA gene having a mutation in the thiamine pyrophosphate binding region is not limited to these examples.

(2) 2-2 Type Mutation

This type of mutation is preferably a mutation introduced into the region of nucleotides 1094 to 1114 of the odhA gene (SEQ ID NO: 9) which causes deletion and/or substitution of one or more amino acid residues selected from Asp at position 218, Val at position 219, Ile at position 220, Asp at position 221, Gly at position 222, Lys at position 223, and Pro at position 224 in SEQ ID NO: 10. The 2-2 type mutation is preferably a mutation which deletes Asp at position 218 in SEQ ID NO: 10. Examples of the odhA gene having this mutation include an odhA gene having a nucleotide sequence of nucleotides 443 to 4213 of SEQ ID NO: 11, or an odhA gene having a nucleotide sequence of nucleotides 551 to 4213 of SEQ ID NO: 11. The amino acid sequences of the mutant α-KGDH encoded by these genes are shown in SEQ ID NO: 12 or amino acid numbers 37 to 1256 of SEQ ID NO: 12, respectively. The nucleotide sequence of SEQ ID NO: 11 has the mutations to delete "gacgt" at 1094 to 1098 and replaces "ag" at 1110 to 1111 with "ggcc" in the nucleotide sequence shown in SEQ ID NO: 9. The 2-2 type mutation is also preferably a mutation which replaces one or more amino acids selected from Val at position 219, Ile at position 220, Asp at position 221, Gly at position 222, and Lys at position 223. Although the amino acids which replace these amino acids are not particularly limited, Val at position 219 is preferably replaced with an amino acid other than an aliphatic hydrophobic amino acid such as Ile and Leu, Ile at position 220 is preferably replaced with an amino acid other than an aliphatic hydrophobic amino acid such as Leu, Asp at position 221 is preferably replaced with an amino acid other than an acidic amino acid such as Glu, and Gly at position 222 is preferably replaced with an amino acid other than a simple amino acid such as Ala. More preferably, Val at position 219, Ile at position 220, and Asp at position 221 are replaced with basic amino acids such as His, Arg and Lys, Gly at position 222 is replaced with an amino acid having amide-containing side chain such as Asp and Gln, and Lys at position 223 is replaced with an amino acid such as Gly and Ala.

However, mutant odhA gene having 2-2 type mutation is not limited to these examples.

(3) GN2-2 Type Mutation

This mutation includes both the GN type mutation and the 2-2 type mutation. Examples of the odhA gene having this mutation include an odhA gene having a nucleotide sequence of nucleotides 443 to 4213 of SEQ ID NO: 15, or an odhA gene having a nucleotide sequence of nucleotides 551 to 4213 of SEQ ID NO: 15. The amino acid sequences of the mutant α-KGDH encoded by these genes are shown in SEQ ID NO: 16 or amino acids 37 to 1254 of SEQ ID NO: 16, respectively. However, the mutant odhA gene having a GN2-2 type mutation is not limited to these examples.

Other kinds of mutant odhA genes used in the present invention may be screened by using a yggB mutant strain, such as ATCC13869-L as described in Example 5 shown below. That is, a random mutation is introduced into the odhA gene and used to transform the yggB mutant strain. A strain which grows almost at the same growth rate as a wild-type strain or a non-mutated strain and exhibits α-KGDH activity which is less than half that of the wild-type strain or non-mutated strain is selected from the transformants, followed by sequence determination. Thereby, mutant odhA genes can be obtained.

A mutant E1o subunit of the α-KGDH complex encoded by the above-described mutant odhA gene is a protein which has α-KGDH activity which is less than half that of a wild-type or non-mutated strain by forming a complex with the E2o and E3 subunits of the α-KGDH complex, and does not cause severe growth retardation of a coryneform bacterium when it is expressed in the coryneform bacterium.

Such properties of the mutant E1o subunit are considered to be maintained even if one or several amino acids other than the specific amino acids replaced in the above-described GN type or 2-2 type mutants, for example, amino acids that do not influence the enzymatic activity are replaced by other amino acids. Therefore, in the above-mentioned amino acid sequences of the mutant E1o subunit protein (e.g., SEQ ID NOS: 12, 14, 16, 45, 47 and 49 or amino acids 37 to 1256 of SEQ ID NOS: 12, 45, 47 and 49, amino acids 37 to 1255 of SEQ ID NO: 14 and amino acids 37 to 1254 of SEQ ID NO: 16), one or several amino acids other than the specific amino acids substituted in the GN type or 2-2 type mutants may be replaced, so long as the encoded protein exhibits α-KGDH activity less than half of a wild-type α-KGDH complex by forming a complex together with α-KGDH E2o subunit and E3 subunit proteins. Here, "several" means preferably 2 to 20, more preferably 2 to 10, and particularly preferably 2 to 5. Such amino acid substitution may be one caused by a naturally occurring mutation arising from individual difference and difference in species of bacterium from which odhA gene is derived. For example, mutant odhA gene having a nucleotide sequence encoding amino acid sequence of SEQ ID NO: 51 whereby amino acids corresponding to the above-mentioned GN-type mutation or 2-2 type mutation are deleted and/or substituted can also be used in the present invention. Such amino acids corresponding to the GN-type mutation or 2-2 type mutation in the amino acid sequence of SEQ ID NO: 51 can be easily identified by aligning the amino acid sequences of SEQ ID NOS: 10 and 51.

The above-mentioned substitution is preferably a conservative substitution. In the case of aromatic amino acids, conservative substitutions are referred to substitutions between phe, trp, and tyr for each other. In the case of hydrophobic amino acids, conservative substitutions are referred to substitutions between leu, ile, and val for each other. In the case of polar amino acids, conservative substitutions are referred to substitutions between gln and asn for each other. In the case of basic amino acids, conservative substitutions are referred to substitutions between arg, lys, and his for each other. In the case of acidic amino acids, conservative substitutions are substitutions between asp and glu for each other. In the case of hydroxyl group-containing amino acids, conservative substitutions are referred to substitutions between ser and thr for each other. The conservative substitutions also include: substitution of ser or thr for ala, substitution of gln, his, or lys for arg; substitution of glu, gln, lys, his, or asp for asn; substitution of asn, glu, or gln for asp; substitution of ser or ala for cys; substitution of asn, glu, lys, his, asp, or arg for gln; substitution of asn, gln, lys, or asp for glu; substitution of vfor gly; substitution of asn, lys, gln, arg, or tyr for his; substitution of leu, met, val, or phe for ile; substitution of ile, met, val, or phe for leu; substitution of asn, glu, gln, his, or arg for lys; substitution of ile, leu, val or phe for met; substitution of trp, tyr, met, ile, or leu for phe; substitution of thr or ala for ser; substitution of ser or ala for thr; substitution of phe or tyr for trp; substitution of his, phe, or trp for tyr; and substitution of met, ile, or leu for val.

When the E1o subunit and E2o subunit are encoded by a single odhA gene, the α-KGDH complex may include the protein of SEQ ID NO: 10 (or amino acids 37 to 1257 of SEQ ID NO: 10) and the protein of SEQ ID NO: 18. When the E1o subunit is encoded by the odhA gene and the E2o subunit is encoded by the gene of SEQ ID NO: 27, the α-KGDH complex may include the protein of SEQ ID NO: 10, the protein of SEQ ID NO: 18, and the protein of SEQ ID NO: 28.

A mutant odhA gene of the present invention is a gene encoding the above-mentioned mutant α-KGDH E1o subunit. The mutant odhA gene of the present invention may be genes that hybridize with a polynucleotide each having the nucleotide sequence of nucleotides 443 to 4213 of SEQ ID NO: 11, 13, or 15, a polynucleotide each having the nucleotide sequence of nucleotides 443 to 4210 of SEQ ID NO: 44, 46 or 48, or with the nucleotide sequence of nucleotide numbers of 551 to 4213 of SEQ ID NO: 11, 13, 15, or with the nucleotide sequence of nucleotides 551 to 4210 of SEQ ID NO: 44, 46, or 48, or with a probe prepared from the sequences under stringent conditions so long as the gene encodes a protein that exhibits α-KGDH activity less than half that of a wild-type α-KGDH complex by forming a complex together with the E2o subunit and E3 subunit proteins. Examples of stringent conditions include those under which DNAs hybridize to each other at a salt concentration with washing typical of Southern hybridization, i.e., washing once or preferably 2–3 times under 1×SSC, 0.1% SDS at 60° C., preferably 0.1×SSC, 0.1% SDS at 60° C., more preferably 0.1×SSC, 0.1% SDS at 68° C.

<3> Method of Producing L-Glutamic Acid

L-glutamic acid can be produced by culturing the coryneform bacterium of the present invention in a medium to cause accumulation of L-glutamic acid in the medium and/or in the bacterial cells, and collecting the L-glutamic acid from the medium and/or the bacterial cells. In the production method of the present invention, L-glutamic acid is produced preferably by culturing the cornyeform bacterium of the present invention, for example, at 25 to 40° C. for 8 to 120 hours. If a strain which exhibits a sufficient growth rate at low temperatures but exhibits decreased growth rate at high temperatures such as the GN-2-2 strain shown in the Examples is used for L-glutamic acid production, it is preferable to culture such a strain at a low temperature such as 25 to 30 ° C. for 8 to 30 hours so that the strain can grow; and then incubate the obtained bacterial cells at high temperature such as 34 to 40° C. for 16 to 48 hours so that the strain can produce L-glutamic acid.

The culture medium may be an ordinary medium that contains a carbon source, a nitrogen source, an inorganic salt, and optionally organic micronutrients such as amino acids and vitamins. Either a synthetic medium or a natural medium may be used. Any kinds of the carbon source and nitrogen source may be used so long as they can be utilized by the strain to be cultured.

Saccharides such as glucose, glycerol, fructose, sucrose, maltose, mannose, galactose, starch hydrolysate, and molasses may be used as the carbon source. In addition, organic acids such as acetic acid and citric acid, and alcohols such as ethanol may also be used alone or in combination as a carbon source. Ammonia, ammonium salts such as ammonium sulfate, ammonium carbonate, ammonium chloride, ammonium phosphate, and ammonium acetate, nitrates, and the like may be used as the nitrogen source. Amino acids, vitamins, fatty acids, nucleic acids, substances containing peptone, casamino acid, yeast extract, and soybean protein decomposition products may be used in a slight amount as the organic nutrients. When an auxotrophic mutant strain that requires an amino acid etc. for growth is used, such a required nutrient is preferably added. Phosphates, magnesium salts, calcium salts, iron salts, manganese salts, and the like can be used as inorganic salts.

Preferably, aerobic culturing is performed by controlling the fermentation temperature and adjusting the pH of the culture medium to 3 to 9. When the pH decreases during the culture, the medium is neutralized by adding alkali such as calcium carbonate or ammonia gas. Culture for about 10 to about 120 hours results in accumulation of a considerable amount of L-glutamic acid in the medium.

Furthermore, the culture may be performed by using a liquid medium adjusted to conditions under which the produced L-glutamic acid crystallizes and precipitates. The conditions under which L-glutamic acid crystallizes include pH 5.0 to 4.0, preferably pH 4.5 to 4.0, more preferably pH 4.3 to 4.0, particularly preferably pH 4.0 (EP1233069, EP1233070).

Collection of L-glutamic acid from the medium after completion of the culture may be performed by conventional methods. L-glutamic acid may be collected, for example, by removing bacterial cells from the medium and concentrating L-glutamic acid or by using ion exchange chromatography. When the culture is performed under conditions under which L-glutamic acid crystallizes and precipitates, the crystallized L-glutamic acid can be collected, for example, by centrifugation or filtration. In this case, L-glutamic acid dissolved in the medium may also be collected after crystallization of the dissolved L-glutamic acid.

EXAMPLES

Hereinafter, the present invention will be more specifically explained by referring to the following non-limiting examples.

Example 1

<1> Construction of a Vector Carrying the sacB Gene
(A) Construction of pBS3

A sacB gene (SEQ ID NO: 19) was obtained by PCR using a chromosomal DNA of *Bacillus subtilis* as a template and the oligonucleotides of SEQ ID NOS: 21 and 22 as primers. The PCR was performed using LAtaq (available from TaKaRa) according to the program of one cycle of pre-denaturation at 94° C. for 5 minutes; and 25 cycles of denaturation at 94° C. for 30 seconds, annealing at 49° C. for 30 seconds, and elongation at 72° C. for 2 minutes. The obtained PCR product was purified by a conventional method, and then digested with BglII and BamHI and blunt-ended. The fragment was inserted into pHSG299 which had been digested with AvaII and blunt-ended. The resulting DNA was used to transform competent cells of *Escherichia coli* JM109 (available from Takara Bio). Then, the transformed bacterial cells were applied onto an LB agar plate containing 25 µg/ml of kanamycin (hereinafter, abbreviated as "Km"), and incubated for one night. Thereafter, colonies that appeared were selected as transformants. Plasmids were isolated from the obtained transformants and the plasmid having an insert of the object PCR product was named pBS3. FIG. 1 shows the procedure for constructing pBS3.

(B) Construction of pBS4S

The SmaI recognition site in the kanamycin-resistant gene on pBS3 was destroyed by nucleotide substitution using cross-over PCR without causing amino acid substitution. First, PCR was performed using pBS3 as a template and synthetic DNAs of SEQ ID NOS: 23 and 24 as primers to obtain an N-terminal fragment of the kanamycin-resistant gene. On the other hand, to obtain a C-terminal fragment of kanamycin-resistant gene, PCR was performed using pBS3 as a template and synthetic DNAs of SEQ ID NOS: 25 and 26 as primers. The PCR was performed using Pyrobest DNA Polymerase (available from Takara Bio) according to the program of pre-denaturation at 98° C. for 5 minutes; and 25 cycles of denaturation at 98° C. for 10 seconds, annealing at 57° C. for 30 seconds, and elongation at 72° C. for 1 minute. SEQ ID NOS: 24 and 25 are partially complementary to each other and do not contain the SmaI recognition site.

Then, to obtain a full-length fragment of the mutant kanamycin-resistant gene without the SmaI recognition site, the above-mentioned N-terminal and C-terminal gene products were mixed with each other in substantially equimolar amounts. PCR was performed using the gene products as a template and synthetic DNAs of SEQ ID NOS: 23 and 26 as primers to obtain a mutation-introduced Km resistant gene. The PCR was performed using Pyrobest DNA Polymerase (available from Takara Bio) according to the program of pre-denaturation at 98° C. for 5 minutes; and 25 cycles of denaturation at 98° C. for 10 seconds, annealing at 57° C. for 30 seconds, and elongation at 72° C. for 1.5 minutes.

Figure 2:
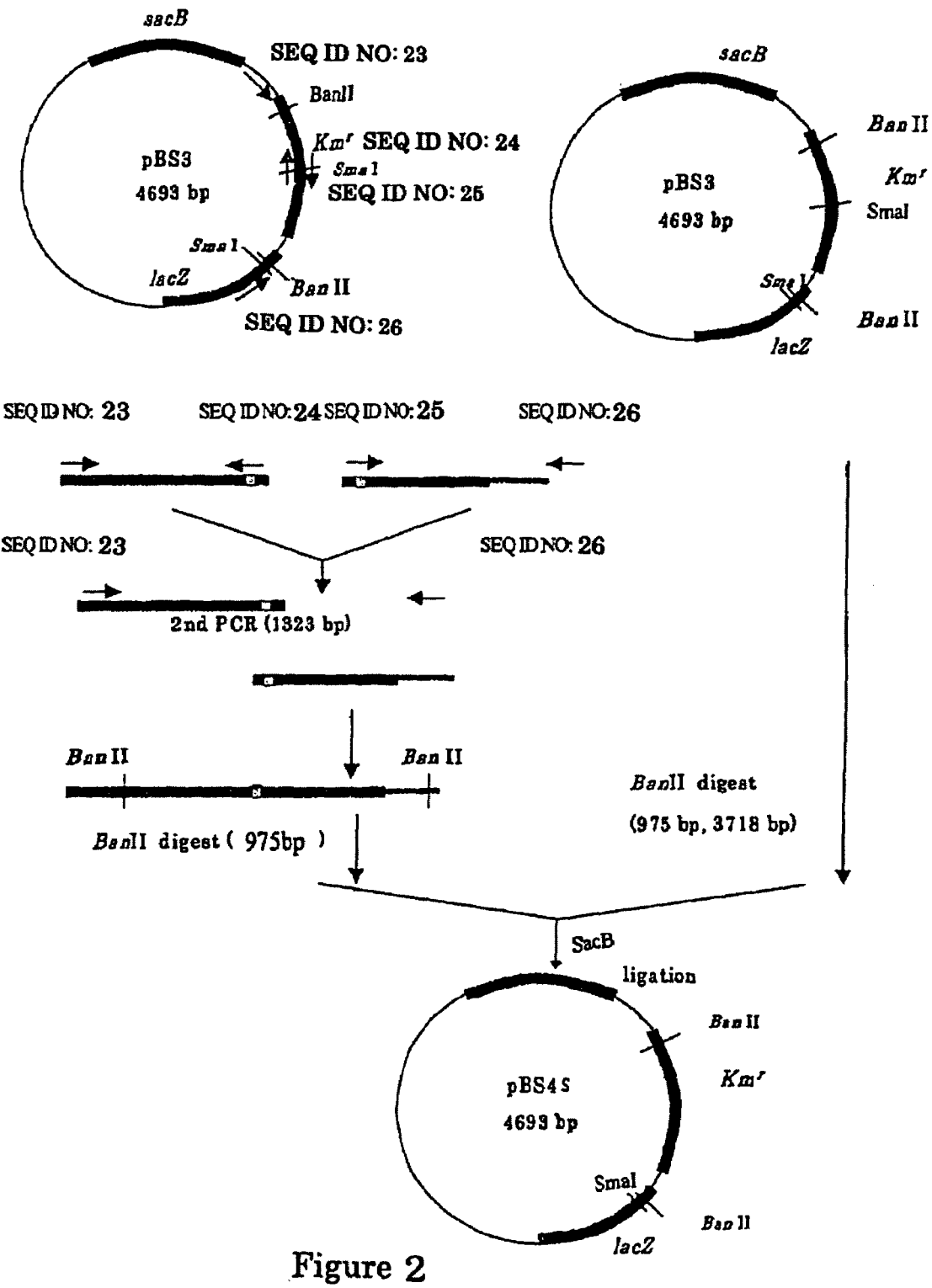
FIG. 2 is shows the construction of plasmid pBS4S.

The PCR product was purified by a conventional method, and then digested with BanII and then inserted into the above-described BanII recognition site of pBS3. The resulting plasmid was used to transform competent cells of *Escherichia coli* JM109 (available from Takara Bio). That is, the transformed bacterial cells were applied onto LB agar medium containing 25 µg/ml of kanamycin, and incubated for one night. Thereafter, colonies that appeared were selected as transformants. Plasmids were isolated from the obtained transformants and the plasmid having an insert of the object PCR product was named pBS4S. FIG. 2 shows the procedure for constructing pBS4S.

<2> Introduction of odhA Mutation (GN-Type) into *C. glutamicum* ATCC13969 Strain The sequence of odhA that encodes α-ketoglutarate dehydrogenase of coryneform bacteria has already been reported (Microbiology 142, 3347–3354 (1996), GenBank accession No. D84102).

Analysis of the nucleotide sequence of the L-glutamic acid-producing bacterium strain GN which the inventors of the present invention had succeeded in breeding revealed that this strain has deletions of the nucleotides 2538 and 2543 to 2547 in the nucleotide sequence of the odhA gene (SEQ ID NO: 9) as shown in Table 1. In Table 1, amino acid sequence of mutant E1o subunit encoded by the mutant odhA gene is also shown.

TABLE 1

| Strain | Nucleotide sequence of odhA gene |
|---|---|
| ATCC13869 | GCT AAG CTG CGT GGC TAC GAC GTC GGA GGC ACC ATC |
| OAGN | GCT AAG C-G CGT --- --C GAC GTC GGA GGC ACC ATC |
| Strain | Amino acid sequence of E1o subunit |
| ATCC13869 | Ala Lys Leu Arg Gly Tyr Asp Val Gly Gly Thr Ile |
| OAGN | Ala Lys Arg Val --- --- Asp Val Gly Gly Thr Ile |

Figure 3:
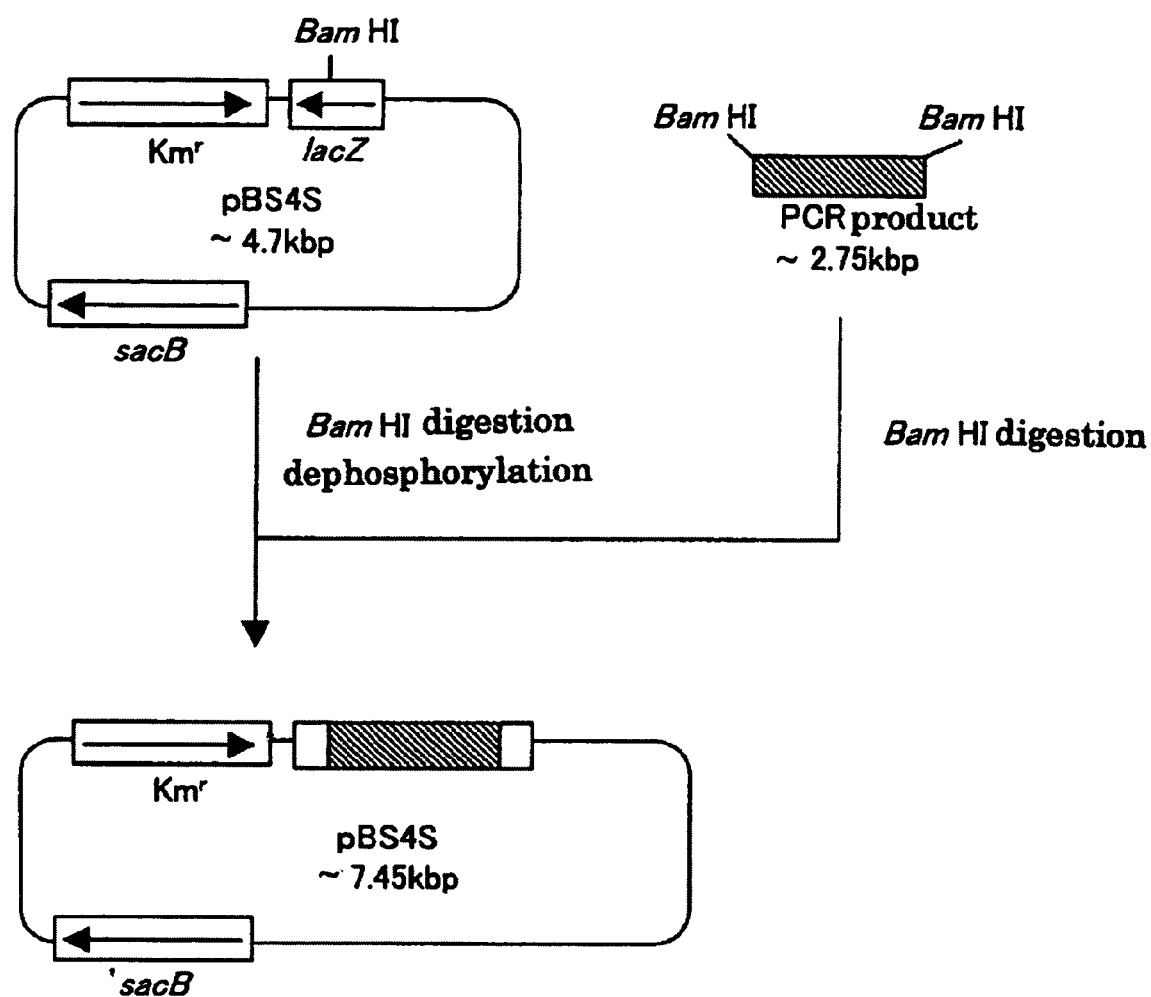
FIG. 3 shows the construction of plasmid pBSOAGN.

Then, this mutant odhA gene was introduced into *C. glutamicum* 2256 strain (ATCC13869) and evaluated. At first, a plasmid for introducing these mutations into *C. glutamicum* 2256 strain (ATCC13869) was prepared. A chromosomal DNA was extracted from the above-mentioned GN strain using Bacterial Genomic DNA Purif. Kit (manufactured by MS Technosystems Co., Ltd.) and PCR was performed using the obtained chromosomal DNA as a template and oligonucleotides of SEQ ID NOS: 1 and 2 as primers. PCR was performed using Pyrobest polymerase (available from Takara Bio) according to the program of 30 cycles of denaturation at 98° C. for 10 seconds, annealing at 50° C. for 30 seconds, and elongation at 72° C. for 3 minutes to amplify a fragment of about 2.75 kb. The primers contain a BamHI recognition sequence at the 5'-end and are designed to amplify the region of nucleotide numbers 1521 to 4270 of the sequence of GenBank accession No. D84102. The amplified fragment was digested with BamHI and ligated to pBS4S vector digested with BamHI (Ligation kit Ver. 2, using a product available from Takara Bio), and thereby plasmid pBSOAGN was obtained (FIG. 3 shows the construction procedure).

pBSOAGN was introduced into *C. glutamicum* ATCC13869 strain by an electric pulse method (JPO2-207791A) and the obtained bacterial cells were applied to CM-Dex agar medium (5 g/l glucose, 10 g/l polypeptone, 10 g/l yeast extract, 1 g/l $KH_2PO_4$, 0.4 g/l $MgSO_4.7H_2O$, 0.01 g/l $FeSO_4.7H_2O$, 0.01 g/l $MnSO_4.4–5H_2O$, 3 g/l urea, 1.2 g/l soybean protein hydrolysate, and 20 g/l agar, pH adjusted to 7.5) containing 25 μg/ml of kanamycin. After culturing at 25° C., it was confirmed by using PCR that the colonies which appeared were once recombinant strains in which pBSOAGN was incorporated by homologous recombination on the chromosome. The PCR was performed using the chromosomal DNA of a candidate strain as template and an oligonucleotide having a nucleotide sequence specific to the sequence of pBS4S (SEQ ID NO: 3) and an oligonucleotide having a nucleotide sequence specific to the sequence on the chromosome (SEQ ID NO: 4) as primers. That is, since the sequence of pBS4S is absent on the chromosome of a non-recombinant strain, no fragment is amplified by PCR if the candidate strain is not a recombinant strain. The obtained once recombinant strains were cultured at 25° C. for one day in CM-Dex liquid medium containing 25 μg/ml kanamycin and the obtained culture was diluted appropriately and applied onto S10 plate which has a composition of the above-mentioned CM-Dex medium whereby 5 g/l glucose is replaced by 10 g/l of sucrose. Several strains that grew on the S10 plate and showed kanamycin sensitivity were selected, and then the nucleotide sequence of the odhA sequence was confirmed by the method of Sanger (J. Mol. Biol., 143, 161 (1980)). The nucleotide sequence was analyzed by genetic Analyzer ABI310 (manufactured by Applied Biosystems) using BigDye terminator sequencing kit (manufactured by Applied Biyosystems). The thus obtained strain carrying the GN-type mutant odhA gene was named ATCC13869 OAGN.

<3> Introduction of the 2-2 Type Mutant odhA Gene into *C. glutamicum* ATCC13869 Strain Analysis of the nucleotide sequence of the L-glutamic acid-producing "2-2" strain which the inventors of the present invention had succeeded in breeding revealed that the strain contains deletions of the nucleotides 1094 to 1098 and replacement of "ag" at 1110 to 1111 with "ggcc" in the odhA gene (SEQ ID NO: 9) as shown in Table 2. In Table 2, amino acid sequence of mutant E1o subunit encoded by the mutant odhA gene is also shown.

Figure 4:
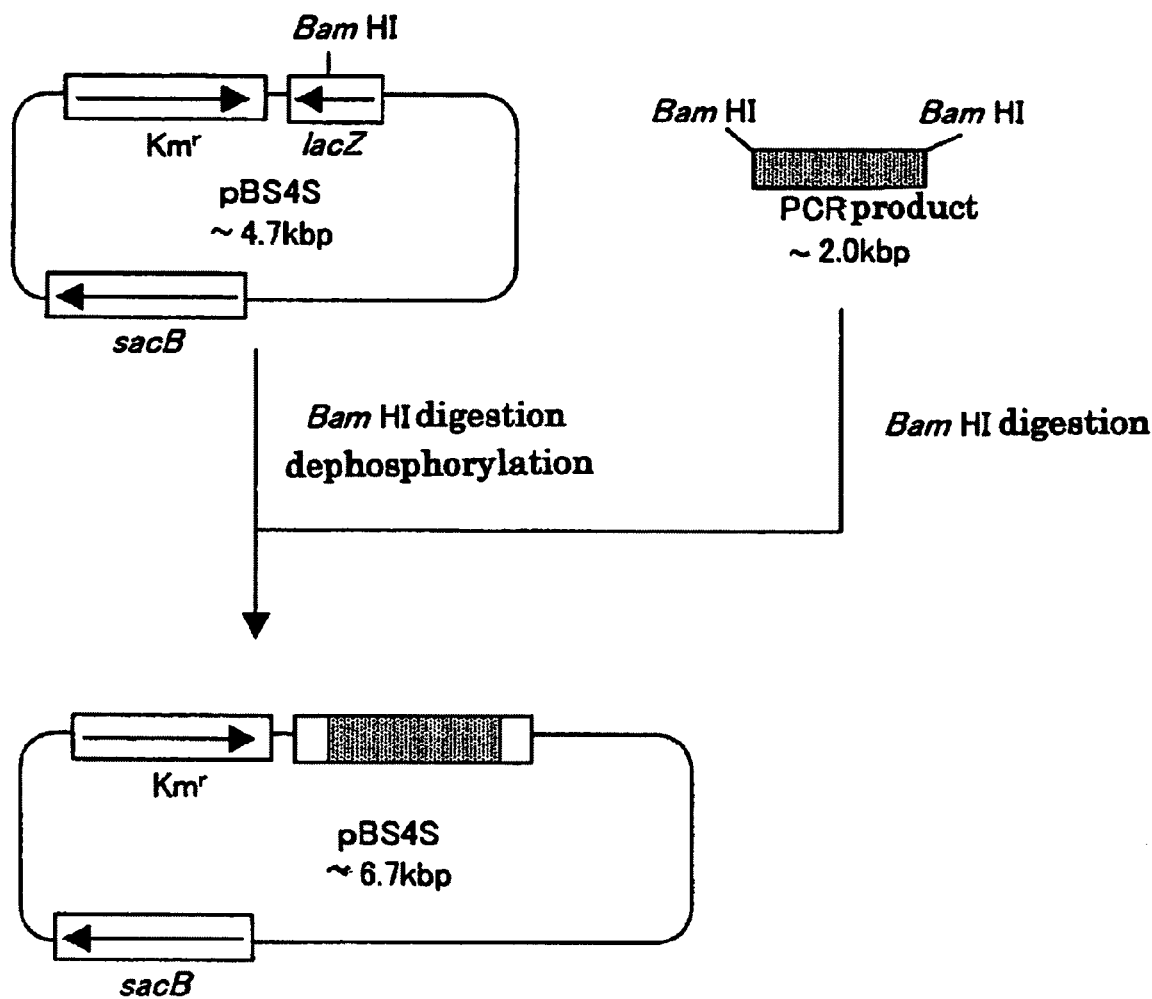
FIG. 4 shows the construction of plasmid pBSOA2-2.

Then, this mutant odhA gene was introduced into *C. glutamicum* 2256 strain (ATCC13869) and evaluated. At first, a plasmid for introducing these mutations into *C. glutamicum* 2256 was prepared. A chromosomal DNA was isolated from the 2-2 strain using Bacterial Genomic DNA Purif. Kit (manufactured by MS Technosystems Co., Ltd.) and PCR was performed using this chromosomal DNA as a template and oligonucleotides of SEQ ID NOS: 5 and 6 as primers. PCR was performed using TaKaRa Ex Taq (available from Takara Bio) according to the program of 25 cycles of denaturation at 94° C. for 30 seconds, annealing at 55° C. for 10 seconds, and elongation at 72° C. for 2 minutes to amplify a fragment of about 2.0 kb. The primers contain a BamHI recognition sequence at the 5'-end and designed to amplify the region of nucleotides 51 to 2150 of the nucleotide sequence of GenBank accession No. D84102. The amplified fragment was digested with BamHI and ligated to pBS4S vector digested with BamHI using Ligation kit Ver. 2 of Takara Bio, and thereby the plasmid pBSOA2-2 was obtained (FIG. 4 shows the construction diagram). The same procedure described in Example 1<2> was performed to obtain a strain carrying the 2-2 type mutant odhA gene (ATCC13869 OA2-2 strain).

<4> Introduction of 2-2 Type Mutation into GN Type odhA Gene of ATCC13869 OAGN Strain According to the same procedures as described in Example 1<2>, the plasmid pBSOA2-2 constructed in Example 1<3> was introduced into ATCC13869 OAGN strain prepared in Example 1<2> to obtain ATCC13869 strain carrying both the GN type and 2-2 type mutations in odhA gene. Hereinafter, a double mutation consisting of 2-2 type mutation and GN type mutation is also called GN2-2 mutation.

Although the mutant strains were prepared using mutant odhA genes amplified by PCR using a chromosomal DNA from the GN strain or 2-2 strain as a template in Example 1<2> to <4>, they can also be prepared by using mutant odhA genes obtained by site-directed mutagenesis technique such as those using Mutan-Super Express Km kit (Takara Bio). For example, a plasmid having a similar structure to pBSOAGN prepared in Example 1<2> can be obtained as follows. That is, an odhA gene fragment is prepared by PCR using synthetic DNAs of SEQ ID NOS: 2 and 5 as primers and a chromosomal DNA of a wild-type odhA gene as a template, and the resultant PCR fragment is cloned into the BamHI recognition site of plasmid pKF19k attached to Mutan-Super Express Km kit. Next, another PCR is performed using a template of the obtained plasmid and primers of a synthetic DNA of SEQ ID NO: 7 having phosphorylated 5'-end and the selection primer attached to Mutan-Super Express Km kit. Transformation of $sup^0$ *E. coli*, for example, MV1184 strain (available from Takara Bio) with the

TABLE 2

| Strain | Nucleotide sequence of odhA gene |
|---|---|
| ATCC13869 | AAC TCC TAC GAC GTC ATC GAC GGC AAG CCA ACC CTG |
| OA2-2 | AAC TCC TAC --- CAT CGA CGG CAG GCC CCA ACC CTG |

| Strain | Amino acid sequence of E1o subunit |
|---|---|
| ATCC13869 | Asn Ser Tyr Asp Val Ile Asp Gly Lys Pro Thr Leu |
| OA2-2 | Asn Ser Tyr --- His Arg Arg Gln Ala Pro Thr Leu | obtained PCR product results in construction of a plasmid containing the mutant odhA gene fragment. Finally, the fragment is digested with BamHI and inserted into the pBS4S vector, and thereby a plasmid similar to pBSOAGN can be constructed.

Similarly, to obtain odhA gene containing the 2-2 type mutation, a plasmid similar to pBSOA2-2 can be constructed by using the synthetic DNA of SEQ ID NO: 8 having phosphorylated 5'-end instead of the synthetic DNA of SEQ ID NO: 7 having phosphorylated 5'-end in the procedure as described above.

Furthermore, to obtain odhA gene containing GN2-2 double mutations, a fragment containing the GN-type mutation is excised or PCR-amplified from the above-described plasmid similar to pBSOAGN and used to replace the corresponding fragment on the above-described plasmid similar to pBSOA2-2.

Example 2

Comparison of the ability of strains ATCC13869 OAGN, OA2-2, and OAGN2-2 to degrade glutamic acid While strains carrying a wild-type odhA gene can assimilate L-glutamic acid in a medium, the strains in which the activity of α-KGDH is weakened or eliminated due to the odhA mutation is presumed to also have a decreased ability to degrade glutamic acid. Then, the ability to degrade glutamic acid was determined using each of the odhA mutant strains ATCC13869 OAGN, OA2-2, and OAGN2-2 prepared in Example 1<2> to <4>. Each strain was cultured on a CM-Dex plate for one day at 25° C. and then inoculated into a liquid medium composed of 20 g/l sodium glutamate, 2.64 g/l $(NH_4)_2SO_4$, 0.5 g/l $KH_2PO_4$, 0.5 g/l $K_2HPO_4$, 0.25 g/l $MgSO_4.7H_2O$, 0.01 g/l $FeSO_4.7H_2O$, 0.01 g/l $MnSO_4.4–5H_2O$, 0.01 g/l $CaCl_2$, 0.02 mg/l $CuSO_4$, 40 g/l MOPS, 0.03 g/l protocatechinic acid, 200 μg/l vitamin B1, and 300 μg/l biotin (adjusted to pH 6.7 with NaOH), followed by culturing at 25° C. and 34° C. for 50 hours. The amounts of glutamic acid at the starting point, and after 25 hours and 50 hours of the culture were measured, respectively and the amounts of degraded glutamic acid were compared between the strains cultured at 25° C. and 34° C. Table 3 shows the results. In particular, the GN2-2 mutant strain exhibited a significant decrease in the amount of degraded glutamic acid, especially when the culture temperature was 34° C. These results suggest that introduction of the GN2-2 mutation can efficiently reduce the α-KGDH activity and a strain having this mutation is preferably used in L-glutamic acid production.

TABLE 3

| | Amount of degraded glutamic acid | | | |
| --- | --- | --- | --- | --- |
| | 25 Hours | | 50 Hours | |
| Strains | 25° C. | 34° C. | 25° C. | 34° C. |
| ATCC13869 | 15 | 15 | 15.4 | 15.4 |
| OAGN | 3.8 | 5.8 | 9.4 | 10.0 |
| OA2-2 | 11.7 | 15.1 | 15.4 | 15.4 |
| OAGN2-2 | 0.7 | 0.5 | 4.9 | 1.0 |

(Unit: g/l)

Example 3

Comparison of the α-KGDH activity of ATCC13869 OAGN, OA2-2, and OAGN2-2 strains

The α-KGDH activity of the strains ATCC13869 OAGN, OA2-2, and OAGN2-2 was measured using the culture broth collected after 4 hours from the start of the culture in Example 4 as described below. The activity was measured according to the method described in Agric. Biol. Chem., 44(8), p1897 (1980). Specifically, after bacterial cells were washed with 0.2% sodium chloride, they were suspended in a buffer solution of 100 mM TES-NaOH (pH 7.5) containing 30% glycerol. The bacterial cells were sonicated using Bioruptor (Olympus) and then centrifuged to remove non-ruptured bacterial cells, followed by gel filtration with the same buffer using Sephadex-G25 (Amersham Pharmacia). The thus obtained preparation was used as a crude enzyme solution. The crude enzyme solution was added to a reaction system containing 100 mM TES-NaOH (pH 7.7), 5 mM $MgCl_2$, 0.2 mM CoA, 0.3 mM cocarboxylase, 1 mM α-ketoglutaric acid, 3 mM L-cysteine, and 1 mM acetylpyridine-adenine-dinucleotide and absorption at 365 nm at 31.5° C. was measured using Hitachi spectrophotometer U-2001. In the measurement of the protein concentration in the crude enzyme solution, proteinAssay (Bio-Rad) was used. Bovine serum albumin was used as a standard protein.

Table 4 shows the results of the measurement of the α-KGDH activity. Introduction of the GN type mutation, 2-2 type mutation, and GN2-2 type mutation leads to a decrease in the α-KGDH as compared to ATCC13869. In particular, in the case of GN2-2 type mutation-introduced strain, a considerable decrease in the activity was observed. This indicates that the GN type mutation, 2-2 type mutation, and GN2-2 type mutation are mutations that reduce the α-KGDH activity.

TABLE 4

| | α-KGDH activity | |
| --- | --- | --- |
| strains | Culture temperature 25° C. | Culture temperature 34° C. |
| ATCC13869 | 0.036 | 0.021 |
| OAGN | 0.001 | 0.002 |
| OA2-2 | 0.007 | 0.009 |
| OAGN2-2 | 0.001> | 0.001> |

(Unit: ΔAbs/min/mg protein)

Example 4

Comparison of L-glutamic acid-producing ability of the strains ATCC13869 OAGN, OA2-2, and OAGN2-2

The L-glutamic acid-producing ability of the strains ATCC13869 OAGN, OA2-2, and OAGN2-2 were examined in ajar fermenter culture. First, the above-mentioned four strains were cultured on a CM-Dex agar medium at 25° C. for one day and the obtained bacterial cells were inoculated in 300 ml of a sterilized seed medium containing 60 g/l glucose, 1.54 g/l $H_3PO_4$, 1.45 g/l KOH, 0.9 g/l $MgSO_4.7H_2O$, 0.01 g/l $FeSO_4.7H_2O$, 670 μg/l vitamin B1, 3,200 μg/l biotin, 0.28 g/l DL-Met, 1.54 g/l soybean protein hydrolysate, and 0.1 ml/l defoaming agent AZ-20R, and cultured until the sugar was completely consumed. During the culture, the medium was stirred with aeration of 1/1 VVM so that the concentration of dissolved oxygen was maintained not less than 5%. The pH during the culture was controlled to pH 7.2 with ammonia gas. Then, 30 ml of the obtained seed culture was inoculated in 270 ml of a main culture medium containing 80 g/l glucose, 3.46 g/l $KH_2PO_4$, 1.0 g/l $MgSO_4.7H_2O$, 0.01 g/l $FeSO_4.7H_2O$, 0.01 g/l $MnSO_4.4–5H_2O$, 230 μg/l vitamin B1, 525 μg/l biotin, 0.35 g/l soybean protein hydrolysate, and 0.2 ml/l defoaming agent AZ-20R, and cultured at 25° C. or 34° C. During the culture, aeration was performed as described above. The pH during the culturing was controlled at pH 7.3 with ammonia gas.

Figure 5:
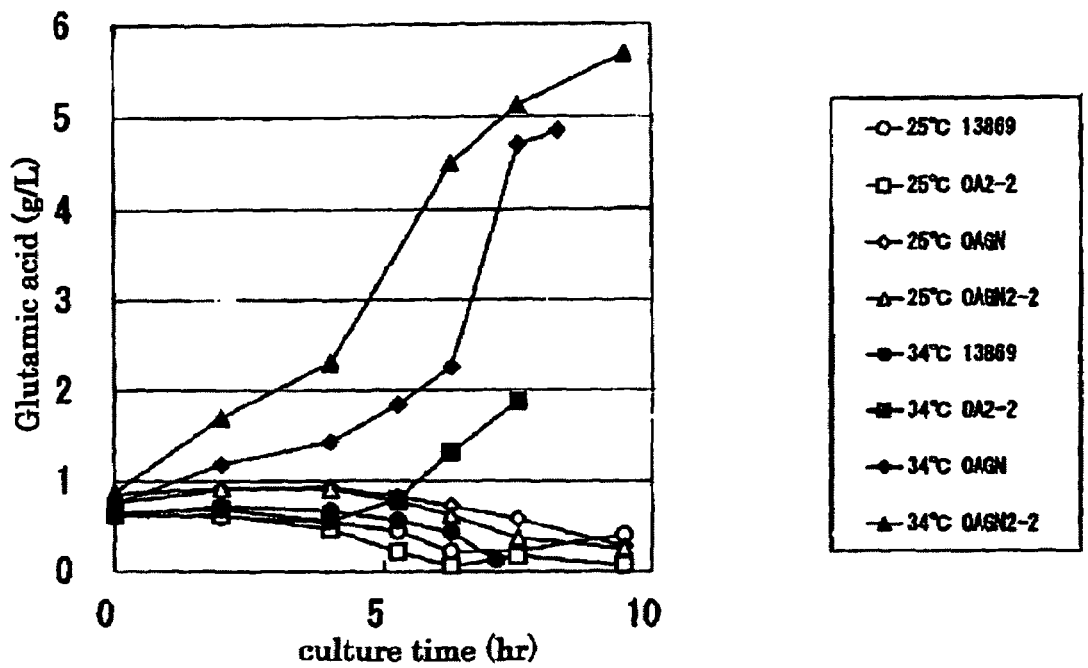
FIG. 5 shows the change in L-glutamic acid concentration when each strain is cultured.
Figure 6:
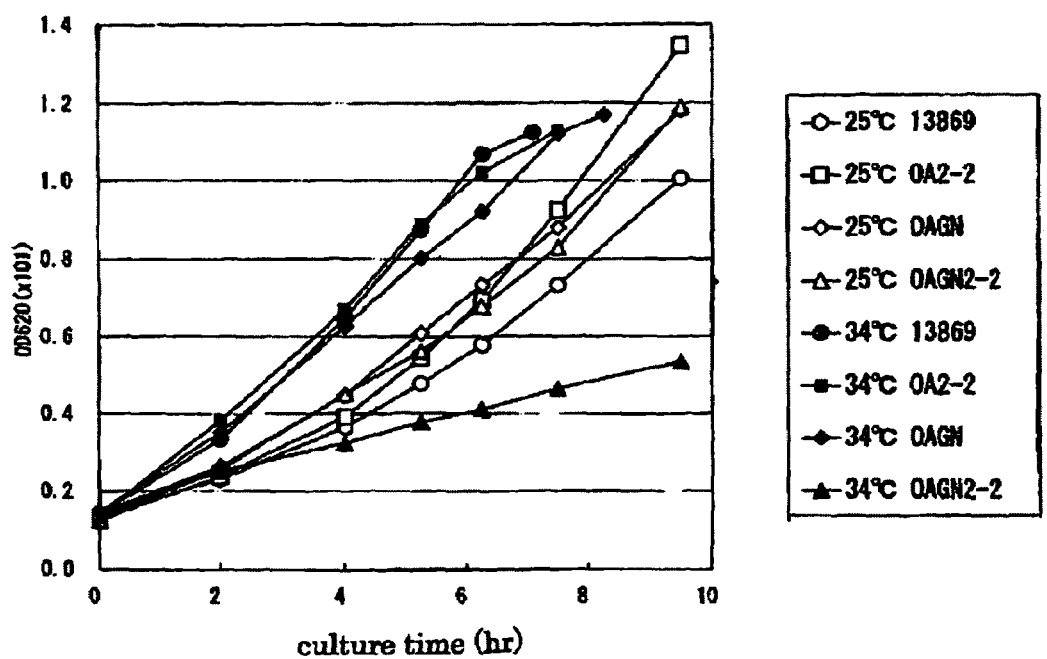
FIG. 6 shows the growth rate of each strain.
Figure 7:
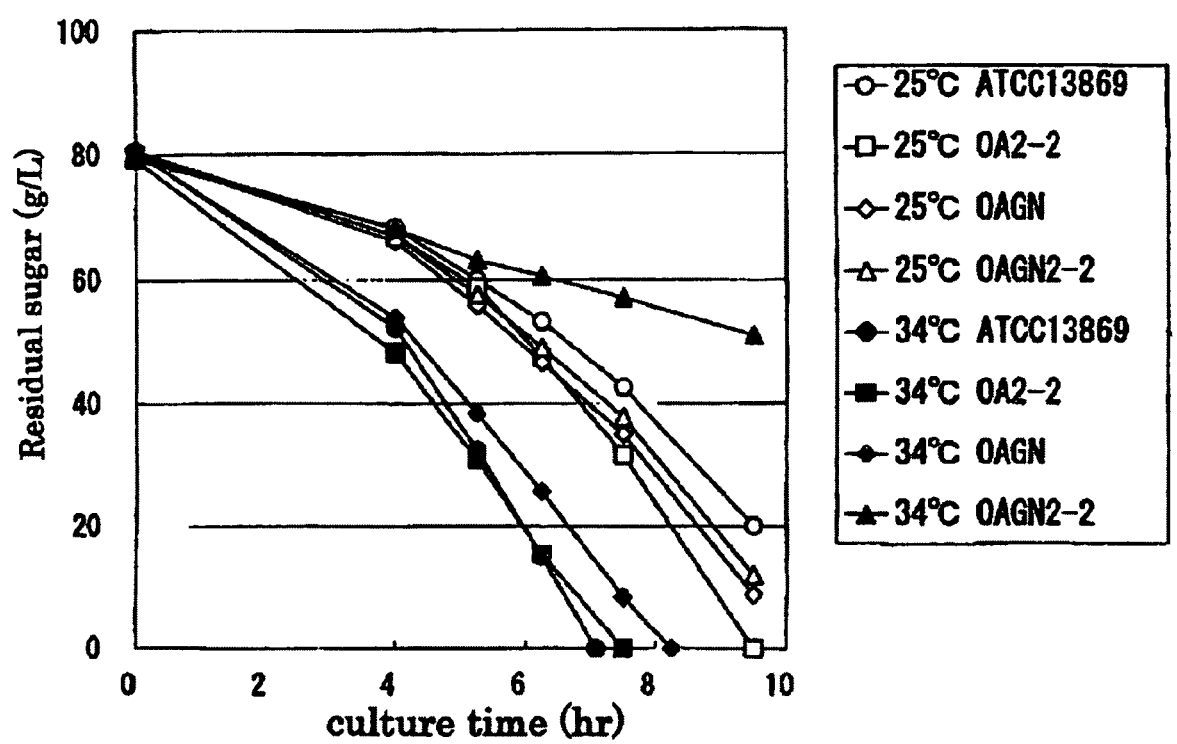
FIG. 7 shows the change in the amount of residual sugar when each strain is cultured.

Table 5 shows amount of accumulated L-glutamic acid after about 7.5 hours from the start of the culture. FIGS. 5, 6, and 7 show time courses of L-glutamic acid accumulation, bacterial cell amount, and residual sugar, respectively. ATCC13869 strain did not accumulate L-glutamic acid, whereas OAGN and OAGN2-2 mutant strains accumulated L-glutamic acid. In particular, when these strains were cultured at 34° C., the amounts of accumulated L-glutamic acid significantly increased. Each mutation-introduced strain showed almost the same growth rate as the wild-type strain.

From these results, it was confirmed that the GN type mutation, 2-2 type mutation, and GN2-2 type mutation are effective to increase L-glutamic acid production. Among these mutations, GN2-2 type mutation was found to have the most significant effect on the L-glutamic acid production.

TABLE 5

Amount of produced L-glutamic acid (Glu) of odhA mutation-introduced strains

| Strains | 25° C. Glu (g/L) | 34° C. Glu (g/L) |
| --- | --- | --- |
| ATCC13869 | 0.24 | 0.13 |
| OAGN | 0.18 | 1.88 |
| OA2-2 | 0.59 | 4.70 |
| OAGN2-2 | 0.38 | 5.13 |

Example 5

Screening of odhA mutant strains using a yggB mutant strain

<Construction of L30 type yggB Mutant Strain>

At first, a mutant strain having a mutation in the yggB gene was constructed from ATCC13869 strain. The L30 type mutation is a mutation which replaces "C" at position 1768 with "T" in the yggB gene (SEQ ID NO: 29). The mutant yggB gene having the L30 type mutation is shown in SEQ ID NO: 31 and the amino acid sequence encoded by the gene is shown in SEQ ID NO: 32. The mutant yggB gene was constructed by the same method as in Example 1. That is, a fragment encoding the N-terminus portion of the yggB gene was prepared by PCR using primers of SEQ ID NOS: 33 and 34 and a template of chromosomal DNA of the ATCC13869 strain. In a similar way, a fragment encoding the C-terminus portion of the yggB gene was prepared by PCR using primers of SEQ ID NOS: 35 and 36 and a template of chromosomal DNA of the ATCC13869 strain. Subsequently, a fragment of the yggB gene including the L30 type mutation was obtained by PCR using primers of SEQ ID NOS: 37 and 35 and a template of a mixture of equal amounts of the N-terminus fragment and C-terminus fragment. The obtained PCR product is digested by SacI and ligated to SacI-digested pBS4S, and thereby the plasmid for introducing the mutation is obtained (pBS4 yggB-L). The obtained pBS4 yggB-L was integrated into the chromosome of the ATCC13869 strain and then cured from the strain according to a similar method as in Example 1. The nucleotide sequence of yggB gene of the obtained kanamycin-resistant strain is determined and the strain in which yggB gene is replaced with L30 type was selected. The strain having yggB gene of SEQ ID NO: 31 was named ATCC13869-L strain. This strain can be used in the screening of odhA mutant genes.

<Construction of the yggB, odhA Double Mutant Strain>

Then, each of the mutations shown in Table 6 was introduced into the chromosomal odhA gene of ATCC13869-L strain. In Table 6, nucleotide sequences of the region corresponding to nucleotides 2528 to 2562 of SEQ ID NO: 9 of each strain are shown. In Table 7, amino acid sequences of the region corresponding to amino acids 696 to 707 of SEQ ID NO: 10 of each strain are shown.

The L30sucA8 strain in which odhA gene having nucleotide sequence of SEQ ID NO: 42 is introduced can be obtained as follows. The mutant odhA gene fragment is prepared by PCR using primers of SEQ ID NOS: 2 and 5. The obtained fragment is digested with BamHI and ligated to the BamHI site of plasmid pKF19m which is attached to Mutan-Super Express Km (Takara Bio). Then, PCR is performed using a primer of SEQ ID NO: 38 having a phosphorylated 5'-end and the selection primer of Mutan-Super Express Km, and the obtained PCR product is used to transform sup0-E. coli strain such as MV1184 strain to obtain a plasmid containing the mutant odhA fragment. This fragment is inserted into the pBS4S plasmid and the obtained plasmid is used to transform ATCC13869-L strain according to a similar method as in Example 1 to thereby obtain a strain in which the plasmid is integrated into its chromosome. Then, a strain which is resistant to sucrose and sensitive to kanamycin is selected from these strains. The nucleotide sequence of odhA gene of the selected strains is determined and the strain in which function of α-KGDH is deficient by frameshift mutation in odhA gene is selected as ATCC13869-L30sucA8 (odhA8) strain. The other odhA mutant strains can be obtained by the similar procedures using the yggB mutant strain.

sucA801 strain in which a mutant odhA gene having a nucleotide sequence of SEQ ID NO: 44 is introduced can be obtained by a similar method as described above in which a primer of SEQ ID NO: 39 having a phosphorylated 5'-end is used instead of a primer of SEQ ID NO: 38.

sucA805 strain in which a mutant odhA gene having a nucleotide sequence of SEQ ID NO: 46 is introduced can be obtained by a similar method as described above in which a primer of SEQ ID NO: 40 having a phosphorylated 5'-end is used instead of a primer of SEQ ID NO: 38.

sucA77 strain in which a mutant odhA gene having a nucleotide sequence of SEQ ID NO: 48 is introduced can be obtained by a similar method as described above in which a primer of SEQ ID NO: 41 having a phosphorylated 5'-end is used instead of a primer of SEQ ID NO: 38.

The L30sucA8 strain does not have intracellular α-KGDH because the sucA8 mutation is a frame-shift mutation which causes immature truncation of α-KGDH protein. On the other hand, sucA801 strain, sucA805 strain, and sucA77 strain have decreased but some α-KGDH activity because these mutations are not frame-shift mutations and do not cause immature truncation of α-KGDH protein.

TABLE 6 partial nucleotide acid sequence of the odhA mutant genes

| Strains | Nucleotide sequence of the odhA gene |
|---|---|
| ATCC13869-L | CTG GCT AAG CTG CGT GGC TAC GAC GTC GGA GGC ACC |
| L30sucA8 | CTG GCT AAG CTG CGT         C GAC GTC GGA GGC ACC |
| L30sucA801 | CTG GCT AAG CTG CGT      CTC GAC GTC GGA GGC ACC |
| L30sucA805 | CTG GCT AAA AGC TGC      GTC GAC GTC GGA GGC ACC |
| L30sucA77 | CTG GCT ATA AGC TGC      GTC GAC GTC GGA GGC ACC |

TABLE 7 amino acid sequence of the odhA mutants

| Strains | Amino acid sequence of the E1o subunit |
|---|---|
| wild | Leu Ala Lys Leu Arg Gly Tyr Asp Val Gly Gly Thr |
| L30sucA8 (Δ sucA) | Leu Ala Lys Leu Arg      Arg Arg Arg Arg His |
| L30sucA801 | Leu Ala Lys Leu Arg --- Leu Asp Val Gly Gly Thr |
| L30sucA805 | Leu Ala Lys Ser Cys --- Val Asp Val Gly Gly Thr |
| L30sucA77 | Leu Ala Ile Ser Cys --- Val Asp Val Gly Gly Thr |

<L-glutamic Acid Production using Strains Carrying each of the Mutant odhA Genes>

L-glutamic acid productivity of the obtained odhA mutant strains was evaluated by culturing these strains in Sakaguchi flask. Each of the strains listed in Table 6 was cultured at 31.5° C. overnight on CM-Dex agar medium, and then ⅙ of the culture was transferred to 20 ml of a medium containing 60 g/l glucose, 22.5 g/l $(NH_4)_2SO_4$, 1 g/l $KH_2PO_4$, 0.4 g/l $MgSO_4.7H_2O$, 0.01 g/l $FeSO_4.7H_2O$, 0.01 g/l $MnSO_4.4–5H_2O$, 200 µg/l vitamin B1, 0.48 g/l soybean protein hydrolysate, and 300 µg/l biotin (adjusted to pH 8.0 with KOH), added with $CaCO_3$ and cultured with stirring at 115 rpm at 31.5° C. The amount of accumulated L-glutamic acid after 19 hours of culture was shown in Table 8. The sucA801, sucA805, and sucA77 strains exhibited higher L-glutamic acid productivity than the ATCC13869-L strain carrying a wild-type odhA gene and the sucA8 strain carrying odhA gene with a frame-shift mutation. These results showed that L-glutamic acid is efficiently produced by regulating KGDH activity by introducing mutations into the proximate of thiamine pyrophosphate binding region of the odhA gene.

TABLE 8

L-glutamic acid production by odhA mutant strains

| Strain | L-glutamic acid (g/L) |
|---|---|
| ATCC13869-L | 4.9 |
| L30sucA8 | 19.8 |
| L30sucA801 | 22.1 |
| L30sucA805 | 23.8 |
| L30sucA77 | 21.6 |

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP2004-264458, is incorporated by reference herein in its entirety.

We claim:

1. A method for producing L-glutamic acid comprising:
   a) culturing an L-glutamic acid-producing coryneform bacterium in a culture medium, and
   b) collecting L-glutamic acid from the culture medium and/or the bacterium, wherein said bacterium comprises a mutation in the bacterium's chromosome which causes deletion of one or more amino acids in the region corresponding to amino acids 218 to 224 of SEQ ID NO: 10, and
wherein said bacterium is *Corynebacterium glutamicum* or *Brevibacterium lactofermentum*, and intracellular α-ketoglutarate dehydrogenase activity in said bacterium is less than half that of a non-mutated or wild-type strain.

2. The method according to claim 1, wherein said bacterium comprises a mutant chromosomal odhA gene that encodes a protein comprising the amino acid sequence shown in SEQ ID NO: 12.

3. The method according to claim 2, wherein said mutant chromosomal odhA gene comprises the nucleotides 443 to 4213 of SEQ ID NO: 11.

4. An isolated strain of *Corynebacterium glutamicum* or *Brevibacterium lactofermentum*, wherein said strain comprises a mutant chromosomal odhA gene that encodes a protein comprising the amino acid sequence shown in SEQ ID NO: 12.

5. An isolated strain of *Corynebacterium glutamicum* or *Brevibacterium lactofermentum*, wherein said strain comprises a mutant chromosomal odhA gene that comprises the nucleotides 443 to 4213 of SEQ ID NO: 11.

6. The method of claim 1, wherein said bacterium grows at a rate which is at least 80% as compared to the growth rate of a non-mutated or wild-type strain.

7. The method according to claim 6, wherein said bacterium comprises a mutant chromosomal odhA gene that encodes a protein comprising the amino acid sequence shown in SEQ ID NO: 12.

8. The method according to claim 7, wherein said mutant chromosomal odhA gene comprises the nucleotides 443 to 4213 of SEQ ID NO: 11.

* * * * *